United States Patent
Atassi

(10) Patent No.: US 7,635,484 B2
(45) Date of Patent: *Dec. 22, 2009

(54) BONT/A PEPTIDES AND METHODS OF PREDICTING AND REDUCING IMMUNORESISTANCE TO BOTULINUM TOXIN THERAPY

(75) Inventor: M. Zouhair Atassi, Houston, TX (US)

(73) Assignees: Allergan, Inc., Irvine, CA (US); Baylor College of Medicine, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/693,111

(22) Filed: Mar. 29, 2007

(65) Prior Publication Data

US 2007/0179281 A1    Aug. 2, 2007

Related U.S. Application Data

(62) Division of application No. 10/821,669, filed on Apr. 9, 2004, now Pat. No. 7,341,843.

(51) Int. Cl.
    *A61K 39/385* (2006.01)
(52) U.S. Cl. .............................. 424/197.11; 424/239.1; 424/247.1; 424/810
(58) Field of Classification Search ........................ None
    See application file for complete search history.

(56) References Cited

U.S. PATENT DOCUMENTS

| 4,551,435 | A | 11/1985 | Liberti et al. |
|---|---|---|---|
| 4,643,718 | A | 2/1987 | Marten |
| 5,668,255 | A * | 9/1997 | Murphy ..................... 530/350 |
| 6,048,529 | A | 4/2000 | Atassi et al. |
| 6,667,145 | B1 * | 12/2003 | Nishi et al. .............. 430/270.1 |
| 6,667,158 | B1 | 12/2003 | Bavari et al. |
| 6,676,622 | B2 | 1/2004 | Strahilevitz |
| 6,776,990 | B2 * | 8/2004 | Sachs et al. .............. 424/192.1 |
| 6,843,998 | B1 * | 1/2005 | Steward et al. ........... 424/236.1 |
| 7,214,787 | B1 * | 5/2007 | Smith et al. ................ 536/23.7 |
| 7,276,473 | B2 * | 10/2007 | Sachs et al. .................... 514/2 |

(Continued)

FOREIGN PATENT DOCUMENTS

| WO | 94/21684 | 9/1994 |
|---|---|---|
| WO | 2005/014798 | 2/2005 |
| WO | 2005/030119 | 4/2005 |

OTHER PUBLICATIONS

Krieglstein, Kerstin G et al, Journal of Protein Chemistry, vol. 13(1), 1994, pp. 49-57; Covalent Structure of Botulinum Neurotoxin Type A: Location of Sulfhydryl Groups and Disulfide Bridges and Identification of C-termini of Light and Heavy Chains.*

(Continued)

*Primary Examiner*—Robert B Mondesi
*Assistant Examiner*—Ginny Portner
(74) *Attorney, Agent, or Firm*—Dean G. Stathakis; Joel B. German; Debra D. Condino

(57) ABSTRACT

The present invention provides BoNT/A peptides as well as methods of predicting or determining immunoresistance to botulinum toxin therapy in an individual using BoNT/A peptides.

10 Claims, 28 Drawing Sheets

Synthetic BoNT/A Peptides

| Peptide Number | Sequence Position | Amino acid sequence |
|---|---|---|
| L-Peptide | 218–231 | A V T L A H E L I H A G H R |
| H_C-domain Peptides | | |
| N1 | 449–467 | A L N D L C I K V N N W D L P F S P S |
| N2 | 463–481 | P F S P S E D N F T N D L N K G E E I |
| N3 | 477–495 | K G E E I T S D T N I E A A E E N I S |
| N4 | 491–509 | E E N I S L D L I Q Q Y Y L T F N F D |
| N5 | 505–523 | T F N F D N E P E N I S I E N L S S D |
| N6 | 519–537 | N L S S D I I G Q L E L M P N I E R F |
| N7 | 533–551 | N I E R F P N G K K Y E L D K Y T M F |
| N8 | 547–565 | K Y T M F H Y L R A Q E F E H G K S R |
| N9 | 561–579 | H G K S R I A L T N S V N E A L L N P |
| N10 | 575–593 | A L L N P S R V Y T F F S S D Y V K K |
| N11 | 589–607 | D Y V K K V N K A T E A A M F L G W V |
| N12 | 603–621 | F L G W V E Q L V Y D F T D E T S E V |
| N13 | 617–635 | E T S E V S T T D K I A D I T I I I P |
| N14 | 631–649 | T I I I P Y I G P A L N I G N M L Y K |
| N15 | 645–663 | N M L Y K D D F V G A L I F S G A V I |
| N16 | 659–677 | S G A V I L L E F I P E I A I P V L G |
| N17 | 673–691 | I P V L G T F A L V S Y I A N K V L T |
| N18 | 687–705 | N K V L T V Q T I D N A L S K R N E K |
| N19 | 701–719 | K R N E K W D E V Y K Y I V T N W L A |
| N20 | 715–733 | T N W L A K V N T Q I D L I R K K M K |
| N21 | 729–747 | R K K M K E A L E N Q A E A T K A I I |
| N22 | 743–761 | T K A I I N Y Q Y N Q Y T E E E K N N |
| N23 | 757–775 | E E K N N I N F N I D D L S S K L N E |
| N24 | 771–789 | S K L N E S I N K A M I N I N K F L N |
| N25 | 785–803 | N K F L N Q C S V S Y L M N S M I P Y |
| N26 | 799–817 | S M I P Y G V K R L E D F D A S L K D |
| N27 | 813–831 | A S L K D A L L K Y I Y D N R G T L I |
| N28 | 827–845 | R G T L I G Q V D R L K D K V N N T L |
| N29 | 841–859 | V N N T L S T D I P F Q L S K Y V D N |

U.S. PATENT DOCUMENTS

| | | | | |
|---|---|---|---|---|
| 7,341,843 | B2* | 3/2008 | Atassi | 435/7.32 |
| 7,462,699 | B2* | 12/2008 | Atassi | 530/390.1 |
| 7,531,179 | B2* | 5/2009 | Atassi | 424/197.11 |
| 2001/0018049 | A1* | 8/2001 | Sachs et al. | 424/94.1 |
| 2002/0155114 | A1 | 10/2002 | Marks et al. | |
| 2002/0197278 | A1 | 12/2002 | Allison | |
| 2003/0009025 | A1* | 1/2003 | Smith et al. | 536/23.7 |
| 2003/0147895 | A1* | 8/2003 | Shone et al. | 424/178.1 |
| 2003/0185850 | A1* | 10/2003 | Dertzbaugh | 424/190.1 |
| 2004/0101534 | A1 | 5/2004 | Diamond | |
| 2004/0110284 | A1 | 6/2004 | Bavari et al. | |
| 2004/0175385 | A1 | 9/2004 | Marks et al. | |
| 2004/0176299 | A1* | 9/2004 | Sachs et al. | 514/12 |
| 2004/0191887 | A1* | 9/2004 | Chapman et al. | 435/252.3 |
| 2004/0248257 | A1* | 12/2004 | Kaye et al. | 435/69.1 |
| 2004/0265935 | A1 | 12/2004 | Atassi | |
| 2005/0095251 | A1* | 5/2005 | Steward et al. | 424/155.1 |
| 2005/0106182 | A1 | 5/2005 | Li et al. | |
| 2005/0244435 | A1* | 11/2005 | Shone et al. | 424/239.1 |
| 2007/0037257 | A1* | 2/2007 | Smith et al. | 435/69.3 |
| 2007/0048335 | A1* | 3/2007 | Gil et al. | 424/239.1 |

OTHER PUBLICATIONS

Dertzbaugh, Mark T et al, (1996) Vaccine, vol. 14(16), pp. 1538-1544, Mapping of protective and cross-reactive domains of the type a neurotoxin of Clostridium botulinum.*

Bavari, S et al, Vaccine, vol. 16(19), pp. 1850-1856, 1998, pp. 1850-1856.*

Montal, MS e tal, FEBS Lett. 1992, Nov. 16, vol. 31(3), pp. 12-18, abstract only.*

Kubota, Toru et al, Applied and Environmental Microbiology, Apr. 1997, pp. 1214-1218, vol. 63(4), Epitope regions in the Heavy Chain of Clostridium botulinum Type E Neurotoxin Recognized by Monoclonal Antibodies.*

Lebeda, Frank J. et al, Journal of Protein Chemistry, vol. 16(6), 1997, pp. 607-618, Predicint differential antigen-antibody contact regions based on solvent accessibility.*

Atassi, M. Zouhair, Scientific and Therapeutic Agents of Botulinum toxin 2002, Chapter 38, pp. 385-408, Immune recognition and Cross Reactivity of Botulinum Neurotoxins.*

Amersdorfer et al., "Genetic and immunological comparison of antibotulinum type A antibodies from immune and non-immune human phage libraries," *Vaccine* 20:1640-1648(2002).

Amersdorfer et al., "Molecular characterization of murine humoral immune response to botulinum neurotoxin type A binding domain as assessed by using phage antibody libraries," *Infect. Immun* 65:3743-3752 (1997).

Aoki, "Pharmacology and immunology of botulinum toxin serotypes," *J. Neurol.* 248 Suppl. 1:3-10(2001).

Atassi and Dolimbek, "Mapping of the antibody-binding regions on the HN-domain (residues 449-859) of botulinum neurotoxin A with antitoxin antibodies from four host species. Full profile of the continuous antigenic regions of the continuous antigenic regions of the H-chain of botulinum neurotoxin A," *Protein* J. 23:39-52 (2004).

Atassi and Oshima, "Structure, activity, and immune (T and B cell) recognition of botulinum neurotoxins" *Crit. Revs. Immunol*, 19:219-260 (1999).

Atassi and Smith, "A proposal for the nomenclature of antigenic sites in peptides and proteins," *Immunochemistry* 15:609-610 (1978).

Kozaki et al., "Development of antitoxin with each of two complementary fragments of *Clostridium botulinum* type B derivative toxin," *Infection and Immunity* 18:761-766 (1977).

Kozaki et al, "Immunological characterization of Papain-induced fragments of *Clostridium botulinum* type A neurotoxin and interaction of the fragments with brain synaptosomes "*Infection and Immunity* 57:2634-2639 (1989).

Kozaki et al., "The use of monoclonal antibodies to analyze the structure of *Clostridium botulinum* type E derivative toxin," *Infection and Immunity* 52:786-791 (1986).

Krieglstein, Kerstin G. et al, Journal of protein Chemistry, vol. 13(1), pp. 49-57, 1994.

Kubota et al., "Epitope regions in the heavy chain of *Clostridium bolulinum* type E neurotoxin recognized by monoclonal antibodies," *Applied & Environmental Microbiol*. 63:1214-1218 (1997).

Lacy et al, "Crystal structure of botulinum neurotoxin type A and implications for toxicity," *Nat. Struct. Biol*. 5:898-902 (1998).

Lacy, D. B. et al, "Sequence homology and structural analysis of the Clostridial neurotoxins", Journal of Molecular Biology, vol. 291, 1999, pp. 1091-1104.

LaPenotiere et al., "Expression of a large, nontoxic fragment of botulinum neurotoxin serotype A and its use as an immunogen," *Toxicon* 33:1383-1386(1995).

Lebeda, Frank J. et al, "Predicting Differential antigen-antibody contact regions based on solvent accessibility", Journal of Protein Chemistry, vol. 16(6), 1997, pp. 607-618.

Atassi et al., "Cross-reaction of mouse antibodies against Tetanus neurotoxin with Botulinum neurotoxins A and B," *International Conference 2002, Basic and Therapeutic Aspects of Botulinum and Tetanus Toxins*, Hannover, Germany, Jun. 8-12, Abstract R12 (2002).

Atassi et al., "Localization and synthesis of the hormone-binding regions of the human thyrotropin receptor," *Proc. Natl. Acad. Sci. USA* 88:3613-3617 (1991).

Atassi et al., "Mapping of the antibody-binding regions on botulinum neurotoxin H-chain domain 855-1296 with antitoxin antibodies from three host species," *J. Prot. Chem*. 15:691-700(1996).

Atassi, "Immune recognition and cross-reactivity of botulinum neurotoxins," in *Scientific and Therapeutic Aspects of Botulinum Toxins* (edited by Brin et al.), pp. 385-408, Lippincott Williams and Wilkins, Philadelphia, PA (2002).

Bavari et al., "Identifying the principal protective antigenic determinants of type A botulinum neurotoxin," *Vaccine* 16:1850-1856 (1998).

Beecher, DJ et al, J. Protein Chemistry, vol. 16(7), pp. 701-712, 1997.

Byrne, MP et al, vol. 82, 2000, "Development of vaccines for prevention of botulism", pp. 955-966.

Cenci Di Bello et al., "Antagonism of the intracellular action of botulinum neurotoxin type A with monoclonal antibodies that map to light-chain epitopes," *Eur. J. Biochem*. 219:161-169(1994).

Chen et al ., "Antibody mapping to domains of botulinum neurotoxin serotype A in the complexed and uncomplexed forms," Infect. Immun. 65:1626-1630 (1997).

Clayton and Middlebrook, "Vaccination of mice with DNA encoding a large fragment of botulinum neurotoxin serotype a," *Vaccine* 18:1855-1862 (2000).

Clayton et al., "Protective vaccination with a recombinant fragment of *Clostridium botulinum* , neurotoxin serotype A expressed from a synthetic gene in *Escherichia coli,*" *Infect. Immun*. 63:2738-2742 (1995).

Dertzbaugh and West, "Mapping of protective and cross-reactive domains of the type A neurotoxin of *Clostridium botulinum,*"*Vaccine* 14:1538-1544 (1996).

Dineen et al, Swiss Prot sequence Q8KHn9, Oct. 1, 2002.

Dolimbek and Alessi, "Protection against alpha-bungarotoxin poisoning by immunization with synthetic toxin peptides," *Mol. Immunol*. 33:681-689(1996).

Dolimbek et al., "Cross reaction of tetanus and botulinum neurotoxins A and B and the boosting effect of botulinum neurotoxins A and B on a primary anti-tetanus antibody response," *Immunological Investigations* 31:247-262(2002).

Dolimbek, BZ et al, Molecular Immunology, vol. 44, pp. 1029-1041,2007.

Dressler et al., "Antibody-induced botulinum toxin therapy failure: Can it be overcome by increased botulinum toxin doses?" *Eur. Neurol*. 47:118-121 (2002).

Gibson et al, Swiss Prot Accession No. Q97TT9, Oct. 1, 2001.

Goschel et al., "Botulinum A toxin therapy: Neutralizing and non-neutralizing antibodies—therapeutic consequences," *Exp. Neurol*. 147:96-102 (1997).

Hambleton et al., "A possible common antigen on clostridial toxins detected by monoclonal anti-botulinum neurotoxin antibodies," 449-450 (1984).

Hanna, Philip A. MD, Neurology, vol. 50(6), pp. 1624-1629, Jun. 1998.

Jankovic, "Botulinum Toxin: Clinical Implication sof Antigenicity and Immunoresistancey," in Brin et al. eds., *Scientific and Therapeutic Aspects of Botulinum Toxin*, pp. 409-415, Lippincott Williams & Wilkins, Philadelphia, PA (2002).

Jankovic, Joseph MD et al, Neurology, vol. 45(9), pp. 1743-1746, Sep. 1995.

Kikuyama eta al, Swiss Prot sequence Q9PRUI, May 1, 2000.

Klein, "Complications and adverse reactions with the use of botulinum toxin," *Dis. Mon.* 48:336-356(2002).

Middlebrook, "Protection strategies against botulinum toxin," in Atassi and Bixler (Eds.), *Immunology of Poreteins and Peptides VIII* p. 93-98 Plunum Press New York (1995).

Mullaney et al., "Epitope mapping of neutralizing botulinum neurotoxin A antibodies by phage display," *Infect. Immun.* 69:6511-6514 (2001).

Naumann et al., "Depletion of neutralizing antibodies resensitises a secondary non-responder to botulinum A neurotoxin," *J. Neurol. Neurosurg. Psychiatry* 65:924-927 (1998).

Naumann et al (1998), Immunol. Letters.

Oblatt-Montal, M. et al, "Formation of ion channels in lipid bilayers by a peptide with the predicted transmembrane sequence of botulinum neurotoxin A", Protein Science, vol. 4, 1995, pp. 1490-1497.

Oshima et al., "Antibodies and T cells against synthetic peptides of the C-terminal domain ($H_c$) of botulinum neurotoxin type A and their cross-reaction with $H_c$," *Immunol. Letters* 60:7-12 (1998), pp. 1031-1040.

Oshima et al, "Immune recognition of botulinum neurotoxin type A: Regions recognized by T cells and antibodies against the protective $H_c$ fragment (residues 855-1296) of the toxin,"*Mol. Immunol.* 34:1031-1040 (1997).

Pittman et al., "Antibody response to a delayed booster dose of anthrax vaccine and botulinum toxoid," *Vaccine* 20:2107-2115 (2002).

Pless et al., "High-affinity, protective antibodies to the binding domain of botulinum neurotoxin type A," *Infect. Immun*69:570-574 (2001).

Raju, R. et al, "Epitope repertoire of Human CD4+ lines propagated with Tetanus toxoid or with synthetic tetanus toxin sequences", Journal of autoimmunity, vol. 9, 1996, pp. 79-88.

Rosenberg et al., "Localization of the regions on the C-terminal domain of the heavy chain of botulinum A recognized by T lymphocytes and by antibodies after immunization of mice with pentavalent toxoid," *Immunol. Invest.* 26:491-504 (1997).

Shyu et al., "DNA vaccination using the fragment C of botulinum neurotoxin type A provided protective immunity in mice," *J. Biomed. Sci.* 7:51-57 (2000).

Simeckova-Rosenberg et al., "Protection of mice against lethal viral infection by synthetic peptides corresponding to B- and T-cell recognition sites of influenza A hemagglutinin," *Vaccine* 13:927-932 (1995).

Simpson, "The study of clostridial and related toxins. The search for unique mechanisms and common denominators," *J. Physiol., Paris* 84:143-151 (1990).

Singh et al, "Immunochemical characterization of Type A botulinum neurotoxin in its purifed and complexed forms.", Toxicon, 1996, vol. 36, No. 2, pp. 267-275.

Spanoyannis et al., "*Clostridium botulinum* type B neurotoxin demonstrates cross-reactivity with antibodies from patients with cervical dystonia who no longer respond to type A neurotoxin treatment," *Development Medicine and Child Neurology* 40:33 Scientific poster SP:8 (1998).

Tsuzuki et al., "Establishment of a monoclonal antibody recognizing an antigenic site common to *Clostridium botuliman* type B, $C_1$, D, and E toxins and tetanus toxin," *Infection and Immunity* 56:898-902 (1988).

Tugnoli, V et al, Expert. Opinion Investig. Drugs, 1997, Oct. vol. 6(10), pp. 1383-1394.

Wu et al., "Characterization of neutralizing antibodies and identification of neutralizing epitope mimics on the *Clostridium botulinum* neurotoxin type A," *Appl. Environ. Microbiol.* 67:3201-3207 (2001).

Office Action Date Mailed Dec. 28, 2007, U.S. Appl. No. 11/693,104.

Office Action Date Mailed Jan. 23, 2008, U.S. Appl. No. 11/576,219.

\* cited by examiner

Synthetic BoNT/A Peptides

| Peptide Number | Sequence Position | Amino acid sequence |
|---|---|---|
| L-Peptide | 218–231 | A V T L A H E L I H A G H R |

H$_N$-domain Peptides

| Peptide Number | Sequence Position | Amino acid sequence |
|---|---|---|
| N1 | 449–467 | A L N D L C I K V N N W D L F F S P S |
| N2 | 463–481 | F F S P S E D N F T N D L N K G E E I |
| N3 | 477–495 | K G E E I T S D T N I E A A E E N I S |
| N4 | 491–509 | E E N I S L D L I Q Q Y Y L T F N F D |
| N5 | 505–523 | T F N F D N E P E N I S I E N L S S D |
| N6 | 519–537 | N L S S D I I G Q L E L M P N I E R F |
| N7 | 533–551 | N I E R F P N G K K Y E L D K Y T M F |
| N8 | 547–565 | K Y T M F H Y L R A Q E F E H G K S R |
| N9 | 561–579 | H G K S R I A L T N S V N E A L L N P |
| N10 | 575–593 | A L L N P S R V Y T F F S S D Y V K K |
| N11 | 589–607 | D Y V K K V N K A T E A A M F L G W V |
| N12 | 603–621 | F L G W V E Q L V Y D F T D E T S E V |
| N13 | 617–635 | E T S E V S T T D K I A D I T I I I P |
| N14 | 631–649 | T I I I P Y I G P A L N I G N M L Y K |
| N15 | 645–663 | N M L Y K D D F V G A L I F S G A V I |
| N16 | 659–677 | S G A V I L L E F I P E I A I P V L G |
| N17 | 673–691 | I P V L G T F A L V S Y I A N K V L T |
| N18 | 687–705 | N K V L T V Q T I D N A L S K R N E K |
| N19 | 701–719 | K R N E K W D E V Y K Y I V T N W L A |
| N20 | 715–733 | T N W L A K V N T Q I D L I R K K M K |
| N21 | 729–747 | R K K M K E A L E N Q A E A T K A I I |
| N22 | 743–761 | T K A I I N Y Q Y N Q Y T E E E K N N |
| N23 | 757–775 | E E K N N I N F N I D D L S S K L N E |
| N24 | 771–789 | S K L N E S I N K A M I N I N K F L N |
| N25 | 785–803 | N K F L N Q C S V S Y L M N S M I P Y |
| N26 | 799–817 | S M I P Y G V K R L E D F D A S L K D |
| N27 | 813–831 | A S L K D A L L K Y I Y D N R G T L I |
| N28 | 827–845 | R G T L I G Q V D R L K D K V N N T L |
| N29 | 841–859 | V N N T L S T D I P F Q L S K Y V D N |

FIGURE 1A

H<sub>C</sub>-domain peptides

| | | |
|---|---|---|
| C1 | 855-873 | K Y V D N Q R L L S T F T E Y I K N I |
| C2 | 869-887 | Y I K N I N T S I L N L R Y E S N H |
| C3 | 883-901 | Y E S N H L I D L S R Y A S K I N I G |
| C4 | 897-915 | K I N I G S K V N F D P I D K N Q I Q |
| C5 | 911-929 | K N Q I Q L F N L E S S K I E V I L K |
| C6 | 925-943 | E V I L K N A I V Y N S M Y E N F S T |
| C7 | 939-957 | E N F S T S F W I R I P K Y F N S I S |
| C8 | 953-971 | F N S I S L N N E Y T I I N C M E N N |
| C9 | 967-985 | C M E N N S G W K V S L N Y G E I I W |
| C10 | 981-999 | G E I I W T L Q D T Q E I K Q R V V F |
| C11 | 995-1013 | Q R V V F K Y S Q M I N I S D Y I N R |
| C12 | 1009-1027 | D Y I N R W I F V T I T N N R L N N S |
| C13 | 1023-1041 | R L N N S K I Y I N G R L I D Q K P I |
| C14 | 1037-1055 | D Q K P I S N L G N I H A S N N I M F |
| C15 | 1051-1069 | N N I M F K L D G C R D T H R Y I W I |
| C16 | 1065-1083 | R Y I W I K Y F N L F D K E L N E K E |
| C17 | 1079-1097 | L N E K E I K D L Y D N Q S N S G I L |
| C18 | 1093-1111 | N S G I L K D F W G D Y L Q Y D K P Y |
| C19 | 1107-1125 | Y D K P Y Y M L N L Y D P N K Y V D V |
| C20 | 1121-1139 | K Y V D V N N V G I R G Y M Y L K G P |
| C21 | 1135-1153 | Y L K G P R G S V M T T N I Y L N S S |
| C22 | 1149-1167 | Y L N S S L Y R G T K F I I K K Y A S |
| C23 | 1163-1181 | K K Y A S G N K D N I V R N N D R V Y |
| C24 | 1177-1195 | N D R V Y I N V V V K N K E Y R L A T |
| C25 | 1191-1209 | Y R L A T N A S Q A G V E K I L S A L |
| C26 | 1205-1223 | I L S A L E I P D V G N L S Q V V V M |
| C27 | 1219-1237 | Q V V V M K S K N D Q G I T N K C K M |
| C28 | 1233-1251 | N K C K M N L Q D N N G N D I G F I G |
| C29 | 1247-1265 | I G F I G F H Q F N N I A K L V A S N |
| C30 | 1261-1279 | L V A S N W Y N R Q I E R S S R T L G |
| C31 | 1275-1296 | S R T L G C S W E F I P V D D G W G E R P L |

FIGURE 1B

H<sub>N</sub> domain of BoNT/A (Clostridium botulinum) (Residues 449-859 of SEQ ID NO:1)

```
A L N D L C I K V N N W D L F F S P S E D N F T N D L N K G E E
I T S D T N I E A A E E N I S L D L I Q Q Y Y L T F N F D N E P
E N I S I E N L S S D I I G Q L E L M P N I E R F N I E R F P N
G K K Y E L D K Y T M F H Y L R A Q E F E H G K S R I A L T N S
V N E A L L N P S R V Y T F F S S D Y V K K V N K A T E A A M F
L G W V E Q L V Y D F T D E T S E V S T T D K I A D I T I I I P
Y I G P A L N I G N M L Y K D D F V G A L I F S G A V I L L E F
I P E I A I P V L G T F A L V S Y I A N K V L T V Q T I D N A L
S K R N E K W D E V Y K Y I V T N W L A K V N T Q I D L I R K K
M K E A L E N Q A E A T K A I I N Y Q Y N Q Y T E E E K N N I N
F N I D D L S S K L N E S I N K A M I N I N K F L N Q C S V S Y
L M N S M I P Y G V K R L E D F D A S L K D A L L K Y I Y D N R
G T L I G Q V D R L K D K V N N T L S T D I P F Q L S K Y V D N
```

H<sub>C</sub> domain of BoNT/A (Clostridium botulinum) (Residues 855-1296 of SEQ ID NO:1)

```
K Y V D N Q R L L S T F T E Y I K N I I N T S I L N L R Y E S N
H L I D L S R Y A S K I N I G S K V N F D P I D K N Q I Q L F N
L E S S K I E V I L K N A I V Y N S M Y E N F S T S F W I R I P
K Y F N S I S L N N E Y T I I N C M E N N S G W K V S L N Y G E
I I W T L Q D T Q E I K Q R V V F K Y S Q M I N I S D Y I N R W
I F V T I T N N R L N N S K I Y I N G R L I D Q K P I S N L G N
I H A S N N I M F K L D G C R D T H R Y I W I K Y F N L F D K E
L N E K E I K D L Y D N Q S N S G I L K D F W G D Y L Q Y D K P
Y Y M L N L Y D P N K Y V D V N N V G I R G Y M Y L K G P R G S
V M T T N I Y L N S S L Y R G T K F I I K K Y A S G N K D N I V
R N N D R V Y I N V V V K N K E Y R L A T N A S Q A G V E K I L
S A L E I P D V G N L S Q V V V M K S K N D Q G I T N K C K M N
L Q D N N G N D I G F I G F H Q F N N I A K L V A S N W Y N R Q
I E R S S R T L G C S W E F I P V D D G W G E R P L
```

L-Peptide (amino acids 218-231 of SEQ ID NO:1)

A V T L A H E L I H A G H R

Amino acids 731 to 787 of BoNT/E (SEQ ID NO:2)

KNELTNKYDIKQIENELNQKVSIAMNNIDRFLTESSISYLMKLINEVKINKLREYDE

SEQUENCE LISTING

<160> NUMBER OF SEQ ID NOS: 2

<210> SEQ ID NO 1
<211> LENGTH: 1296
<212> TYPE: PRT
<213> ORGANISM: Clostridium botulinum

<400> SEQUENCE: 1

```
Met Pro Phe Val Asn Lys Gln Phe Asn Tyr Lys Asp Pro Val Asn Gly
 1               5                  10                  15

Val Asp Ile Ala Tyr Ile Lys Ile Pro Asn Val Gly Gln Met Gln Pro
                20                  25                  30

Val Lys Ala Phe Lys Ile His Asn Lys Ile Trp Val Ile Pro Glu Arg
            35                  40                  45

Asp Thr Phe Thr Asn Pro Glu Glu Gly Asp Leu Asn Pro Pro Pro Glu
        50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
```

-continued

```
                355                 360                 365
Phe Asp Lys Ala Val Phe Lys Ile Asn Ile Val Pro Lys Val Asn Tyr
    370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Asp Lys Gly Tyr Asn Lys
            435                 440                 445
Ala Leu Asn Asp Leu Cys Ile Lys Val Asn Asn Trp Asp Leu Phe Phe
    450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
            515                 520                 525
Glu Leu Met Pro Asn Ile Glu Arg Phe Pro Asn Gly Lys Lys Tyr Glu
    530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
                565                 570                 575
Leu Asn Pro Ser Arg Val Tyr Thr Phe Phe Ser Ser Asp Tyr Val Lys
            580                 585                 590
Lys Val Asn Lys Ala Thr Glu Ala Met Phe Leu Gly Trp Val Glu
            595                 600                 605
Gln Leu Val Tyr Asp Phe Thr Asp Glu Thr Ser Glu Val Ser Thr Thr
    610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
            660                 665                 670
Ile Pro Val Leu Gly Thr Phe Ala Leu Val Ser Tyr Ile Ala Asn Lys
            675                 680                 685
Val Leu Thr Val Gln Thr Ile Asp Asn Ala Leu Ser Lys Arg Asn Glu
    690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Lys Met Lys Glu Ala Leu
                725                 730                 735
Glu Asn Gln Ala Glu Ala Thr Lys Ala Ile Ile Asn Tyr Gln Tyr Asn
            740                 745                 750
Gln Tyr Thr Glu Glu Glu Lys Asn Asn Ile Asn Phe Asn Ile Asp Asp
            755                 760                 765
Leu Ser Ser Lys Leu Asn Glu Ser Ile Asn Lys Ala Met Ile Asn Ile
    770                 775                 780
```

```
Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
        820                 825                 830

Gln Val Asp Arg Leu Lys Asp Lys Val Asn Asn Thr Leu Ser Thr Asp
    835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg Leu
    1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
                1045                1050                1055

Leu Asp Gly Cys Arg Asp Thr His Arg Tyr Ile Trp Ile Lys Tyr Phe
            1060                1065                1070

Asn Leu Phe Asp Lys Glu Leu Asn Glu Lys Glu Ile Lys Asp Leu Tyr
        1075                1080                1085

Asp Asn Gln Ser Asn Ser Gly Ile Leu Lys Asp Phe Trp Gly Asp Tyr
    1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
            1140                1145                1150

Ser Leu Tyr Arg Gly Thr Lys Phe Ile Ile Lys Lys Tyr Ala Ser Gly
        1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200
```

-continued

```
Gly Val Glu Lys Ile Leu Ser Ala Leu Glu Ile Pro Asp Val Gly Asn
            1205                1210                1215

Leu Ser Gln Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265            1270                1275                1280

Ser Trp Glu Phe Ile Pro Val Asp Asp Gly Trp Gly Glu Arg Pro Leu
                1285                1290                1295

<210> SEQ ID NO 2
<211> LENGTH: 57
<212> TYPE: PRT
<213> ORGANISM: Clostridium botulinum

<400> SEQUENCE: 2

Lys Asn Glu Leu Thr Asn Lys Tyr Asp Ile Lys Gln Ile Glu Asn Glu
1               5                   10                  15

Leu Asn Gln Lys Val Ser Ile Ala Met Asn Asn Ile Asp Arg Phe Leu
            20                  25                  30

Thr Glu Ser Ser Ile Ser Tyr Leu Met Lys Leu Ile Asn Glu Val Lys
        35                  40                  45

Ile Asn Lys Leu Arg Glu Tyr Asp Glu
    50                  55
```

BONT/A PEPTIDES AND METHODS OF PREDICTING AND REDUCING IMMUNORESISTANCE TO BOTULINUM TOXIN THERAPY

This application is a divisional and claims priority pursuant to 35 U.S.C. §120 to U.S. patent application Ser. No. 10/821,669, filed Apr. 9, 2004, now U.S. Pat. No. 7,341,843, which is hereby incorporated by reference in its entirety.

FIELD OF INVENTION

This invention relates generally to the field of immunology, and, more specifically, to the use of botulinum toxin peptides and anti-botulinum toxin antibodies as diagnostic and therapeutic agents.

BACKGROUND OF THE INVENTION

Botulinum neurotoxins are proteins produced by several strains of the bacterium *Clostridium botulinum*, the spores of which are abundant in soil and marine sediments. These proteins are the most toxic substances known to man, being more lethal per molecule than diphtheria toxin, curare and sodium cyanide. There are seven distinct but related botulinum toxin serotypes, designated A through G. Botulinum toxin types A, B, E, and F are the most common causes of botulism in humans, while types C and D cause botulism in other mammals and birds. All seven botulinum toxin serotypes act by similar mechanisms and produce similar lethal effects when inhaled or ingested.

Botulinum toxins interrupt signals normally transmitted from nerve to muscle, thereby resulting in paralysis. Normally, electrical impulses that control muscle function are generated by the brain, brain stem and spinal cord, and these impulses travel from the originating area into peripheral nerves, which control motor function. At the end of these peripheral nerves are compartments for the neurotransmitter acetylcholine, a chemical messenger that transmits the electrical signal of the peripheral nerve to the muscle, instructing the muscle to contract. In the absence of botulinum toxin, acetylcholine is released into the junction between peripheral nerve and muscle when an electrical impulse reaches the storage compartment. The released acetylcholine binds to receptors located on the muscle, signaling the ensuing muscle contraction. However, botulinum toxin interferes with the release of acetylcholine into the junction, thereby blocking transmission of the electrical signal. Normal muscular contraction terminates due to the absence of the electrical signal.

In spite of their potentially deleterious effects, the ability of low, controlled doses of botulinum toxins to block acetylcholine release is useful in treating conditions characterized by unwanted muscular contraction or spasm resulting from excessive neural activity. Over the past 10 years, botulinum toxins have emerged as an important therapeutic tool for a number of neurological and ophthalmic conditions that have few other effective remedies. Injection of botulinum toxin into a specific muscle, commonly known as BOTOX® therapy, has been approved by the U.S. Food and Drug Administration for treatment of cervical dystonia (an asymmetric muscular spasm in the neck that results in forceful turning of the head), strabismus (misalignment of the eyes), focal spasm such as hemifacial spasm (unilateral muscle contractions of the face), and blepharospasm (involuntary forceful closure of the eyelids). Botulinum toxin also has been used to treat other conditions such as, without limitation, migraine headache, chronic low back pain, stroke, traumatic brain injury, cerebral palsy, urinary incontinence and various dystonias. The reduction in unwanted muscle spasm afforded by botulinum toxin therapy results in improved muscle function as well as pain relief in treated patients. As an example, among patients treated with BOTOX® for cervical dystonia, 90% experienced improved postural deviation, and 76-93% experienced pain relief following treatment.

A single BOTOX® injection generally provides therapeutic benefit for a duration of about 6 weeks to several months. Treatment is typically repeated at regular intervals to obtain sustained therapeutic benefit over time. However, in some cases, patients become nonresponsive to BOTOX® therapy. Resistance to therapy can occur, for example, due to the development in the patient of antibodies that bind to and inactivate the therapeutic toxin. Such antibody-mediated resistance to BOTOX®, which has been estimated to occur with a frequency of 3% to 10%, cannot be readily distinguished from other types of BOTOX® resistance based on the symptoms of the patient. In addition, there is currently no convenient diagnostic test available for detecting the presence of anti-botulinum toxin antibodies in a patient, nor is there a treatment available to prevent the onset of antibody-mediated resistance to BOTOX® therapy.

Thus, there exists a need for methods of predicting as well as reducing immunoresistance to botulinum toxin therapy. The present invention satisfies this need and provides related advantages as well.

SUMMARY OF INVENTION

The present invention provides a method of predicting or determining immunoresistance to botulinum toxin therapy in an individual by determining the presence or absence in the individual of antibodies immunoreactive with a BoNT/A peptide having a length of at most 60 amino acids and containing the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant or immunoreactive fragment thereof, where the presence of antibodies immunoreactive with the peptide indicates immunoresistance to botulinum toxin therapy, with the proviso that the BoNT/A peptide is not SEQ ID NO:2.

The present invention further provides a method of preventing or reducing immunoresistance to botulinum toxin therapy in an individual by administering to the individual a tolerogizing agent and a BoNT/A peptide having a length of at most 60 amino acids and containing the amino acid sequence 445-471 of SEQ ID NO: 1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant or immunoreactive fragment thereof, thereby preventing or reducing immunoresistance to botulinum toxin therapy, with the proviso that the BoNT/A peptide is not SEQ ID NO:2.

Also provided herein is a method of vaccinating an individual against botulinum toxin by administering to the individual a vaccine containing an adjuvant and a BoNT/A peptide which has a length of at most 60 amino acids and contains the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant or immunoreactive fragment thereof, thereby producing an immune response to botulinum toxin in the individual, with the proviso that the BoNT/A peptide is not SEQ ID NO:2. In one embodiment, a method of the invention is practiced using a BoNT/A peptide that contains the amino acid sequence 515-541 of SEQ ID NO:1, 529-555 of SEQ ID NO:1, 543-569 of SEQ ID NO:1, 585-611 of SEQ ID NO:1, 655-681 of SEQ ID NO:1, 739-765 of SEQ ID NO:1, 781-807 of SEQ ID NO:1, 809-835 of SEQ ID NO:1, or 823-849 of SEQ ID NO:1, or a conservative variant or immunoreactive fragment thereof, with the proviso that the BoNT/A peptide is not SEQ ID NO:2.

Also provided herein is a BoNT/A peptide that has a length of at most 60 amino acids and contains the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant or immunoreactive fragment thereof, with the proviso that the BoNT/A peptide is not SEQ ID NO:2.

Further provided herein is a tolerogizing composition containing a tolerogizing agent and a BoNT/A peptide having a length of at most 60 amino acids that includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1823-849 of SEQ ID NO:1, or 837-863 of SEQ ID NO:1, or a conservative variant or tolerogenic fragment thereof, with the proviso that the BoNT/A peptide is not SEQ ID NO:2.

In one embodiment, the BoNT/A peptide includes the amino acid sequence 515-541 of SEQ ID NO:1, 529-555 of SEQ ID NO:1, 543-569 of SEQ ID NO:1, 585-611 of SEQ ID NO:1, 655-681 of SEQ ID NO:1, 739-765 of SEQ ID NO:1, 781-807 of SEQ ID NO:1, 809-835 of SEQ ID NO:1, or 823-849 of SEQ ID NO:1, or a conservative variant or tolerogenic fragment thereof, with the proviso that the BoNT/A peptide is not SEQ ID NO:2.

The present invention further provides a vaccine composition that contains an adjuvant and a BoNT/A peptide having a length of at most 60 amino acids and including the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant or immunoreactive fragment thereof, with the proviso that the BoNT/A peptide is not SEQ ID NO:2. In one embodiment, the BoNT/A peptide includes the amino acid sequence 515-541 of SEQ ID NO:1, 529-555 of SEQ ID NO:1, 543-569 of SEQ ID NO:1, 585-611 of SEQ ID NO:1, 655-681 of SEQ ID NO:1, 739-765 of SEQ ID NO:1, 781-807 of SEQ ID NO:1, 809-835 of SEQ ID NO:1, or 823-849 of SEQ ID NO:1, or a conservative variant or immunoreactive fragment thereof, with the proviso that the BoNT/A peptide is not SEQ ID NO:2.

The invention additionally provides a method of preparing an anti-BoNT/A antibody by administering to an animal a BoNT/A peptide having a length of at most 60 amino acids and containing the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant or immunoreactive fragment thereof; collecting from the animal a sample containing an antibody or antibody-producing cell; and processing the sample to isolate the anti-BoNT/A antibody, with the proviso that the BoNT/A peptide is not SEQ ID NO:2. In one embodiment, a method of the invention is practiced with a BoNT/A peptide containing the amino acid sequence 515-541 of SEQ ID NO:1, 529-555 of SEQ ID NO:1, 543-569 of SEQ ID NO:1, 585-611 of SEQ ID NO:1, 655-681 of SEQ ID NO:1, 739-765 of SEQ ID NO:1, 781-807 of SEQ ID NO:1, 809-835 of SEQ ID NO:1, or 823-849 of SEQ ID NO:1, or a conservative variant or immunoreactive fragment thereof, with the proviso that the BoNT/A peptide is not SEQ ID NO:2.

BRIEF DESCRIPTION OF THE DRAWINGS

FIG. 1A shows synthetic consecutive overlapping peptides of the $H_N$ domain of BoNT/A having the indicated residues of SEQ ID NO:1. Regions of overlap with adjacent peptides are underlined and bolded. FIG. 1B shows synthetic consecutive overlapping peptides of the $H_C$ domain of BoNT/A having the indicated residues of SEQ ID NO:1. Regions of overlap with adjacent peptides are underlined and bolded. The L-peptide control sequence is shown as SEQ ID NO:1.

FIG. 6 shows amino acid sequences of the $H_N$ domain of BoNT/A (SEQ ID NO:1); the $H_C$ domain of BoNT/A (SEQ ID NO:1); the L peptide (SEQ ID NO:1); and amino acids 731 to 787 of BoNT/E (SEQ ID NO:2).

FIG. 7 shows proliferative responses of LNC ($8 \times 10^5$ cells/well) from BALB/c mice primed with 1:g of BoNT/A toxoid to BoNT/A, BoNT/B and TeNT.

FIG. 9 shows proliferative responses of BoNT/A, BoNT/B and TeNT of LNC ($7 \times 10^5$ cells/well) from SJL mice primed with 1:g BoNT/A toxoid.

Figure 15:
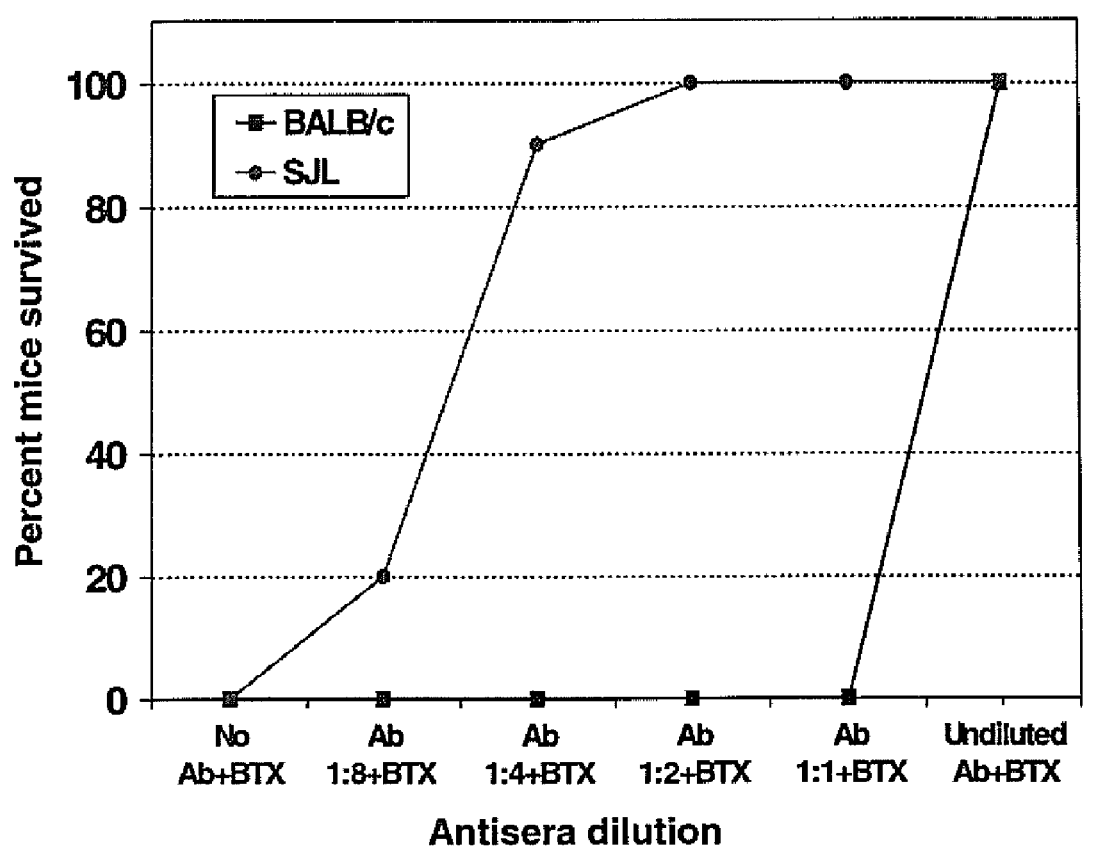

FIG. 15 shows protective activity of BALB/c and SJL anti-BoNT/A antisera obtained on day 36 after a first immunization. Antisera of each strain were tested at the indicated dilutions for their ability to protect recipient ICR mice against $1.05 \times LD_{100}$ of active BoNT/A. The results are expressed in percent survival to BoNT/A challenge versus antiserum dilution.

Figures 21, 22:
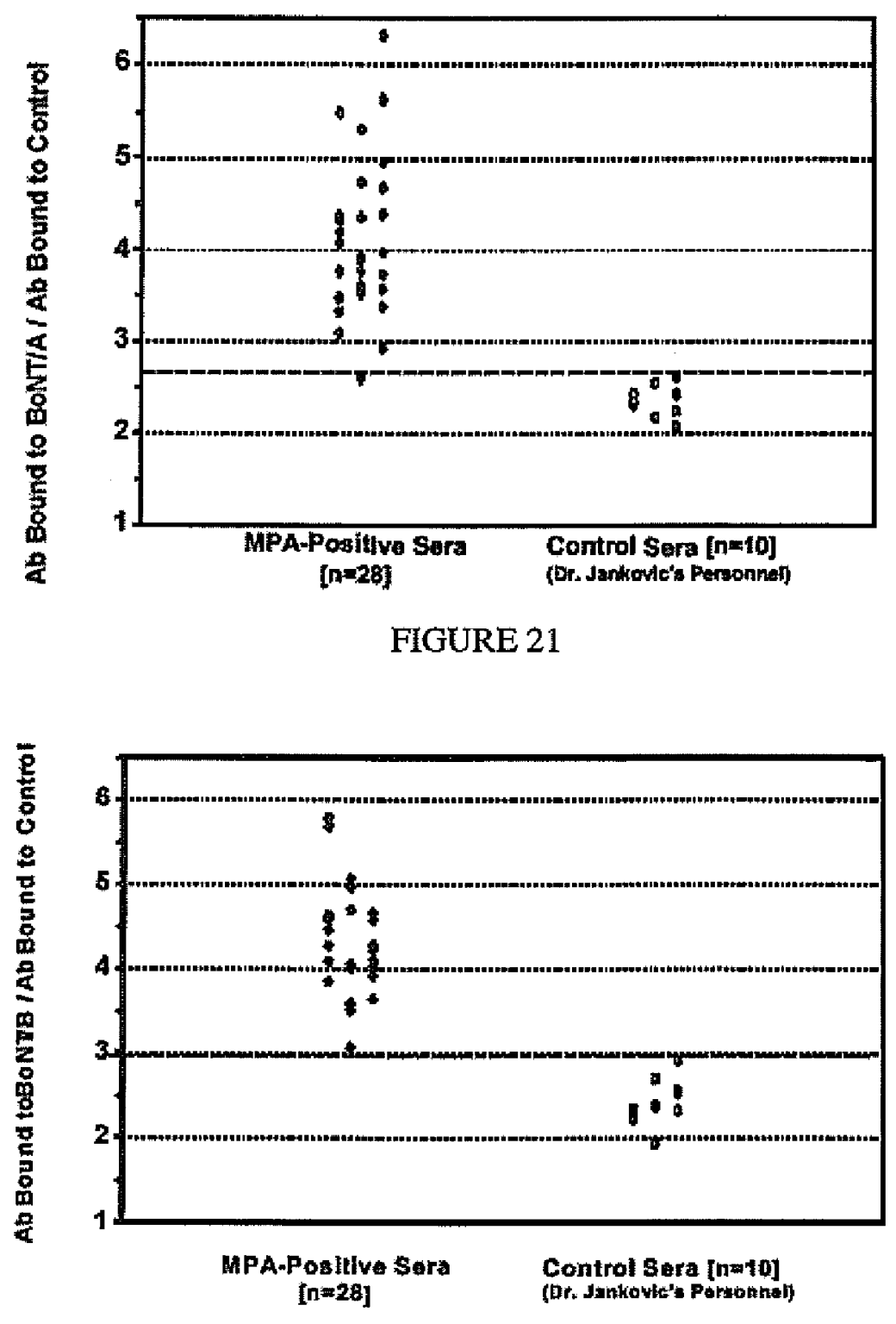

FIG. 21 shows binding to BoNT/A of antibodies in sera from CD patients (n=28) that are MPA-positive for anti-BoNT/A antibodies and in normal controls (n=10). Results are average of three experiments expressed in ratios of antibodies bound to BoNT/A over antibodies bound to negative controls.

FIG. 22 shows binding to BoNT/B of antibodies in MPA anti-BoNT/A positive sera from CD patients (n=28) and in normal controls (n=10). Results are in ratios of antibodies bound to BoNT/B over antibodies bound to negative controls.

DETAILED DESCRIPTION OF THE INVENTION

Figure 2:
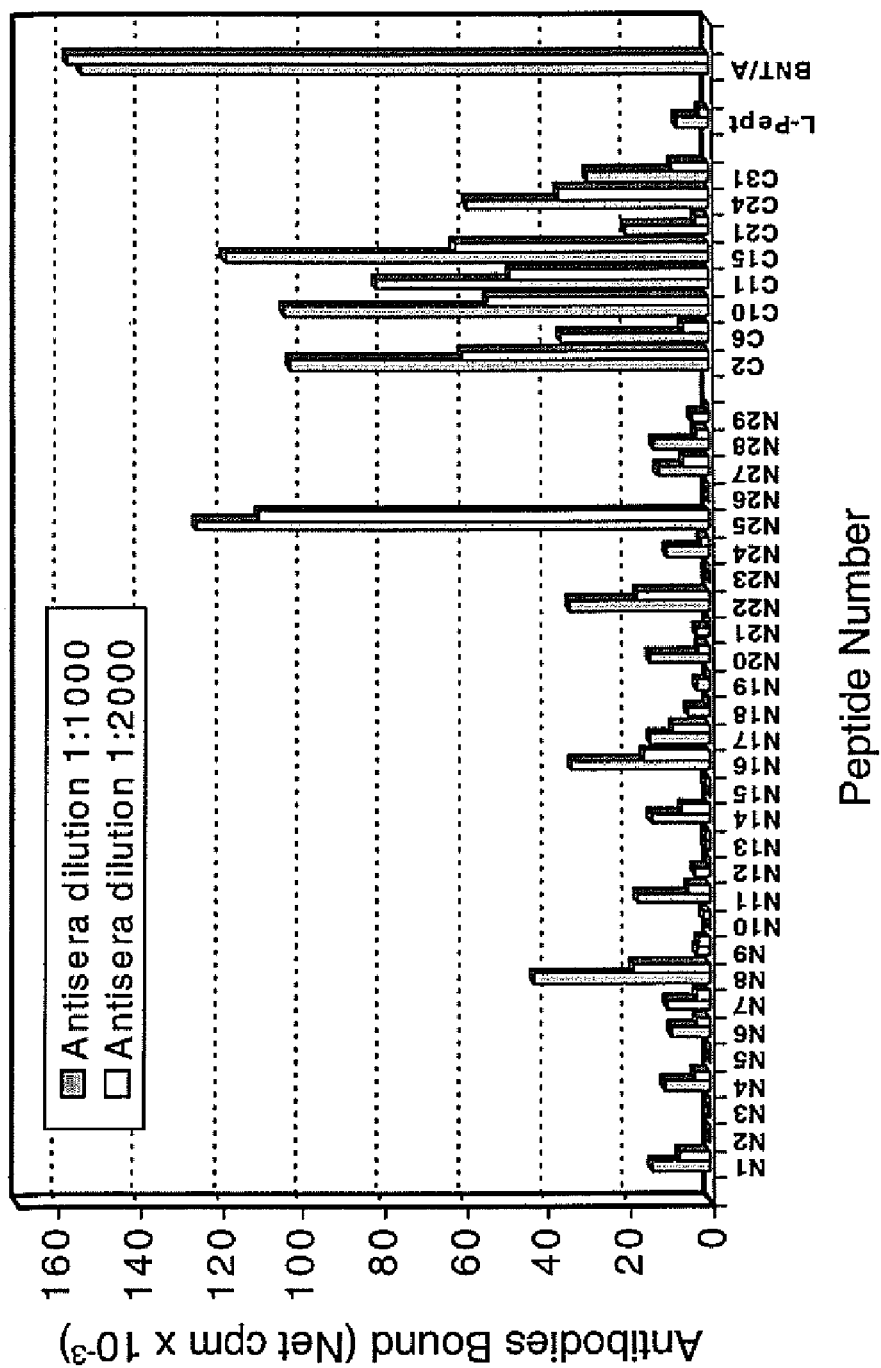
FIG. 2 shows binding of human anti-pentavalent botulinum toxoid antibodies to overlapping synthetic peptides spanning the BoNT/A $H_N$ domain and to active $H_C$ peptides. Also shown are binding to L-Peptide and full-length BoNT/A as negative and positive controls, respectively.

This invention relates to botulinum neurotoxin A (BoNT/A) peptides that represent the complete repertoire of epitopes from the $H_N$ domain of BoNT/A recognized by antibodies from humans immunized with pentavalent botulinum toxoid. BoNT/A peptides of the invention, and antibodies that bind to such peptides, are useful, for example, in methods for predicting or diagnosing immunoresistance to botulinum toxin therapy, for reducing the development of such immunoresistance, and for boosting immunity against unwanted botulinum toxicity.

Botulinum neurotoxins (BoNTs) are a group of protein neurotoxins produced by *Clostridium botulinum* that are among the most toxic substances known to man. Seven immunologically distinct BoNT serotypes (A through G) are known, including two subtypes of type C(C1 and C2). Botulinum neurotoxins are synthesized from a single polypeptide chain with a molecular weight of about 150 KDa, which is activated after secretion by nicking of a single peptide bond by an endogenous or exogenous protease. In *C. botulinum* strains that produce BoNTs A, C, D, and some types of B and F, the proteolytic enzyme is endogenous, while in other strains such as those that produce type E and some types B and F, the proteolytic enzyme is exogenous. The nicking of the progenitor toxin generally results in generation of two subunits, a 100 KDa heavy chain (H chain) and a 50 KDa light chain (L chain). With the exception of BoNT/C2, the two subunits are held together by a disulfide bond, which is important for neurotoxicity of toxin added extracellularly.

The cell intoxication mechanism of the BoNTs consists of four distinct steps: (1) binding; (2) internalization; (3) membrane translocation; and (4) enzymatic target modification. The carboxy-terminal part of the heavy chain (denoted the "$H_C$" domain) functions in neurospecific binding, while the amino-terminal portion of the H chain (denoted the "$H_N$" domain) functions in membrane translocation. The L chain is a zinc proteinase responsible for the intracellular activity of BoNTs, and has specificity for one or more of proteins involved in releasing acetylcholine into the neuromuscular junction.

The complete primary structures of BoNTs A through G have been determined (Binz et al., *J. Biol. Chem.* 265:9153 (1990); Willems et al., *Res. Microbiol.* 144:547 (1993); Hutson et al., *Curr. Microbiol* 28:101 (1994); Campbell et al., *Clin. Microbiol* 31:2255 (1993); Hauser et al., *Nucl. Acids Res.* 18:4924 (1990); Hauser et al., *Bacteriol.* 175:7260 (1993); Kimura et al., *Biochem. Biophys. Res. Commun.* 171: 1304 (1990); Kimura et al., *Appl. Environ. Microbiol.* 57:1168 (1991); Hauser et al., *Toxicon* 33:515 (1995); Binz et al., *Nucl. Acids Res.* 18:5556 (1990); Sunagawa et al., *J. Vet. Med. Sci.* 54:905 (1992); Campbell et al., *J. Clin. Microbiol.* 31:2255 (1993); Poulet et al., *Biochem. Biophys. Research Commun.* 183:107 (1992); Whelan et al., *Eur. J. Biochem.* 204:657 (1992); Campbell et al., *J. Clin. Microbiol.* 31:2255 (1993); East et al., *FEMS Microbiol. Lett.* 75:225 (1992); and Campbell et al., *Biochim. Biophys. Acta* 1216:487 (1993)). In addition, the disulfide pairing in BoNT/A has been determined. Several regions of homology exist within the amino acid sequences of the different serotypes of BoNT, as described in Atassi et al., *Critical Reviews in Immunology* 19:219-260 (1999).

The present invention relates to the discovery of small BoNT/A peptides which elicit antibody responses and represent the repertoire of epitopes within the BoNT/A $H_N$ domain recognized by four animal species, including humans. As shown herein in Examples I through IV, antigenic regions of the BoNT/A $H_N$ domain were mapped using human, mouse, chicken and horse sera obtained following immunization with BoNT/A. Mapping was performed using twenty nine BoNT/A peptides, each containing nineteen residues, that overlap consecutively by five residues and correspond to the entire length of the $H_N$ domain. The amino acid sequences of peptides used for mapping are shown in FIG. 1A. Results from the mapping studies revealed eighteen segments of BoNT/A that represent the complete repertoire of continuous antigenic regions on the BoNT/A $H_N$ domain.

As disclosed herein in Example VII, T- and B-cell recognition profiles of the BoNT/A $H_N$ domain were mapped in two inbred mouse strains, BALB/c ($H-2^d$) and SJL ($H-2^s$), that are high responders to BoNT/A. As summarized in Table 5, the results obtained with the two high-responder mouse strains demonstrate that responses to each antibody and T cell epitope are under separate genetic control and further indicate that there is partial overlap between antibody and T cell $H_N$ recognition regions.

Figure 16:
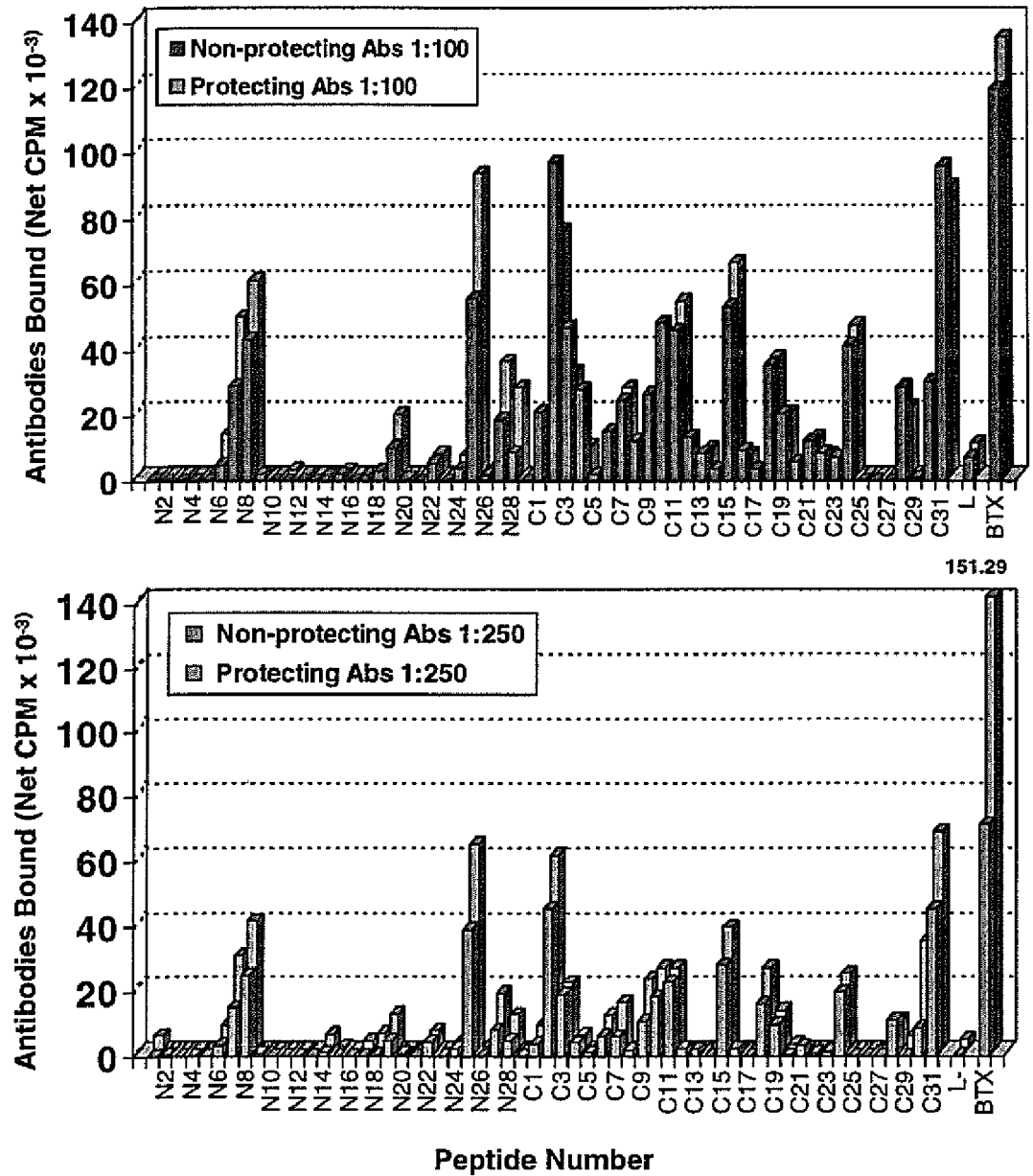
FIG. 16 shows binding of BALB/c total antibodies in nonprotecting (day 26) and protecting (day 36) anti-BoNT/A antisera to the overlapping synthetic peptides spanning the entire H chain and to the L-peptide around the enzyme active site of the L chain of BoNT/A. Results are from triplicate analyses and are expressed in net cpm, after correction for nonspecific binding in control wells coated with unrelated protein (BSA) or peptides and also controls of bound label to BoNT/A and to peptides in pre-immune serum of the same mice.
Figure 17:
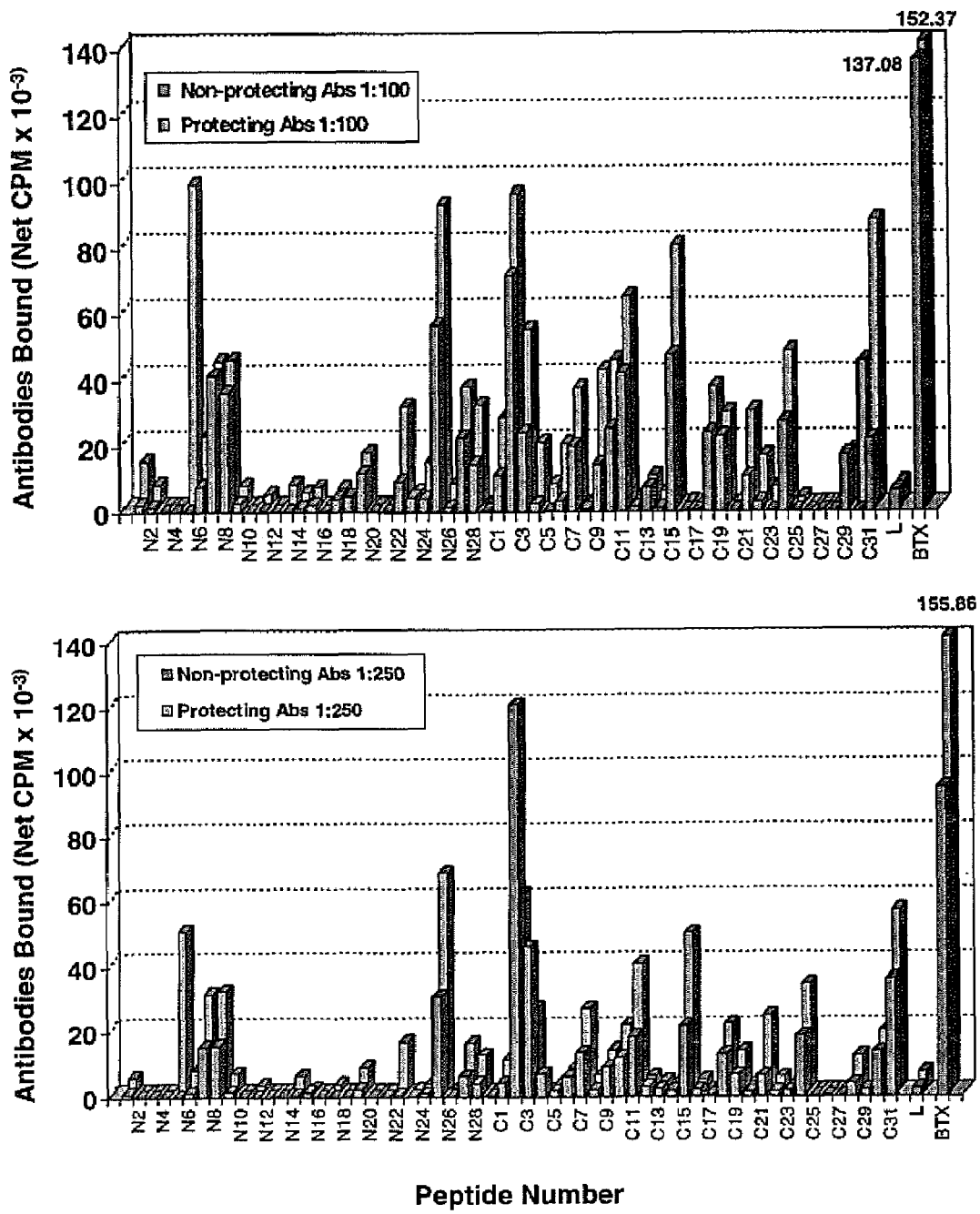
FIG. 17 shows binding of SJL total antibodies in nonprotecting (day 26) and protecting (day 36) anti-BoNT/A antisera to the overlapping synthetic peptides spanning the entire H chain and to the L-peptide around the enzyme active site of the L chain of BoNT/A. Results are from triplicate analyses and are expressed in net cpm, after correction as described above.
Figure 18:
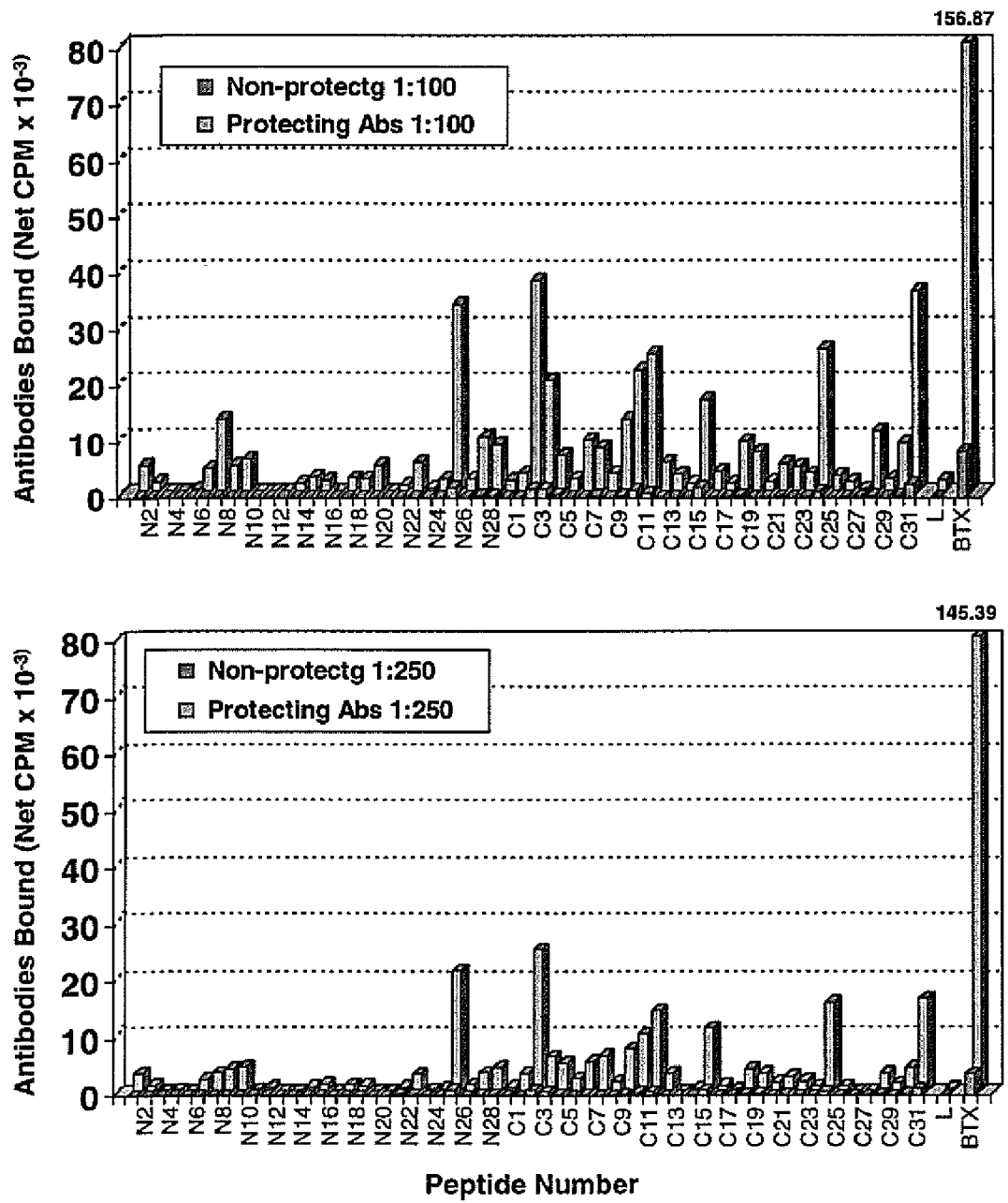
FIG. 18 shows binding of BALB/c IgG antibodies in nonprotecting (day 26) and protecting (day 36) anti-BoNT/A antisera to the overlapping synthetic peptides spanning the entire H chain and to the L-peptide around the enzyme active site of the L chain of BoNT/A. Results are from triplicate analyses and are expressed in net cpm, after correction as described above.
Figure 19:
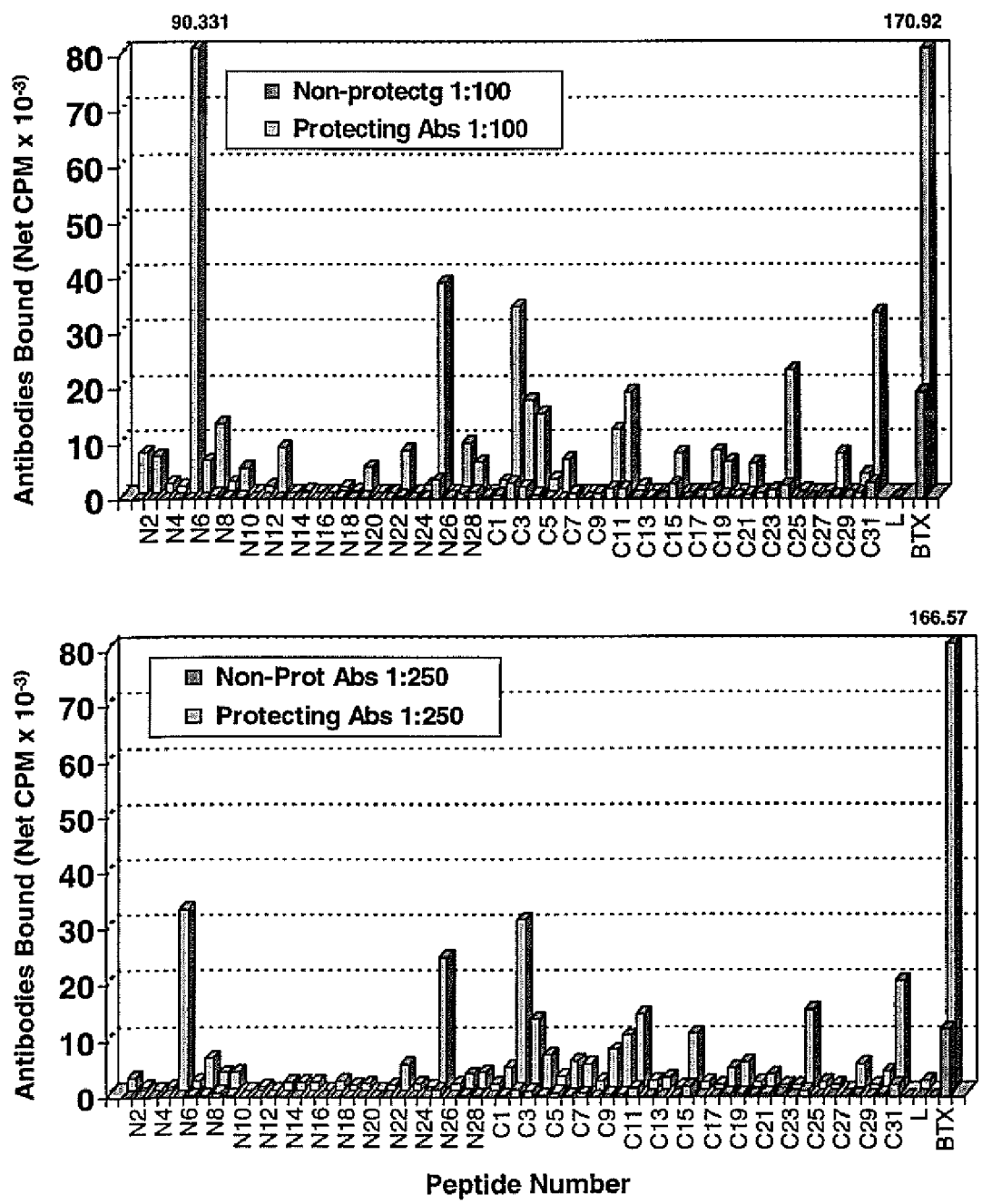
FIG. 19 shows binding of SJL IgG antibodies in nonprotecting (day 26) and protecting (day 36) anti-BoNT/A antisera to the overlapping synthetic peptides spanning the entire H chain and to the L-peptide around the enzyme active site of the L chain of BoNT/A. Results are from triplicate analyses and are expressed in net cpm, after correction as described above.
Figure 20:
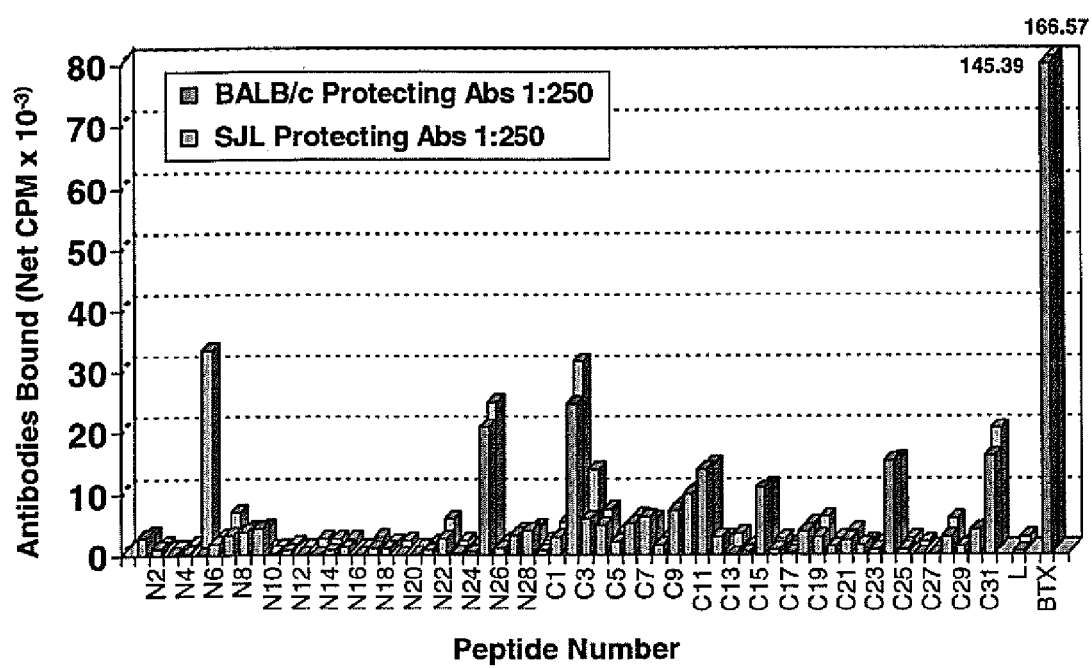
FIG. 20 shows a comparison of IgG antibody binding profiles from protective (day 36) BALB/c and SJL antisera. The data are the same as those shown in FIGS. 4 and 5. Binding studies were performed with antisera at a dilution of 1:250 (vol/vol).
Figure 23:
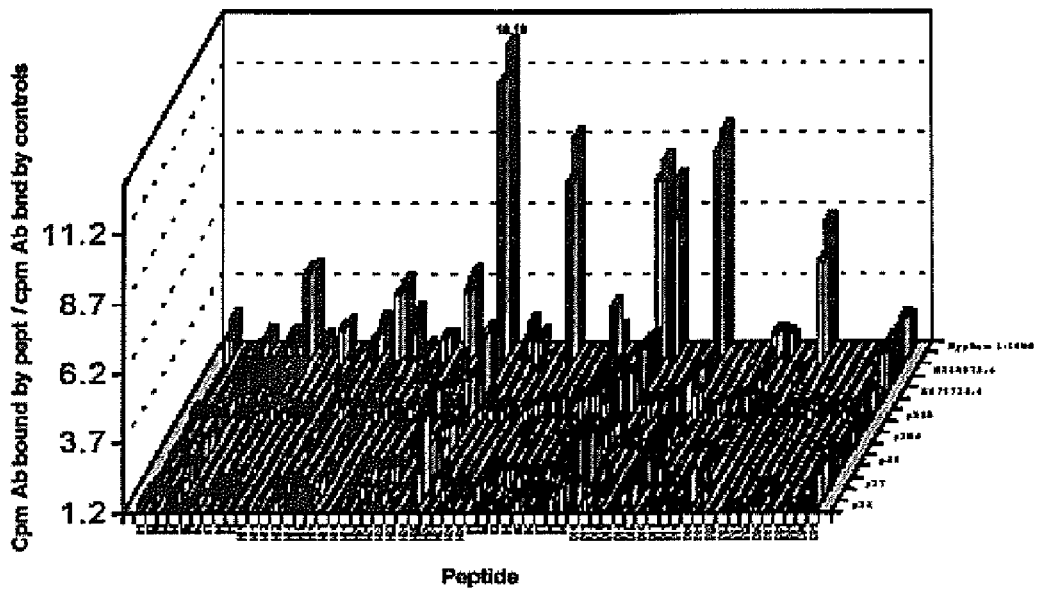
FIG. 23 shows mapping of the antibody recognition profile in serum samples from 13 CD patients. Results are expressed as a ratio of antibodies bound to peptides in the CD sera/average of antibodies bound by four negative control peptides.

Resistance in the majority of patients is associated with the appearance of blocking anti-toxin antibodies in patient serum (Goschel et al., *Exp. Neurol.* 147:96-102 (1997); Atassi and Oshima, *Crit. Revs. Immunol.* 19:219-260 (1999); Jankovic, in Brian et al., Eds., *Scientific and Therapeutic Aspects of Botulinum Toxin*, pp. 409-415, Lippincott Williams & Wilkins; Philadelphia, Pa. (2002). While all patient antibody responses against the toxin are not observed initially, additional injections of toxin appear to cause a switch of the non-blocking antibodies in the patient's serum to blocking antibodies. As further disclosed herein in Example VIII, the epitope recognition profile was compared in inbred BALB/c and SJL mice before and after the switch from production of non-protective to protective antibodies. The results disclosed herein demonstrated only slight differences in the epitope recognition profiles of non-protective and protective antisera, indicating that changes in antibody binding may not always protection, or lack thereof, by serum from a given strain (FIGS. 16 and 17). Furthermore, as shown in FIGS. 18 and 19, IgG antibodies in the protective antisera of each mouse strain bound to the same peptides as did total antibodies (IgG and IgM) in the same serum, while in both mouse strains, non-protective antisera contained few, if any, IgG antibodies to these peptides. These results appear to indicate that protection can be a function of immunoglobulin class, with IgG antibodies conferring protection against botulinum toxin.

Figure 24:
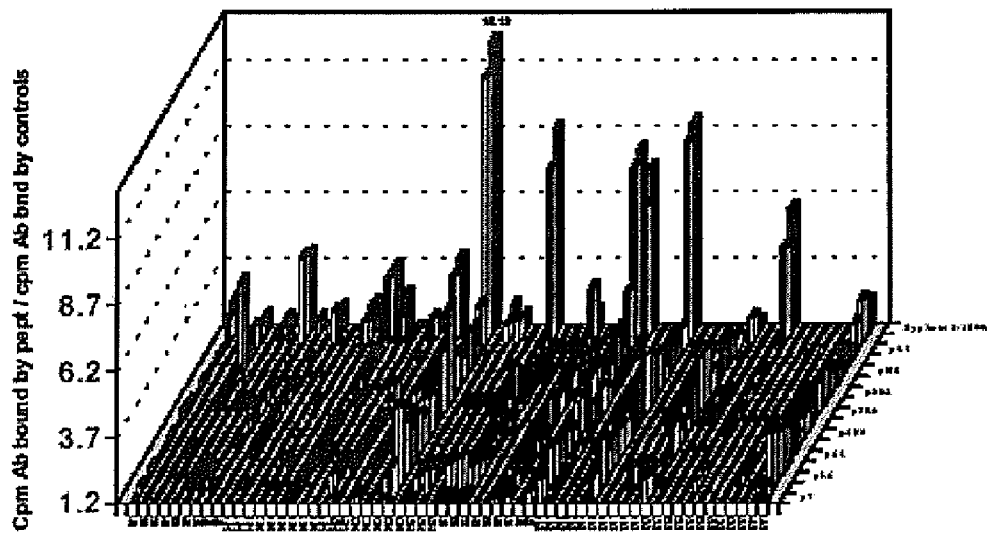
FIG. 24 shows mapping of the antibody recognition profile in serum samples from 15 CD patients. Results are expressed as a ratio of antibodies bound to peptides in the CD sera/average of antibodies bound by four negative control peptides.
Figure 25:
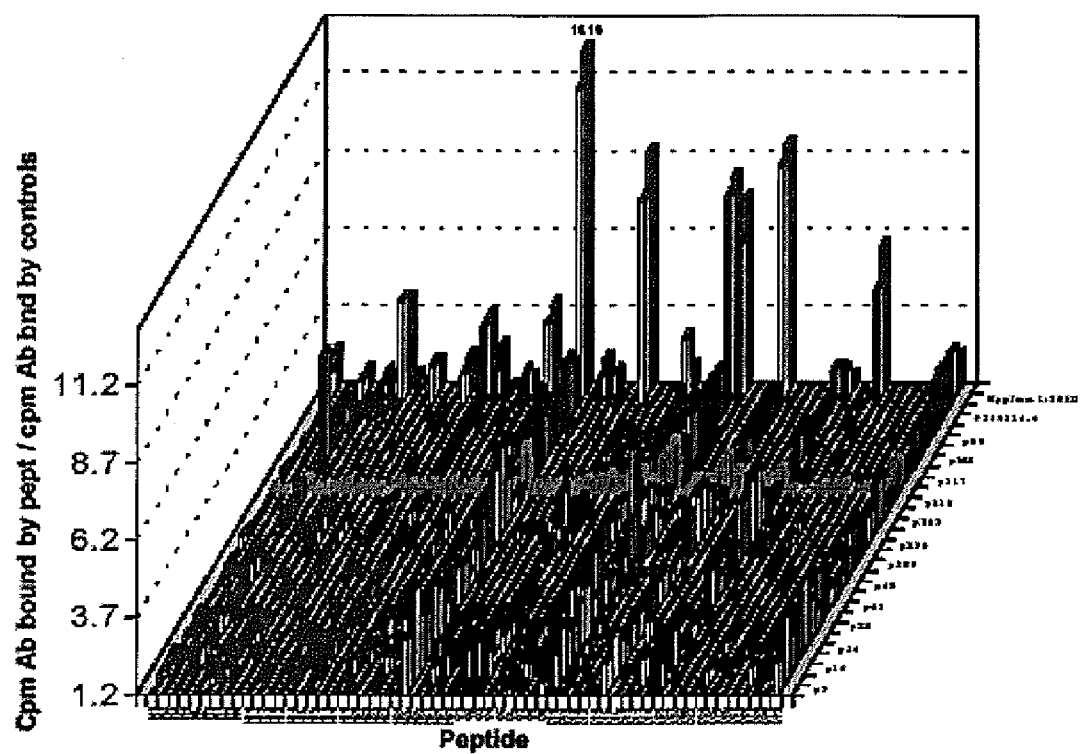
FIG. 25 shows mapping of the antibody recognition profile in serum samples from 28 CD patients. Results are expressed as a ratio of antibodies bound to peptides in the CD sera/average of antibodies bound by four negative control peptides.
Figure 26:
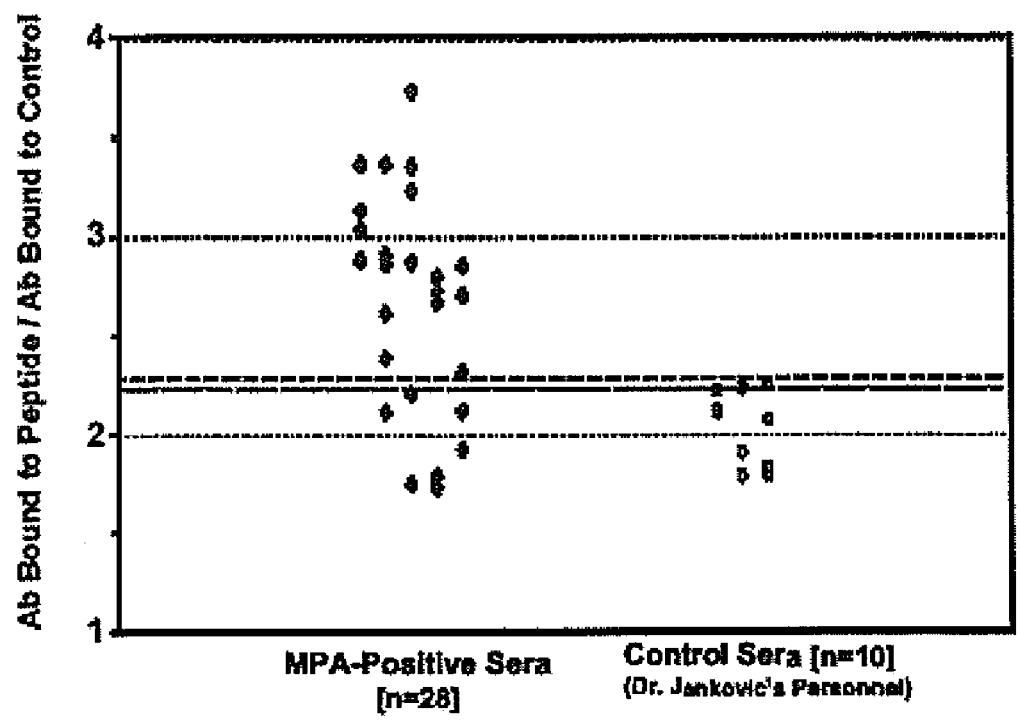
FIG. 26 shows binding to peptide N25 of antibodies in MPA-positive sera from CD patients (n=28) and in normal controls (n=10). Results are the average of four experiments and are expressed as a ratio of (antibodies bound to peptide N25)/(average of antibodies bound by negative control peptides N2, N12, C17 and C23).
Figure 27:
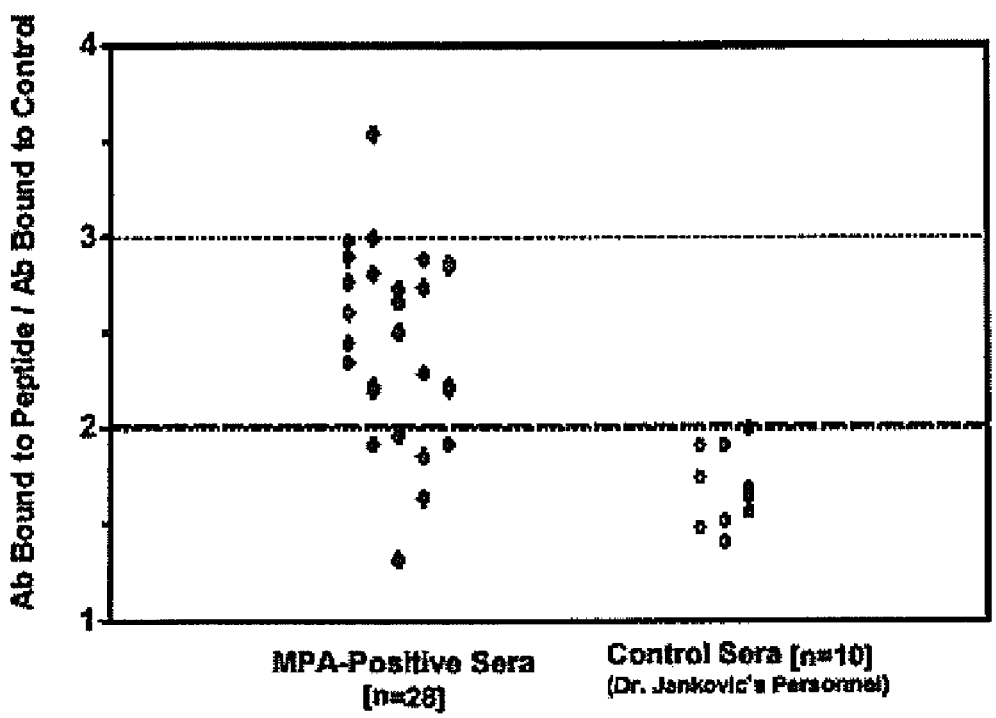
FIG. 27 shows binding to peptide C10 of antibodies in MPA-positive sera from CD patients (n=28) and in normal controls (n=10). Results are the average of four experiments and are expressed as a ratio of (antibodies bound to peptide C10)/(average of antibodies bound by negative control peptides N2, N12, C17 and C23).

Additional studies disclosed herein in Example IX demonstrate that in vitro binding assays performed in the presence of excess tetanus toxoid can be used to determine the levels of blocking or protective anti-BoNT/A antibodies in human serum samples. In particular, sera from 28 cervical dystonia patients containing protective antibodies as indicated by the mouse protection assay (MPA) and 10 negative control human sera from unimmunized controls were analyzed. As shown in FIGS. 24 to 26 and summarized in Table 6, peptides which bound antibodies in MPA-positive human patient sera also bound antibodies in hyperimmune mouse sera, while the antibody-binding profile of patient sera was more restricted than the profile of the hyperimmune sera. As further disclosed herein in Example IX, several peptides bound antibodies in most patient samples, with 25 out of 28 sera containing antibodies that bound peptide N25; 24 out of 28 sera containing antibodies that bound peptide C10; and lower binding to peptides C15, C20 and C31 seen in the majority of patient samples. These results indicate that, while there is some variability among the peptide-binding profiles of MPA-positive human sera, several synthetic BoNT/A peptides bind antibodies in the large majority of human patient sera that contain protective antibodies.

Figure 30:
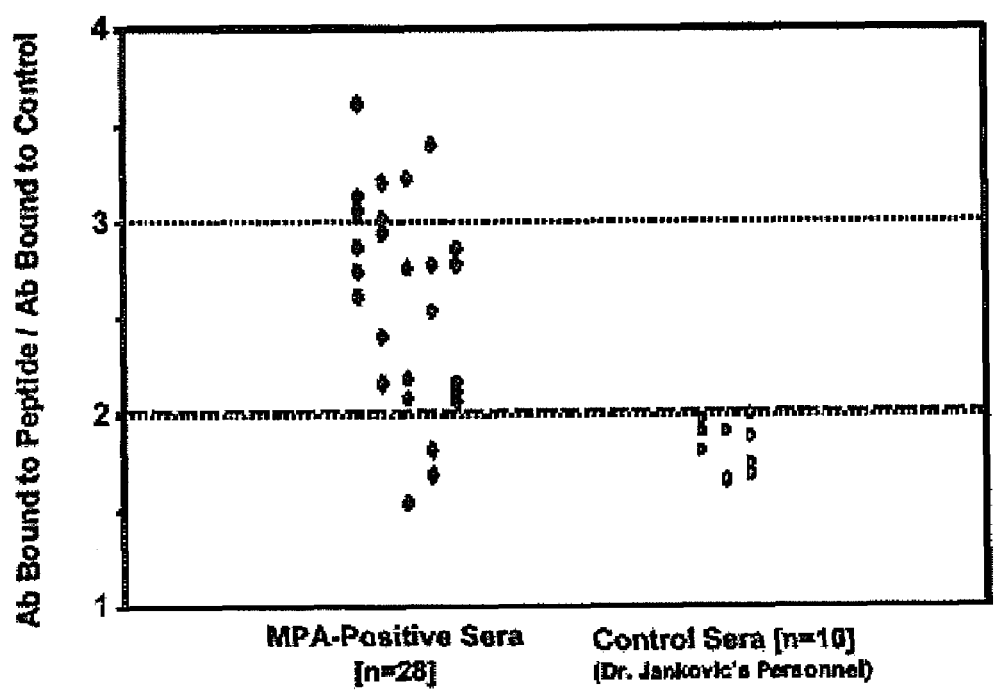
FIG. 30 shows binding to peptides (N25+C10) of antibodies in MPA-positive sera from CD patients (n=28) and in normal controls (n=10). The results, which are the average of four experiments, are expressed as a ratio of (antibodies bound to peptide N25+C10)/(average of antibodies bound by negative control peptides N2, N12, C17 and C23).
Figure 32:
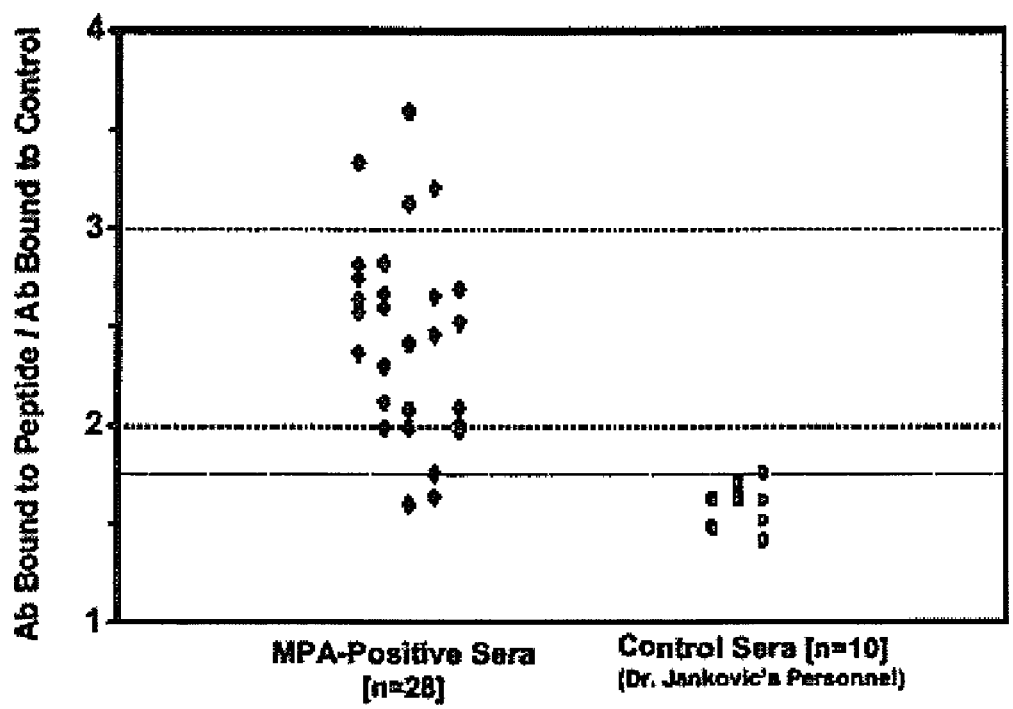
FIG. 32 shows binding to peptides (N25+C10+C15) of antibodies in MPA-positive sera from CD patients (n=28) and in normal controls (n=10). Results, which are the average of four experiments, are expressed as a ratio of (antibodies bound to peptides N25+C10+C15)/(average of antibodies bound by negative control peptides N2, N12, C17 and C23).

Further results disclosed herein demonstrate that an assay based on a combination of two or more synthetic BoNT/A peptides can be useful for detecting the presence of protective or blocking antibodies in the sera of patients treated with a BoNT/A formulation. As shown in FIG. 30, in an assay combining synthetic peptides N25 and C10, 25 out of 28 (89.3%) of the MPA-positive CD sera were discriminated from control sera. FIG. 32 shows that a combination of the synthetic peptides N25, C10 and C15 also served to distinguish 25 out of 28 (89.3%) of the MPA-positive CD sera from controls. Thus, the results disclosed herein demonstrate that a combination assay using peptides N25 and C10, or peptides N25, C10 and C15 can be useful for detecting the presence of specific antitoxin antibodies in BOTOX® treated patients. Furthermore, one or a combination of the synthetic peptides N25, C10, N15, N20 or N31, or a conservative variant or immunoreactive fragment thereof, also can be useful in a variety of diagnostic or therapeutic applications including, without limitation, methods of predicting or determining immunoresistance to botulinum toxin therapy; methods of preventing or reducing immunoresistance to botulinum toxin therapy and related tolerogenic compositions; methods of vaccinating against botulinum toxin and related vaccine compositions; methods of removing anti-botulinum toxin antibodies from blood, plasma or serum and affinity-matrices useful therefore; and new therapeutic formulations for blocking the effect of neutralizing antibodies in situ. Such therapeutic formulations include excess synthetic protective antibody-binding peptides together with the active toxin formulation.

BoNT/A Peptides

The present invention provides a BoNT/A peptide that has a length of at most 60 amino acids and contains the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant or immunoreactive fragment thereof, with the proviso that the BoNT/A peptide is not SEQ ID NO:2.

In one embodiment, such a BoNT/A peptide includes the amino acid sequence 515-541 of SEQ ID NO:1, 529-555 of SEQ ID NO:1, 543-569 of SEQ ID NO:1, 585-611 of SEQ ID NO:1, 655-681 of SEQ ID NO:1, 739-765 of SEQ ID NO:1, 781-807 of SEQ ID NO:1, 809-835 of SEQ ID NO:1, or 823-849 of SEQ ID NO:1, or a conservative variant or immunoreactive fragment thereof, with the proviso that the BoNT/A peptide is not SEQ ID NO:2. A BoNT/A peptide of the invention can have, for example, a length of at most 40 amino acids or a length of at most 25 amino acids.

In another embodiment, a BoNT/A peptide of the invention has a length of at most 60 amino acids and includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant thereof. In a further embodiment, a BoNT/A peptide of the invention has a length of at most 60 amino acids and includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or an immunoreactive fragment thereof, with the proviso that the BoNT/A peptide is not SEQ ID NO:2. In a further embodiment, a BoNT/A peptide of the invention has a length of at most 60 amino acids and includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1. In still a further embodiment, a BoNT/A peptide of the invention has the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1.

As used herein, the term "peptide" means two or more amino acids covalently bonded together. The term "BoNT/A peptide," as used herein, means a peptide having a length of at most 60 amino acids which includes an amino acid sequence having at least 50% amino acid identity with a portion of the BoNT/A sequence SEQ ID NO:1. Thus, a BoNT/A peptide can be, for example, a peptide of at most 60 amino acids having an amino acid sequence corresponding to a portion of the naturally occurring BoNT/A sequence SEQ ID NO:1, a peptide having one or more conservative or non-conservative substitutions relative to a portion of SEQ ID NO:1, a conservative variant of a portion of the BoNT/A sequence SEQ ID NO:1, or an immunoreactive fragment. The term "BoNT/A peptide" encompasses "variants," "conservative variants" and "immunoreactive fragments," each of which is described further below. Specifically excluded from the definition of a BoNT/A peptide is the 57-mer SEQ ID NO:2 described in Kubota et al., *Applied Envir. Microbiol.* 63:1214-1218 (1997). In one embodiment, a BoNT/A peptide is not SEQ ID NO:10 or a fragment thereof.

A BoNT/A peptide can have any of a variety of lengths up to 60 amino acids. In particular embodiments, a BoNT/A peptide includes at most 55 amino acids, 50 amino acids, 45 amino acids, 40 amino acids, 35 amino acids, 30 amino acids or 25 amino acids. In further embodiments, a BoNT/A peptide of the invention includes at most 55 amino acids of SEQ ID NO:1, at most 50 amino acids of SEQ ID NO:1, at most 45 amino acids of SEQ ID NO:1, at most 40 amino acids of SEQ ID NO:1, at most 35 amino acids of SEQ ID NO:1, at most 30 amino acids of SEQ ID NO:1, at most 25 amino acids of SEQ ID NO:1, at most 20 amino acids of SEQ ID NO:1 or at most 15 amino acids of SEQ ID NO:1 and further includes at least one of the following BoNT/A amino acid sequences: amino acids 445-471 of SEQ ID NO:1, amino acids 487-513 of SEQ ID NO:1, amino acids 515-541 of SEQ ID NO:1, amino acids 529-555 of SEQ ID NO:1, amino acids 543-569 of SEQ ID NO:1, amino acids 557-583 of SEQ ID NO:1, amino acids 585-611 of SEQ ID NO:1, amino acids 599-625 of SEQ ID NO:1, amino acids 627-653 of SEQ ID NO:1, amino acids 655-681 of SEQ ID NO:1, amino acids 669-695 of SEQ ID NO:1, 683-709 of SEQ ID NO:1, amino acids 711-737 of SEQ ID NO:1, amino acids 739-765 of SEQ ID NO:1, amino acids 767-793 of SEQ ID NO:1, amino acids 781-807 of SEQ ID NO:1, amino acids 809-835 of SEQ ID NO:1, 823-849 of SEQ ID NO:1, or amino acids 837-863 of SEQ ID NO:1 or a conservative variant or immunoreactive fragment thereof.

Conservative Variants

A BoNT/A peptide can contain conservative amino acid substitutions that do not substantially alter the antigenicity of the reference BoNT/A peptide having a sequence corresponding to a portion of SEQ ID NO:1. Such a "conservative variant" can function in substantially the same manner as a BoNT/A reference peptide, and can be substituted for the reference peptide in a method of the invention. As used herein in reference to a specified amino acid sequence, the term "conservative variant" means a sequence in which a first amino acid is replaced by another amino acid or amino acid analog that has least one biochemical property similar to that of the first amino acid; similar properties include, without limitation, similar size, charge, hydrophobicity or hydrogen-bonding capacity or a combination thereof. It is understood that conservative variants of BoNT/A peptides encompass, for example, conservative variants containing one, two, three, four or more amino acid substitutions relative to a portion of SEQ ID NO:1 and that such variants can include naturally and non-naturally occurring amino acid analogs as described further below.

As a non-limiting example, a conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be, for example, a sequence in which a first basic amino acid is conservatively substituted with a second basic amino acid such as arginine, lysine, histidine, 5-hydroxylysine, N-methyllysine or an analog thereof. Similarly, a conservative variant can be, for example, a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be, for example, a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof.

As a non-limiting example, conservative variants of BoNT/A peptides include conservative variants of a BoNT/A peptide having residues 445-471 of SEQ ID NO:1; such conservative variants can have, for example, an arginine for lysine substitution at position 456 and an isoleucine for leucine substitution at position 462. Additional conservative variants include conservative variants of the BoNT/A peptide having residues 487-513 of SEQ ID NO: 1; such conservative variants can have, for example, a glutamic acid for aspartic acid substitution at position 497; an asparagine for glutamine substitution at position 500; and a phenylalanine for tyrosine substitution at position 502.

Immunoreactive Fragments

The present invention further provides immunoreactive fragments of the BoNT/A peptides of the invention. Such immunoreactive fragments can be substituted for the corresponding full-length BoNT/A peptide in a method of the invention. As used herein in reference to a specified amino acid sequence, the term "immunoreactive fragment" means a portion of the specified BoNT/A amino acid sequence, or a conservative variant thereof, capable of selective antibody binding. An immunoreactive fragment can be capable of selective antibody binding to anti-BoNT/A antibodies from one or more species. In one embodiment, an immunoreactive fragment binds anti-BoNT/A antibodies from human sera.

An immunoreactive fragment of a BoNT/A peptide generally has from about six amino acids to 60 amino acids. An immunoreactive fragment of a BoNT/A peptide can have, for example, a length of at least 5, 6, 7, 8, 9, 10, 12, 15, 18, 20 or 25 amino acids. An immunoreactive fragment of a BoNT/A peptide also can have, for example, a length of at most 8, 9, 10, 12, 15, 18, 20, 25, 30 or 35 amino acids. In particular embodiments, an immunoreactive fragment of a BoNT/A peptide has from five to fifty amino acids, from eight to fifty amino acids, from ten to fifty amino acids, from five to twenty amino acids, from eight to twenty amino acids, from ten to twenty amino acids, from twelve to twenty amino acids or from fifteen to twenty amino acids. An immunoreactive fragment can have any number of conservative substitutions as discussed above.

An immunoreactive fragment can be identified using any of a variety of routine assays for detecting peptide antigen-antibody complexes, the presence of which is an indicator of selective binding. Such assays include, without limitation, enzyme-linked immunosorbent assays, radioimmunoassays, western blotting, enzyme immunoassays, fluorescence immunoassays, luminescent immunoassays and the like and generally are equivalent to the radioimmunoassay disclosed herein in Example I. Methods for detecting a complex between a peptide and an antibody, and thereby determining if the peptide is an "immunoreactive fragment" are well known to those skilled in the art and are described, for example, in Harlow and Lane, *Using Antibodies: A Laboratory Manual* New York: Cold Spring Harbor Laboratory Press (1998).

Variants

A BoNT/A peptide useful in the compositions and methods of the invention also can be a BoNT/A "variant," which as defined herein has an amino acid sequence having at least 50% amino acid identity with a portion of SEQ ID NO:1 and is capable of selective antibody binding. In particular embodiments, a BoNT/A variant has an amino acid sequence with at least 65% amino acid identity to a portion of SEQ ID NO:1 having at least 10 contiguous residues, 15 contiguous residues, 20 contiguous residues, or 25 contiguous residues of SEQ ID NO:1. In further embodiments, a BoNT/A variant has an amino acid sequence with at least 75% amino acid identity, 85% amino acid identity or 95% amino acid identity to a portion of SEQ ID NO:1 having at least 10 contiguous residues, 15 contiguous residues, 20 contiguous residues, or 25 contiguous residues of SEQ ID NO:1.

Peptidomimetics

A BoNT/A peptide such as, for example, a conservative variant, immunoreactive fragment or variant, also can contain one or more non-amide linkages between amino acids, or one or more amino acid analogs or mimetics, and further can have, for example, a cyclic or other conformationally constrained structure. As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as, without limitation, 4-hydroxyproline, hydroxylysine, desmosine, isodesmosine, homocysteine, citrulline and ornithine. Non-naturally occurring amino acids include, but are not limited to, (D)-amino acids, norleucine, norvaline, p-fluorophenylalanine, ethionine and the like. Amino acid analogs include modified forms of naturally and non-naturally occurring amino acids. Such modifications can include, for example, substitution or replacement of chemical groups or moieties on the amino acid or by derivitization of the amino acid. Amino acid mimetics include, for example, organic structures that exhibit functionally similar properties such as charge and charge spacing characteristic of the reference amino acid. As an example, an organic structure that mimics arginine can have a positive charge moiety located in similar molecular space and having the same degree of mobility as the e-amino group of the side chain of the naturally occurring arginine amino acid. Mimetics also include constrained structures which maintain advantageous spacing or charge interactions of the amino acid or amino acid functional groups. One skilled in the art understands that these and other well known amino acid analogs and mimetics can be useful in the BoNT/A peptides of the invention.

Specific examples of amino acid analogs and mimetics can be found described in, for example, Roberts and Vellaccio, *The Peptides: Analysis, Synthesis, Biology*, Eds. Gross and Meinhofer, Vol. 5, p. 341, Academic Press, Inc., New York, N.Y. (1983). Other non-limiting examples include peralkylated amino acids, particularly permethylated amino acids. See, for example, *Combinatorial Chemistry*, Eds. Wilson and Czarnik, Ch. 11, p. 235, John Wiley & Sons Inc., New York, N.Y. (1997). Further non-limiting examples include amino acids in which the amide portion has been replaced, for example, by a sugar ring, steroid, benzodiazepine or carbo cycle. See, for instance, *Burger's Medicinal Chemistry and Drug Discovery*, Ed. Manfred E. Wolff, Ch. 15, pp. 619-620, John Wiley & Sons Inc., New York, N.Y. (1995). Methods for synthesizing peptides include well known chemical synthesis methods. See, for example, U.S. Pat. No. 5,420,109; Chapter 7 of Bodanzsky, *Principles of Peptide Synthesis* (1st ed. & 2d rev. ed.), Springer-Verlag, New York, N.Y. (1984 & 1993); and Stewart and Young, *Solid Phase Peptide Synthesis*, (2d ed.), Pierce Chemical Co., Rockford, Ill. (1984).

Heterologous Fusions

A peptide of the invention can be fused to a heterologous protein, which is a protein derived from a source other than the gene encoding the peptide of the invention, to form a chimeric BoNT/A protein. Such a chimeric BoNT/A protein of the invention can have a variety of lengths including, but not limited to, a length of at most 100 residues, at most 200 residues, at most 300 residues, at most 400 residues, at most 500 residues, at most 800 residues or at most 1000 residues. Non-limiting examples of chimeric BoNT/A proteins include fusions of BoNT/A peptides with immunogenic polypeptides, such as flagellin and cholera enterotoxin; fusions of BoNT/A peptides with immunomodulatory polypeptides, such as IL-2 and B7-1; fusions of BoNT/A peptides with tolerogenic polypeptides, such as another BoNT/A peptide and an antibody selectively reactive with interleukin-12; and fusions of BoNT/A peptides with synthetic sequences.

Methods of Predicting or Determining Immunoresistance

BoNT/A peptides, including conservative variants and immunoreactive fragments of the amino acid sequences disclosed herein, each contain one or more epitopes recognized by antibodies contained in antisera from animals, for example, humans, immunized with BoNT/A. As described above, patients treated with botulinum toxin can develop immunoresistance to the therapeutic toxin, reducing or eliminating the beneficial effect of botulinum toxin therapy. The BoNT/A peptides of the invention are useful in methods of predicting or determining immunoresistance to botulinum toxin therapy in an individual.

Thus, the present invention provides a method of predicting or determining immunoresistance to botulinum toxin therapy in an individual by determining the presence or absence in the individual of antibodies immunoreactive with a BoNT/A peptide having a length of at most 60 amino acids and containing the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant or immunoreactive fragment thereof, where the presence of antibodies immunoreactive with the peptide indicates immunoresistance to botulinum toxin therapy, with the proviso that the BoNT/A peptide is not SEQ ID NO:2.

In a method of the invention, the BoNT/A peptide can include, for example, the amino acid sequence 515-541 of SEQ ID NO:1, 529-555 of SEQ ID NO:1, 543-569 of SEQ ID NO:1, 585-611 of SEQ ID NO:1, 655-681 of SEQ ID NO:1, 739-765 of SEQ ID NO:1, 781-807 of SEQ ID NO:1, 809-835 of SEQ ID NO:1, or 823-849 of SEQ ID NO:1, or a conservative variant or immunoreactive fragment thereof, with the proviso that the BoNT/A peptide is not SEQ ID NO:2. A BoNT/A peptide useful in the invention can have, for example, a length of at most 40 amino acids or a length of at most 25 amino acids.

In one embodiment, the BoNT/A peptide includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant thereof. In another embodiment, the BoNT/A peptide includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or an immunoreactive fragment thereof, with the proviso that the BoNT/A peptide is not SEQ ID NO:2. In a further embodiment, the BoNT/A peptide includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1. In still a further embodiment, the BoNT/A peptide has the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1.

A method of the invention for predicting or determining immunoresistance to botulinum toxin therapy can optionally include determining the presence or absence of antibodies immunoreactive with a $H_C$ peptide. $H_C$ peptides useful in the invention include, without limitation, those including the amino acid sequence 855-873 of SEQ ID NO:1, 869-887 of SEQ ID NO:1, 883-901 of SEQ ID NO:1, 897-915 of SEQ ID NO:1, 911-929 of SEQ ID NO:1, 925-943 of SEQ ID NO:1, 939-957 of SEQ ID NO:1, 953-971 of SEQ ID NO:1, 967-985 of SEQ ID NO:1, 981-999 of SEQ ID NO:1, 995-1013 of SEQ ID NO:1, 1009-1027 of SEQ ID NO:1, 1023-1041 of SEQ ID NO:1, 1037-1055 of SEQ ID NO:1, 1051-1069 of SEQ ID NO:1, 1065-1083 of SEQ ID NO:1, 1079-1097 of SEQ ID NO:1, 1093-1111 of SEQ ID NO:1, 1107-1125 of SEQ ID NO:1, 1121-1139 of SEQ ID NO:1, 1135-1153 of SEQ ID NO:1, 1149-1167 of SEQ ID NO:1, 1163-1181 of SEQ ID NO:1, 1177-1195 of SEQ ID NO:1, 1191-1209 of SEQ ID NO:1, 1205-1223 of SEQ ID NO:1, 1219-1237 of SEQ ID NO:1, 1233-1251 of SEQ ID NO:1, 1247-1265 of SEQ ID NO:1, 1261-1279 of SEQ ID NO:1, or 1275-1296 of SEQ ID NO:1, or a conservative variant or immunoreactive fragment thereof. In one embodiment, the $H_C$ peptide contains the amino acid sequence 939-957 of SEQ ID NO:1, 953-971 of SEQ ID NO:1, 967-985 of SEQ ID NO:1, 981-999 of SEQ ID NO:1, 995-1013 of SEQ ID NO:1, 1009-1027 of SEQ ID NO:1, 1023-1041 of SEQ ID NO:1, 1037-1055 of SEQ ID NO:1, 1051-1069 of SEQ ID NO:1, 1065-1083 of SEQ ID NO:1, 1079-1097 of SEQ ID NO:1, 1093-1111 of SEQ ID NO:1, 1107-1125 of SEQ ID NO:1, 1121-1139 of SEQ ID NO:1, 1135-1153 of SEQ ID NO:1, 1149-1167 of SEQ ID NO:1, 1163-1181 of SEQ ID NO:1, 1177-1195 of SEQ ID NO:1, 1191-1209 of SEQ ID NO:1, 1205-1223 of SEQ ID NO:1, 1219-1237 of SEQ ID NO:1, 1233-1251 of SEQ ID NO:1, 1247-1265 of SEQ ID NO:1, 1261-1279 of SEQ ID NO:1, or 1275-1296 of SEQ ID NO:1, or an immunoreactive fragment thereof.

In one embodiment, a method of the invention involves determining the presence or absence of antibodies immunoreactive with two or more BoNT/A peptides. In another embodiment, a method of the invention involves determining the presence or absence of antibodies immunoreactive with five or more BoNT/A peptides. In a further embodiment, a method of the invention involves determining the presence or absence of antibodies immunoreactive with ten or more BoNT/A peptides. The two or more, five or more, or ten or more BoNT/A peptides can be optionally immobilized on a solid support.

The present invention also provides methods of predicting or determining immunoresistance to botulinum toxin therapy in an individual by determining the presence or absence in the individual of antibodies immunoreactive with two or more of the following amino acid sequences: residues 785-803 of SEQ ID NO: 1 [N25]; 981-999 of SEQ ID NO: 1 [C10]; 1051-1069 of SEQ ID NO: 1 [C15]; 1121-1139 of SEQ ID NO: 1 [C20]; and 1275-1296 of SEQ ID NO: 1 [C31], or a conservative variant or immunoreactive fragment of any of these sequences, where the presence of antibodies immunoreactive with the two or more amino acid sequences indicates immunoresistance to botulinum toxin therapy. In one embodiment, one of the amino acid sequence includes residues 785-803 of SEQ ID NO: 1 [N25] or a conservative variant or immunoreactive fragment of this sequence. In another embodiment, a method of the invention is practiced by determining the presence or absence in the individual of antibodies immunoreactive with the following two amino acid sequences: 785-803 of SEQ ID NO: 1 [N25]; and 981-999 of SEQ ID NO: 1 [C10], or a conservative variant or immunoreactive fragment of any of these sequences. In still a further embodiment, a method of the invention is practiced by determining the presence or absence in the individual of antibodies immunoreactive with the following three amino acid sequences: 785-803 of SEQ ID NO: 1 [N25]; 981-999 of SEQ ID NO: 1 [C10]; and 1051-1069 of SEQ ID NO: 1 [C15], or a conservative variant or an immunoreactive fragment of any of these sequences. It is understood that the two or more amino acid sequences can be provided separately or as part of a compound molecule such as a chimeric synthetic peptide.

Any of the above methods of the invention can be practiced, if desired, by selectively determining the presence or absence in the individual of IgG antibodies immunoreactive with each of the amino acid sequences. Any of a variety of means can be used to determine the presence or absence of antibodies immunoreactive with each of the specified amino acid sequences including, yet not limited to, enzyme-linked immunosorbent assays and radioimmunoassays. In one embodiment, the botulinum toxin therapy is BoNT/A therapy.

A variety of assays are useful in a method of the invention for determining the presence or absence of antibodies immunoreactive with a BoNT/A peptide including, without limitation, enzyme-linked immunosorbent assays and radioimmunoassays. The methods of the invention can be useful for predicting or determining immunoresistance to any of a variety of botulinum toxin therapies including, but not limited to, BOTOX® therapy.

The term "immunoresistance," as used herein in reference to botulinum toxin therapy, means a reduction in beneficial effect of botulinum toxin therapy in an individual resulting from the presence in the individual of antibodies that bind to botulinum toxin. As used herein, the term "botulinum toxin therapy" means administration to an individual one or more controlled doses of botulinum toxin to obtain a beneficial therapeutic or cosmetic effect. The term botulinum toxin therapy encompasses, without limitation, the use of any naturally occurring or modified or engineered form of a botulinum toxin or a domain or fragment thereof, in any formulation, combined with any carrier or active ingredient and administered by any route of administration. An exemplary well-known botulinum toxin therapy is BOTOX® therapy. Appropriate therapeutic and cosmetic uses of botulinum toxin therapy are known in the art as discussed above.

A variety of assay formats employing one or more BoNT/A peptides of the invention can be used to determine the presence or absence of antibodies immunoreactive with a BoNT/A and, therefore, to predict or determine immunoresistance to botulinum toxin therapy according to a method of the invention. Such assay formats generally involve detecting an antigen-antibody interaction. Non-limiting examples include radioimmunoassays, enzyme immunoassays, fluorescence immunoassays, luminescent immunoassays and other nonradioisotopic assay formats. Non-competitive assays can be performed, for example, by attaching one or more selected BoNT/A peptides to a solid support; adding a test specimen; adding a secondary antibody, which is an antibody selective for the test antibody; and detecting the secondary antibody, typically by a physical property or enzymatic activity of the secondary antibody. In such an assay, the amount of signal that is detected can be proportional to the amount of antibodies which are immunoreactive with the one or more BoNT/A peptides and are present in the test specimen.

As a further non-limiting example, a competitive assay can be performed by attaching one or more selected BoNT/A peptides to a solid support; adding simultaneously a test specimen and an enzyme-labeled secondary antibody; and adding a substrate that produces a detectable compound when acted upon by the enzyme. In this type of assay format, the amount of signal that is detected is inversely proportional to the amount of BoNT antibody present in the test specimen.

In any assay format selected, a BoNT/A peptide of the invention optionally can be attached to a solid support. Such a solid support can be, without limitation, a tube, plate, column, particle or bead. The solid support selected can have a physical property that renders it readily separable from soluble or unbound material and generally allows unbound materials, such as unbound antibodies, to be washed away or otherwise removed from support-bound antibodies.

In one embodiment, the presence or absence of antibodies immunoreactive with a BoNT/A peptide is determined using an enzyme-linked immunosorbent assay (ELISA). In another embodiment, the presence or absence of antibodies immunoreactive with a BoNT/A peptide is determined using a radioimmunoassay.

It is understood that a method of the invention for predicting or determining immunoresistance to botulinum toxin therapy can be determined using a test specimen obtained from an individual prior to receipt of botulinum toxin therapy, after a single botulinum toxin treatment, after multiple botulinum toxin treatments, or after onset of resistance to botulinum toxin therapy. Useful test specimens include, but are not limited to, serum. It further is understood that a method of the invention can be used to predict the likelihood of an individual developing immunoresistance or to confirm that the presence of anti-BoNT antibodies are a cause underlying resistance to botulinum toxin therapy. In particular embodiments, a method of the invention for predicting or determining immunoresistance to botulinum toxin therapy in an individual involves determining the presence or absence of antibodies immunoreactive with two or more BoNT/A peptides, such as, without limitation, five or more BoNT/A peptides, ten or more BoNT/A peptides, or twenty or more BoNT/A peptides. In a further embodiment, a method of the invention further includes the step of determining the presence or absence of antibodies immunoreactive with an $H_C$ peptide.

BoNT/A Tolerogenic Compositions

A BoNT/A peptide of the invention can be combined with another substance to produce a tolerogizing composition useful for treating an individual. Thus, the present invention further provides a tolerogizing composition containing a tolerogizing agent and a BoNT/A peptide having a length of at most 60 amino acids that includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant or tolerogenic fragment thereof, with the proviso that the BoNT/A peptide is not SEQ ID NO:2. In one embodiment, the BoNT/A peptide includes the amino acid sequence 515-541 of SEQ ID NO:1, 529-555 of SEQ ID NO:1, 543-569 of SEQ ID NO:1, 585-611 of SEQ ID NO:1, 655-681 of SEQ ID NO:1, 739-765 of SEQ ID NO:1, 781-807 of SEQ ID NO:1, 809-835 of SEQ ID NO:1, or 823-849 of SEQ ID NO:1, or a conservative variant or tolerogenic fragment thereof, with the proviso that the BoNT/A peptide is not SEQ ID NO:2.

BoNT/A peptides useful in a tolerogizing composition of the invention can have, for example, a length of at most 40 amino acids or a length of at most 25 amino acids. In one embodiment, a tolerogizing composition of the invention contains a BoNT/A peptide that includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant thereof. In another embodiment, a tolerogizing composition of the invention contains a BoNT/A peptide that includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or an immunoreactive fragment thereof, with the proviso that the BoNT/A peptide is not SEQ ID NO:2. In a further embodiment, a tolerogizing composition of the invention contains a BoNT/A peptide that includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1. In still a further embodiment, a tolerogizing composition of the invention contains a BoNT/A peptide that has the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1. A variety of tolerogizing agents are useful in the invention including, without limitation, polyethylene glycol (PEG), monomethoxypolyethylene glycol (mPEG), and polyvinyl alcohol (PVA).

The tolerogizing compositions of the invention are useful, for example, for inducing specific immunological non-reactivity (tolerance) to a botulinum toxin antigen. Tolerance is an active antigen-dependent process that occurs in an individual in response to the antigen and results from a previous exposure to the same antigen. Various molecules are known in the art to cause, promote or enhance tolerance. See, for example, U.S. Pat. No. 5,268,454, and citations therein. As used herein, the term "tolerogizing agent" means a molecule, compound or polymer that causes, promotes or enhances tolerogenic activity when combined with a BoNT/A peptide of the invention.

A tolerogizing composition of the invention contains one or more tolerogizing agents, which can be present in a variety of forms. As non-limiting examples, a tolerogizing agent can be a liquid, solid, or emulsion, depending, for example, on the route of administration and physical properties of the tolerogizing agent. A tolerogizing agent also can be conjugated to a BoNT/A peptide in a tolerogizing composition of the invention. Non-limiting examples of tolerogizing agents include polyethylene glycol (PEG), monomethoxypolyethylene glycol (mPEG) and polyvinyl alcohol (PVA). Such tolerogizing agents can be conjugated to a BoNT/A peptide, for example, as described in Atassi et al., U.S. Pat. No. 6,048,529.

The term "tolerogenic fragment," as used herein in reference to a portion of SEQ ID NO:1, means a portion of the sequence, or a conservative variant thereof, that has tolerogenic activity as defined by the ability either alone, or in combination with another molecule, to produce a decreased immunological response. A tolerogenic fragment of a BoNT/A peptide can have from about three amino acids to about 60 amino acids. A tolerogenic fragment of a BoNT/A peptide can have, for example, at least 5, 8, 10, 12, 15, 18, 20 or 25 amino acids. A tolerogenic fragment of a BoNT/A peptide also can have, for example, at most 8, 10, 12, 15, 18, 20, 25, 30 or 35 amino acids. As non-limiting examples, a tolerogenic fragment of a BoNT/A peptide can have from five to fifty amino acids, from eight to fifty amino acids, from ten to fifty amino acids, from eight to twenty amino acids, from ten to twenty amino acids, from twelve to twenty amino acids or from fifteen to twenty amino acids.

A tolerogenic fragment of a BoNT/A peptide can be identified using any of a variety of assays, including in vitro assays such as T-cell proliferation or cytokine secretion assays and in vivo assays such as the induction of tolerance in animal models of botulinum toxicity. T-cell proliferation assays, for example, are well recognized in the art as predictive of tolerogenic activity (see, for example, Miyahara et al., *Immunol.* 86:110-115 (1995) or Lundin et al, *J. Exp. Med.* 178:187-196 (1993)). A T-cell proliferation assay can be performed, for example, by culturing T-cells with irradiated antigen-presenting cells, such as normal spleen cells, in microtiter wells for 3 days with varying concentrations of the BoNT/A fragment to be assayed; adding $^3$H-thymidine; and measuring incorporation of $^3$H-thymidine into DNA.

A tolerogenic fragment of a BoNT/A peptide can be identified using a T-cell cytokine secretion assay known in the art. In such an assay, T cells can be cultured, for example, with irradiated antigen-presenting cells in microtiter wells with varying concentrations of the fragment of interest and, after three days, the culture supernatants can be assayed for IL-2, IL-4 or IFN-γ as described in Czerinsky et al., *Immunol. Rev.* 119:5-22 (1991).

A tolerogenic fragment also can be identified by its ability to induce tolerance in vivo, as indicated by a decreased immunological response, which can be a decreased T-cell response, such as a decreased proliferative response or cytokine secretion response as described above, or a decreased antibody titer to the antigen. A neonatal or adult mouse can be tolerized with a fragment of a BoNT/A peptide, and a T-cell response or anti-BoNT/A antibody titer can be assayed after challenging by immunization. As an example, a neonatal mouse can be tolerized within 48 hours of birth by intraperitoneal administration of about 100 μg of a fragment of a BoNT/A peptide emulsified with incomplete Freund's adjuvant and subsequently immunized with BoNT/A toxin at about 8 weeks of age (see, for example, Miyahara, supra, 1995). An adult mouse can be tolerized intravenously with about 0.33 mg of a fragment of a BoNT/A peptide, administered daily for three days (total dose 1 mg), and immunized one week later with BoNT/A. A decreased T-cell response, such as decreased proliferation or cytokine secretion, which indicates tolerogenic activity, can be measured using T-cells harvested 10 days after immunization. In addition, a decreased anti-BoNT/A antibody titer, which also indicates tolerogenic activity, can be assayed using blood harvested 4-8 weeks after immunization. Methods for assaying a T-cell response or anti-BoNT/A antibody titer are described above and are well known in the art.

Several well-accepted models of botulinum toxicity can be useful in identifying a tolerogenic fragment of a BoNT/A peptide. Such models include, without limitation, rodent, rabbit and monkey models of foodborne botulism, rodent and chicken models of infant botulism and rodent models of wound botulism, which are described, for example, in Simpson (Ed.) *Botulinum Neurotoxin and Tetanus Toxin* Academic Press, Inc., San Diego, Calif. (1989). The skilled person understands that these and a variety of other well known in vitro and in vivo assays can be useful for identifying a tolerogenic fragment of a BoNT/A peptide.

Preventing or Reducing Immunoresistance to BoNT Therapy

The BoNT/A peptides of the invention also can be useful for preventing or reducing development of a BoNT-specific immune response in an individual, which in turn can prevent or reduce immunoresistance to botulinum toxin therapy. Thus, the present invention provides a method of preventing or reducing immunoresistance to botulinum toxin therapy in an individual by administering to the individual a tolerogizing agent and a BoNT/A peptide having a length of at most 60 amino acids and containing the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant or immunoreactive fragment thereof, thereby preventing or reducing immunoresistance to botulinum toxin therapy, with the proviso that the BoNT/A peptide is not SEQ ID NO:2.

BoNT/A peptides useful for preventing or reducing immunoresistance to botulinum toxin therapy according to a method of the invention can have, for example, a length of at most 40 amino acids or a length of at most 25 amino acids. In one embodiment, a BoNT/A peptide useful for preventing or reducing immunoresistance includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant thereof. In another embodiment, a BoNT/A peptide useful for preventing or reducing immunoresistance includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or an immunoreactive fragment thereof, with the proviso that the BoNT/A peptide is not SEQ ID NO:2. In a further embodiment, a BoNT/A peptide useful for preventing or reducing immunoresistance includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1. In still a further embodiment, a BoNT/A peptide useful for preventing or reducing immunoresistance has the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1. In a further embodiment, a method of the invention is practiced by administering the tolerogizing agent and BoNT/A peptide prior to the individual receiving botulinum toxin therapy. Such an individual can be, for example, an individual at increased risk for developing immunoresistance to botulinum toxin therapy.

The present invention further provides a method of preventing or reducing immunoresistance to botulinum toxin therapy in an individual by administering to the individual a tolerogizing agent and two or more of the following amino acid sequences: 785-803 of SEQ ID NO: 1 [N25]; 981-999 of SEQ ID NO: 1 [C10]; 1051-1069 of SEQ ID NO: 1 [C15]; 1121-1139 of SEQ ID NO: 1 [C20]; and 1275-1296 of SEQ ID NO: 1 [C31], or a conservative variant or an immunoreactive fragment of any of these sequences, thereby preventing or reducing immunoresistance to botulinum toxin therapy. In one embodiment, one of the amino acid sequence includes residues 785-803 of SEQ ID NO: 1 [N25] or a conservative variant or immunoreactive fragment of this sequence. In another embodiment, a method of the invention is practiced by administering to the individual a tolerogizing agent and the following two amino acid sequences: 785-803 of SEQ ID NO: 1 [N25]; and 981-999 of SEQ ID NO: 1 [C10], or a conservative variant or immunoreactive fragment of any of these sequences. In a further embodiment, a method of the invention is practiced by administering to the individual a tolerogizing agent and the following three amino acid sequences: 785-803 of SEQ ID NO: 1 [N25]; 981-999 of SEQ ID NO: 1 [C10]; and 1051-1069 of SEQ ID NO: 1 [C15], or a conservative variant or an immunoreactive fragment of any of these sequences. Again, the two or more amino acid sequences can be provided separately or as part of a compound molecule such as a chimeric synthetic peptide. The methods of the invention an be useful for preventing or reducing immunoresistance to any of a variety of botulinum toxin therapies including, but not limited to, BoNT/A therapy.

A tolerogizing agent and BoNT/A peptide can be administered to an individual prior to administering botulinum toxin therapy to prevent the development of immunoresistance, during a course of botulinum toxin therapy, or after onset of immunoresistance, for example, when symptoms of resistance are first apparent. In addition, a tolerogizing agent and BoNT/A peptide can be administered to an individual who is at increased risk for immunoresistance to botulinum toxin therapy. Those skilled in the art will be able to determine an appropriate candidate for receiving a tolerogizing composition of the invention based on, for example, the particular condition to be treated and the presence or likelihood of symptoms of immunoresistance.

A tolerogizing agent and BoNT/A peptide can be formulated in a variety of pharmaceutically acceptable media, described below. An effective dose of a BoNT/A peptide of the invention for inducing tolerance in an individual will depend upon the particular BoNT/A peptide selected, the tolerogizing agent used, the route administration, and the particular characteristics of the individual, such as age, weight, general health and the like. An effective dose can be determined in an animal model, such as one of those described hereinabove, prior to administration to humans.

Tolerogizing agents and BoNT/A peptides useful in the invention can be administered by a variety of routes to stimulate an immune response. As a non-limiting example, oral tolerance is well-recognized in the art (see, for example, Weiner, *Hospital Practice*, pp. 53-58 (Sep. 15, 1995)).

BoNT/A Peptide Vaccines

The present invention further provides vaccine compositions containing an adjuvant and a BoNT/A peptide of the invention. In particular, the invention provides a vaccine composition that contains an adjuvant and a BoNT/A peptide having a length of at most 60 amino acids and including the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant or immunoreactive fragment thereof, with the proviso that the BoNT/A peptide is not SEQ ID NO:2. In one embodiment, the BoNT/A peptide includes the amino acid sequence 515-541 of SEQ ID NO:1, 529-555 of SEQ ID NO:1, 543-569 of SEQ ID NO:1, 585-611 of SEQ ID NO:1, 655-681 of SEQ ID NO:1, 739-765 of SEQ ID NO:1, 781-807 of SEQ ID NO:1, 809-835 of SEQ ID NO:1, or 823-849 of SEQ ID NO:1, or a conservative variant or immunoreactive fragment thereof, with the proviso that the BoNT/A peptide is not SEQ ID NO:2.

In a vaccine composition of the invention, the BoNT/A peptide can have, for example, a length of at most 40 amino acids or a length of at most 25 amino acids. In one embodiment, the vaccine composition contains a BoNT/A peptide that includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant thereof. In another embodiment, the vaccine composition contains a BoNT/A peptide that includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or an immunoreactive fragment thereof, with the proviso that the BoNT/A peptide is not SEQ ID NO:2. In a further embodiment, the vaccine composition contains a BoNT/A peptide that includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1. In still a further embodiment, the vaccine composition contains a BoNT/A peptide that has the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1.

The vaccines of the invention can be useful, for example, for inducing specific immunity against one or more botulinum toxins such as BoNT/A. Such specific immunity can protect an individual from intoxication produced by exposure to botulinum toxin. As used herein, the term "vaccine" means a composition which, when administered to an individual, stimulates an immune response against an antigen. A vaccine can be useful, for example, for preventing or ameliorating intoxication produced by unwanted exposure to botulinum toxin. Vaccination using peptides has been shown to effectively block the effect of protein toxins. See, for example, Dolimbek et al., *J. Prot. Chem.* 13:490 (1994); Atassi et al., *Mol. Immunol.* 13:927 (1995); and Dolimbek et al., *Mol. Immunol.* 33:681 (1996).

A vaccine of the invention contains one or more BoNT/A peptide antigens. The BoNT/A peptides included in a vaccine of the invention can be selected, for example, depending on immunological factors, such as potency of the peptide in inducing an immune response, and technical factors, such as chemical synthesis yields. A vaccine of the invention also contain one or more adjuvants. The term "adjuvant" as used herein, means a substance that acts generally to accelerate, prolong, or enhance the quality of a specific immune response to a vaccine antigen. An adjuvant can, for example, serve to reduce the number of immunizations or the amount of antigen required for protective immunization. As non-limiting examples, an adjuvant useful in the invention can be an aluminum salt based adjuvant or an immunomodulatory compound such as GM-CSF.

A vaccine of the invention can include a BoNT/A peptide which is, for example, conjugated to, or expressed as a fusion protein with another molecule. The molecule selected for fusion to a BoNT/A peptide will depend on the particular design of the vaccine. Non-limiting examples of BoNT/A fusion proteins useful in the invention include fusions with molecules that increase immune response against the BoNT/A peptide, such as cholera enterotoxin A2 and other peptides against which an immune response is desired, such as another BoNT peptide. In one embodiment, a vaccine of the invention contains a BoNT/A peptide fused to a peptide or protein adjuvant.

Method for Vaccinating an Individual Against BoNT

A vaccine of the invention can stimulate an immune response against botulinum toxin in an individual, resulting in the production of antibodies that bind to and neutralize botulinum toxin. Such an immune response increases the ability of an individual's immune system to destroy botulinum toxin and thereby prevent harmful effects of botulinum toxin exposure.

Thus, the present invention provides a method of vaccinating an individual against botulinum toxin by administering to the individual a vaccine containing an adjuvant and a BoNT/A peptide which has a length of at most 60 amino acids and contains the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant or immunoreactive fragment thereof, thereby producing an immune response to botulinum toxin in the individual, with the proviso that the BoNT/A peptide is not SEQ ID NO:2. In one embodiment, a method of the invention is practiced using a BoNT/A peptide that contains the amino acid sequence 515-541 of SEQ ID NO:1, 529-555 of SEQ ID NO:1, 543-569 of SEQ ID NO:1, 585-611 of SEQ ID NO:1, 655-681 of SEQ ID NO:1, 739-765 of SEQ ID NO:1, 781-807 of SEQ ID NO:1, 809-835 of SEQ ID NO:1, or 823-849 of SEQ ID NO:1, or a conservative variant or immunoreactive fragment thereof, with the proviso that the BoNT/A peptide is not SEQ ID NO:2.

BoNT/A peptides useful for vaccinating an individual against botulinum toxin according to a method of the invention can have, for example, a length of at most 40 amino acids or a length of at most 25 amino acids. In one embodiment, the BoNT/A peptide includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant thereof. In another embodiment, the BoNT/A peptide includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or an immunoreactive fragment thereof, with the proviso that the BoNT/A peptide is not SEQ ID NO:2. In a further embodiment, the BoNT/A peptide includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1. In still a further embodiment, the BoNT/A peptide has the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1.

Further provided herein are methods of vaccinating an individual against botulinum toxin by administering to the individual a vaccine containing an adjuvant and two or more of the following amino acid sequences: 785-803 of SEQ ID NO: 1 [N25]; 981-999 of SEQ ID NO: 1 [C10]; 1051-1069 of SEQ ID NO: 1 [C15]; 1121-1139 of SEQ ID NO: 1 [C20]; and 1275-1296 of SEQ ID NO: 1 [C31], or a conservative variant or an immunoreactive fragment of one of these sequences, thereby producing an immune response to the botulinum toxin in the individual. In one embodiment, one of the amino acid sequence includes residues 785-803 of SEQ ID NO: 1 [N25] or a conservative variant or immunoreactive fragment of this sequence. In another embodiment, the vaccine includes an adjuvant and the following two amino acid sequences: 785-803 of SEQ ID NO: 1 [N25]; and 981-999 of SEQ ID NO: 1 [C10], or a conservative variant or immunoreactive fragment of any of these sequences. In a further embodiment, the vaccine includes an adjuvant and the following three amino acid sequences: 785-803 of SEQ ID NO: 1 [N25]; 981-999 of SEQ ID NO: 1 [C10]; and 1051-1069 of SEQ ID NO: 1 [C15], or a conservative variant or an immunoreactive fragment of any of these sequences. As for the methods disclosed above, the two or more amino acid sequences can be provided separately or as part of a compound molecule such as a chimeric synthetic peptide.

Thus, the present invention provides a method of removing botulinum toxin blocking antibodies from a patient by removing blood from a patient; contacting the blood, or an antibody-containing component thereof, with two or more of the following amino acid sequences: 785-803 of SEQ ID NO: 1 [N25]; 981-999 of SEQ ID NO: 1 [C10]; 1051-1069 of SEQ ID NO: 1 [C15]; 1121-1139 of SEQ ID NO: 1 [C20]; and 1275-1296 of SEQ ID NO: 1 [C31], or a conservative variant or an immunoreactive fragment thereof, under conditions suitable for forming a complex of each of the amino acid sequences and anti-botulinum toxin antibody; and removing the complex from the blood or antibody-containing component thereof. In one embodiment, patient blood, or an antibody-containing component thereof, is contacted with the following two amino acid sequences: 785-803 of SEQ ID NO: 1 [N25]; and 981-999 of SEQ ID NO: 1 [C10], or a conservative variant or an immunoreactive fragment of any of these sequences. In another embodiment, patient blood, or an antibody-containing component thereof, is contacted with the following three amino acid sequences: 785-803 of SEQ ID NO: 1 [N25]; 981-999 of SEQ ID NO: 1 [C10]; and 1051-1069 of SEQ ID NO: 1 [C15], or a conservative variant or an immunoreactive fragment of one of these sequences. It is understood that any of the above methods of removing botulinum toxin blocking antibodies from a patient can be practiced by selectively removing IgG anti-botulinum toxin antibodies. It is further understood that the two or more amino acid sequences can be provided separately or as part of a compound molecule such as a chimeric synthetic peptide.

A vaccine useful in a method of the invention can be administered by any of a variety of routes, as described below in relation to pharmaceutical compositions. Those skilled in the art can readily determine for a particular BoNT/A vaccine, the appropriate antigen payload; route of immunization; volume of dose; and vaccination regimen useful in a particular animal, for example, humans.

One skilled in the art can determine if a BoNT/A vaccine induces an immune response, as methods for detecting immune responses are well known in the art. Non-limiting examples involve measuring the titer of BoNT/A-selective antibodies in an animal primed with the vaccine and boosted with the antigen, or determining the presence of antibodies in the blood of an immunized animal that are cross-reactive with the antigen by ELISA, Western blotting or other well-known methods. Cell-mediated immune responses can be determined, for example, by measuring cytotoxic T cell response to antigen using a variety of methods described hereinabove or well known in the art.

BoNT/A Antibodies

A BoNT/A peptide of the invention can be used in a process for preparing an anti-BoNT antibody. Thus, the present invention provides a method of preparing an anti-BoNT/A antibody by administering to an animal a BoNT/A peptide having a length of at most 60 amino acids and containing the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant or immunoreactive fragment thereof; collecting from the animal a sample containing an antibody or antibody-producing cell; and processing the sample to isolate the anti-BoNT/A antibody, with the proviso that the BoNT/A peptide is not SEQ ID NO:2. In one embodiment, a method of the invention is practiced with a BoNT/A peptide containing the amino acid sequence 515-541 of SEQ ID NO:1, 529-555 of SEQ ID NO:1, 543-569 of SEQ ID NO:1, 585-611 of SEQ ID NO:1, 655-681 of SEQ ID NO:1, 739-765 of SEQ ID NO:1, 781-807 of SEQ ID NO:1, 809-835 of SEQ ID NO:1, or 823-849 of SEQ ID NO:1, or a conservative variant or immunoreactive fragment thereof, with the proviso that the BoNT/A peptide is not SEQ ID NO:2.

BoNT/A peptides useful for preparing an anti-BoNT/A antibody can have, for example, a length of at most 40 amino acids or a length of at most 25 amino acids. In one embodiment, a method of the invention is practiced by administering a BoNT/A peptide that includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or a conservative variant thereof. In another embodiment, a method of the invention is practiced by administering a BoNT/A peptide that includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1, or an immunoreactive fragment thereof, with the proviso that the BoNT/A peptide is not SEQ ID NO:2. In a further embodiment, a method of the invention is practiced by administering a BoNT/A peptide that includes the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1. In yet a further embodiment, a method of the invention is practiced by administering a BoNT/A peptide that has the amino acid sequence 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1.

Antibodies to be prepared according to a method of the invention include polyclonal and monoclonal antibodies. A BoNT/A antibody prepared according to a method of the invention, or a monoclonal anti-BoNT/A antibody of the invention as described further below, can be used in a variety of applications. Such applications include, for example, detection of botulinum toxin in a sample, such as a substance suspected to be contaminated with BoNT/A.

As used herein, the term "antibody" includes polyclonal and monoclonal antibodies, as well as polypeptide fragments of antibodies that selectively bind to a BoNT polypeptide. Such selective binding refers to the discriminatory binding of the antibody to the indicated target peptide or polypeptide such that the antibody does not substantially cross react with unrelated peptides or polypeptides. Specific reactivity can include binding properties such as binding specificity, binding affinity and binding avidity. For example, an antibody can bind a target peptide or polypeptide with a binding affinity (Kd) of about $10^{-4}$ M or more, $10^{-6}$ M or more, $10^{-7}$ M or more, $10^{-8}$ M or more, $10^{-9}$ M or more, or $10^{-10}$ M or more. Several methods for detecting or measuring antibody binding are known in the art and disclosed herein. Monoclonal antibodies refer to a population of antibody molecules that contain only one species of antibody capable of binding a particular antigen. Methods of producing a monoclonal antibody are well known (see, for example, Harlow and Lane, supra, 1988). As a non-limiting example, a hybridoma that produces a BoNT/A monoclonal antibody can be identified by screening hybridoma supernatants for the presence of antibodies that bind to a BoNT/A peptide of the invention (Harlow, supra, 1988). For example, hybridoma supernatants can be screened using BoNT/A-positive sera in a radioimmunoassay or enzyme-linked immunosorbent assay. Polyclonal antibodies refer to a population of antibody molecules that contain two or more species of antibody capable of binding to a particular antigen. Methods of producing a polyclonal antibody are well known (see, for example, Harlow and Lane, supra, 1988). As a non-limiting example, serum from an animal immunized with a BoNT/A peptide of the invention can be screened in a radioimmunoassay or enzyme-linked immunosorbent assay to identify a polyclonal BoNT/A antibody.

A variety of well known methods can be used for collecting from an animal a sample containing an antibody or antibody-producing cell. Such methods are described, for example, in Harlow et al., supra, 1998. Similarly, a variety of well known methods can be used for processing a sample to isolate a anti-BoNT/A antibody. A procedure for collecting an processing a sample can be selected based on the type of antibody to be isolated. As an example, when isolating polyclonal antibodies, an appropriate sample can be a blood sample containing antibodies, whereas when isolating monoclonal antibodies, an appropriate sample can be an antibody-producing cell such as a spleen cell. Exemplary well known procedures for isolating both monoclonal and polyclonal antibodies are known in the art as described above.

Monoclonal anti-BoNT/A antibodies

In another embodiment, the present invention provides an anti-BoNT/A monoclonal antibody having specificity for an epitope contained within one of the following amino acid sequences: amino acids 445-471 of SEQ ID NO:1, 487-513 of SEQ ID NO:1, 515-541 of SEQ ID NO:1, 529-555 of SEQ ID NO:1, 543-569 of SEQ ID NO:1, 557-583 of SEQ ID NO:1, 585-611 of SEQ ID NO:1, 599-625 of SEQ ID NO:1, 655-681 of SEQ ID NO:1, 669-695 of SEQ ID NO:1, 683-709 of SEQ ID NO:1, 711-737 of SEQ ID NO:1, 739-765 of SEQ ID NO:1, 767-793 of SEQ ID NO:1, 781-807 of SEQ ID NO:1, 809-835 of SEQ ID NO:1, 823-849 of SEQ ID NO:1, or 837-863 of SEQ ID NO:1. In a further embodiment, the present invention provides an anti-BoNT/A monoclonal antibody having specificity for an epitope contained within one of the following amino acid sequences: amino acids 515-541 of SEQ ID NO:1, 529-555 of SEQ ID NO:1, 543-569 of SEQ ID NO:1, 585-611 of SEQ ID NO:1, 655-681 of SEQ ID NO:1, 739-765 of SEQ ID NO:1, 781-807 of SEQ ID NO:1, 809-835 of SEQ ID NO:1, or 823-849 of SEQ ID NO:1. In yet a further embodiment, the present invention provides an anti-BoNT/A monoclonal antibody having specificity for an epitope contained within amino acids 785-803 of SEQ ID NO: 1, which correspond to the epitope defined within the N25 peptide. In still further embodiments, any of the monoclonal antibodies disclosed above are of the IgG subtype. As used herein, the term "monoclonal antibody" means a homogeneous population of antibody species. By definition, a monoclonal antibody binds to a single epitope.

Treatment of Botulinum Toxicity

A BoNT/A antibody prepared according to a method of the invention can bind to a botulinum toxin and neutralize its effects. Thus, the present invention provides a method of treating botulinum toxicity in an individual by administering to the individual a pharmaceutical composition containing an anti-BoNT/A antibody produced according to a method of the invention or an anti-BoNT/A monoclonal antibody of the invention. Botulinum toxicity refers to intoxication resulting from exposure to botulinum toxin. Botulism clinical syndromes include food borne botulism, which can result from ingestion of preformed botulinum toxin in contaminated foods; wound botulism, which can result from the production of botulinum toxin in vivo after growth of *C. botulinum* in an infected wound; GI colonization syndromes, which can result from the production of botulinum toxin in vivo due after growth of *C. botulinum* in the intestinal tract of a colonized individual; iatrogenic botulism, which can result from injection of botulinum toxin into a tissue of an individual; and inhalation botulism, which can occur accidentally in humans, for example, in a veterinary setting when working with infected animals, and as a result of biological warfare. The signs and symptoms of botulinum intoxication are well known to those skilled in the art.

Experiments performed in vivo and in vitro have indicated that antibodies can enter cholinergic nerves and neutralize internalized BoNT (Simpson, *J. Physiol. Paris* 84:143 (1990)). As such, anti-BoNT antibodies can act, for example, extracellularly by interfering with the binding of BoNT to the cell surface and intracellularly by interfering with BoNT enzymatic activity. The ability of an anti-BoNT/A antibody prepared according to a method of the invention to neutralize the effects of botulinum toxicity on an individual, and, thus, "protect against" botulinum toxicity, can be determined in an animal model using a variety of methods well known to those skilled in the art. Exemplary animal models of botulism include rodent, rabbit and monkey models of foodborne botulism, rodent and chicken models of infant botulism and rodent models of wound botulism, all of which are described, for example, in Simpson, supra, 1989.

Plasmapheresis

The BoNT/A peptides disclosed herein also can be useful for therapeutic immunoadsorption for extracorporeal removal of anti-botulinum toxin antibodies. Such therapeutic immunoadsorption is well known in the art. In general, blood can be removed from a patient to be treated or having been treated with a botulinum toxin therapeutic such as BOTOX®; and anti-botulinum toxin antibodies subsequently removed from the blood, serum or plasma using affinity chromatography with one or more BoNT/A peptides of the invention are attached to a biocompatible support. In one embodiment, an N25 BoNT/A peptide is used for therapeutic immunoadsorption such that anti-N25 antibodies are removed from patient blood, serum or plasma. In another embodiment, one or a combination of N25, C10, C15, C20 or C31 BoNT/A peptides are used for therapeutic immunoadsorption such that antibodies to epitopes in the peptides used for the immunoadsorption are removed from patient blood, serum or plasma.

Thus, the present invention provides a method of removing botulinum toxin blocking antibodies from a patient by removing blood from a patient; contacting the blood, or an antibody-containing component thereof, with two or more of the following amino acid sequences: 785-803 of SEQ ID NO: 1 [N25]; 981-999 of SEQ ID NO: 1 [C10]; 1051-1069 of SEQ ID NO: 1 [C15]; 1121-1139 of SEQ ID NO: 1 [C20]; and 1275-1296 of SEQ ID NO: 1 [C31], or a conservative variant or an immunoreactive fragment thereof, under conditions suitable for forming a complex of each of the amino acid sequences and anti-botulinum toxin antibody; and removing the complex from the blood or antibody-containing component thereof. In one embodiment, patient blood, or an antibody-containing component thereof, is contacted with the following two amino acid sequences: 785-803 of SEQ ID NO: 1 [N25]; and 981-999 of SEQ ID NO: 1 [C10], or a conservative variant or an immunoreactive fragment of any of these sequences. In another embodiment, patient blood, or an antibody-containing component thereof, is contacted with the following three amino acid sequences: 785-803 of SEQ ID NO: 1 [N25]; 981-999 of SEQ ID NO: 1 [C10]; and 1051-1069 of SEQ ID NO: 1 [C15], or a conservative variant or an immunoreactive fragment of one of these sequences. It is understood that any of the above methods of removing botulinum toxin blocking antibodies from a patient can be practiced by selectively removing IgG anti-botulinum toxin antibodies. It is further understood that the two or more amino acid sequences can be provided separately or as part of a compound molecule such as a chimeric synthetic peptide.

Biocompatible solid supports having combinations of two or more BoNT/A peptides can be useful in plasma or other pheresis, or pheresis can be performed using a series of affinity columns or other solid supports each having a different BoNT/A peptide. It is understood that the blood, serum or plasma are contacted with the one or more BoNT/A peptides attached to a biocompatible solid support under conditions that promote binding between the one or more BoNT/A peptides and anti-botulinum toxin antibodies in the patient fluid. As an example, extracorporeal hemoperfusion can be performed as described in U.S. Pat. No. 5,149,425. Such conditions can include, without limitation, contact temperatures in the range of 35° C. and 40° C., and contact times of about one to six hours. It is understood that the unbound portion of the blood, plasma, or serum, which is significantly antibody-depleted, is reintegrated with cellular components of whole blood as necessary and reintroduced into the patient on a continuous basis or following collection. One skilled in the art further understands that, if desired, the antibody-depleted blood, plasma or serum can be assayed prior to reintroduction in the patient, for example, using one of the BoNT/A peptide binding assays or protection assays disclosed herein, Several techniques can be useful for removing anti-botulinum toxin blocking antibodies complexed with a BoNT/A peptide. As an example, a solid phase system can utilize a solid phase matrix which is a solid phrase support to which the one or more BoNT/A peptides are bound. The blood, plasma or serum containing the blocking antibodies is passed over the solid support, exiting the solid support and leaving behind the blocking antibody/peptide complexes. A variety of biocompatible solid supports can be useful in the methods of the invention. Such supports are chemically inert with respect to human antibody-containing fluids, have sufficient binding capacity, and generally are in the form of a continuous large surface such as a sheet or column, or in the form of particles or vesicles. Exemplary solid supports useful in the invention, including those useful for affinity chromatography, encompass, without limitation, silica; synthetic silicates such as porous glass, for example, glass fiber filters; biogenic silicates such as diatomaceous earth; silicate-containing materials such as kaolinite and borosilicate; and synthetic polymers such as polystyrene, polyproplene and polysaccharides (see, for example, U.S. Pat. No. 6,607,723 and U.S. Pat. No. 5,149,425. Biocompatible solid supports useful in the invention further include, yet are not limited to, agarose, which is a neutral linear polysaccharide generally composed of D-galactose and altered 3,6-anhydrogalactose residues, for example, Sepharose (Pharmacia); activated gels, cellulose, nitrocellulose, polyvinylchloride, and diazotized paper. The skilled person understands that these and a variety of other well known biocompatible solid supports can be useful in the methods of the invention.

The one or more BoNT/A peptides can be covalently or noncovalently bound to the solid support using well known methods. Supports which can be non-covalently bound by incubation with the immunosorbent include, without limitation, nitrocellulose, borosilicate, filters, polyvinylchloride, polystyrene and diazotized paper. Activated solid supports such as activated matrices also are well known in the art and commercially available and useful in the invention. Such activated solid supports encompass, without limitation, epoxy-activated agarose; CNBr-activated agarose; 6-aminohexanoic acid and 1,6-diaminohexane-agarose, thiopropyl agarose; carbonyldiimidazole-activated agarose; and aminoethyl and hydrazide-activated polyacrylamide (see, for example, U.S. Pat. Nos. 6,406,861 and 4,762,787).

In one embodiment, the methods of the invention for selectively removing blocking anti-botulinum toxin antibodies are performed using an affinity column. An affinity column is a cylindrical container with filters on both ends which contains a solid support to which the one or more BoNT/A peptides are bound. One skilled in the art understands that plasma or serum generally is passed through a column since whole blood contains cells and particulate matter such as platelets which can impede column flow. In another embodiment, a sheet such as a nitrocellulose sheet is pre-bound with one or more BoNT/A peptides, and blood, plasma or serum is incubated with the immunosorbent-linked nitrocellulose. In a further embodiment, one or more BoNT/A peptides are bound to large polystyrene petri dishes. Blood, plasma or serum from an individual is incubated with the BoNT/A peptide-linked polystyrene and is decanted, leaving behind the blocking antibodies complexed to the one or more BoNT/A peptides.

It is further understood that pre-clearance of antibodies, or a class of antibody such as the IgG class, can be performed prior to selective removal of anti-botulinum toxin antibodies. From the pre-cleared antibody pool, BoNT/A peptide-reactive antibodies can be selected, and the remaining antibodies reconstituted into the blood to be reperfused into the individual, thus reducing the volume to be passed over the blocking antibody selective support and also reducing non-specific binding. As a non-limiting example, non-specific Protein G Sepharose columns such as PROSORBA® (IMRE; Munich, Germany) or Ig-THERASORB® (Plasmaselect; Teterow, Germany) can be used to remove a significant portion of IgG antibody. A variety of additional techniques suitable for general pre-clearance of antibodies are well known in the art and include, yet are not limited to, ammonium sulfate precipitation with ion exchange chromatography; caprylic acid; DEAE-matrices (ion-exchange chromatography); hydroxyapatite chromatography, and gel filtration (Sepharose). See, for example, Harlow and Lane, supra, 1998.

In still a further embodiment, one or more BoNT/A peptides are bound to lipid vesicles, and the lipid vesicle-immunosorbent is mixed with a patient's plasma or serum to allow binding to the blocking antibodies. The plasma or serum is subsequently filtered to remove the lipid vesicle-immunosorbent-antibody complex. See, for example, U.S. Pat. No. 4,643,718.

One skilled in the art further understands that one or more BoNT/A peptides of the invention can be used for liquid phase separation of blocking antibodies from patient blood, plasma or serum. Liquid phase separation can be performed, for example, by conjugating one or more BoNT/A peptides to a hapten such as, without limitation, dinitrophenol or fluorescein. After mixing the hapten/BoNT/A peptide conjugate with a patient's blood, plasma or serum, the conjugate forms complexes with anti-botulinum toxin blocking antibodies. As a non-limiting example, such antibody complexes can be precipitated using polyethylene glycol (PEG), and the precipitated complexes separated from the blood, plasma or serum using centrifugation (see, for example, U.S. Pat. No. 4,551,435). One skilled in the art appreciates that these and other solid-phase and liquid-phase systems can be used to separate BoNT/A peptide/blocking antibody complexes from patient blood, plasma or serum.

Blocking Neutralizing Antibodies In Situ

As disclosed herein in Example IX and discussed above, one or more of the synthetic peptides N25, C10, N15, N20 or N31 binds protective antibodies in the large majority of protective patient sera in a sample of 28 cervical dystonia patients treated with BOTOX® and having MPA-protective sera. Based on this finding, one or more of the BoNT/A peptides N25, C10, N15, N20 or N31, or a conservative variant or immunoreactive fragment thereof, can be useful for decreasing patient non-responsiveness when administered in excess together with a therapeutic botulinum toxin preparation.

Increased IgG Levels

The present invention additionally provides a method of predicting or determining immunoresistance to botulinum toxin therapy in an individual by determining the level of IgG antibodies immunoreactive with the botulinum toxin in the individual; and comparing the level of IgG antibodies to a control level of IgG antibodies, where an increase in the level of IgG antibodies in the individual as compared to the control level indicates immunoresistance to the botulinum toxin therapy. Such an increase can be, for example, at least a 5-fold increase or at least a 10-fold increase. In one embodiment, the control level of IgG antibodies is determined in an individual who has not been treated with botulinum toxin therapy. In another embodiment, the control level of IgG antibodies is determined in an individual who is responsive to the botulinum toxin therapy. The methods of the invention can be used to predict or determine immunoresistance to any of several botulinum toxin therapies including, without limitation, BoNT/A therapy.

Techniques for determining a level of IgG antibodies immunoreactive with a botulinum toxin such as BoNT/A are well known in the art and are described herein. For example, Example VIII describes a solid-phase radioimmunoassay for IgG anti-BoNT/A antibodies using an anti-mouse IgG secondary antibody. A variety of additional anti-IgG antibodies, including anti-human IgG antibodies, are well known in the art and are commercially available, including, but not limited to, rabbit anti-human IgG from Bethyl Laboratories, Inc. (Montgomery, Tex.) and goat anti-human IgG from Zymed Laboratories, Inc (San Francisco, Calif.). Thus, the methods of the invention can be practiced using any of the immunoassays described hereinabove or well known in the art which are specific for detection of IgG antibodies, for example, through use of an anti-IgG secondary antibody.

Pharmaceutical Compositions

A vaccine composition containing a BoNT/A peptide, tolerogenic composition containing a BoNT/A peptide, or a BoNT/A antibody of the invention can be prepared as a pharmaceutical composition for use in a therapeutic method of the invention. A pharmaceutical composition can include an excipient well known in the art for preparing pharmaceutical compositions, including compositions suitable for intranasal and oral administration. A pharmaceutical composition includes a pharmaceutically acceptable carrier, which is any carrier that has substantially no long term or permanent detrimental effect when administered. Examples of pharmaceutically acceptable carriers include, without limitation, water, such as distilled or deionized water; saline; and other aqueous media. It is understood that the active ingredients can be soluble or can be delivered as a suspension in a suitable carrier.

A preservative or tonicity adjustor can be included, if desired, in a pharmaceutical composition useful in the invention. Useful preservatives include, without limitation, benzalkonium chloride, chlorobutanol, thimerosal, phenylmercuric acetate, and phenylmercuric nitrate. Tonicity adjustors useful in the invention include salts such as sodium chloride, potassium chloride, mannitol or glycerin and other pharmaceutically acceptable tonicity adjustor.

Various buffers and means for adjusting pH can be used to prepare a pharmaceutical composition useful in the invention, provided that the resulting preparation is pharmaceutically acceptable. Such buffers include, without limitation, acetate buffers, citrate buffers, phosphate buffers and borate buffers. It is understood that acids or bases can be used to adjust the pH of the composition as needed. Pharmaceutically acceptable antioxidants useful in the invention include, yet are not limited to, sodium metabisulfite, sodium thiosulfate, acetylcysteine, butylated hydroxyanisole and butylated hydroxytoluene.

A variety of routes of administration can be useful in the invention depending, in part, on the size and characteristics of the BoNT/A peptide, tolerogenic composition, vaccine composition, or antibody to be administered and the history, risk factors and symptoms of the subject to be treated. Routes of administration suitable for the methods of the invention include both systemic and local administration.

Exemplary routes of administration useful in the methods of the invention encompass, without limitation, oral delivery; intravenous injection; intramuscular injection; subcutaneous injection; intraperitoneal injection; transdermal diffusion and electrophoresis; topical eye drops and ointments; periocular and intraocular injection including subconjunctival injection; extended release delivery devices including locally implanted extended release devices including a bioerodible or reservoir-based implants. It is understood that an implant useful in the invention generally releases the implanted pharmaceutical composition over an extended period of time.

It is understood that modifications that do not substantially affect the activity of the various embodiments of this invention are also included within the definition of the invention provided herein. Accordingly, the following examples are intended to illustrate but not limit the present invention.

Example I

Mapping of Human Anti-Pentavalent Botulinum Toxoid Antibodies Using BoNT/A Synthetic Peptides This example shows antigenic mapping of botulinum toxin A with human anti-BoNT antisera using 29 BoNT/A synthetic peptides that encompass the $H_N$ domain of BoNT/A.

Human antisera against BoNT/A were prepared by immunizing human volunteers with a toxoid preparation made from BoNTs A, B, C, D and E as described in Atassi et al. supra, 1996. The binding assays described below were performed using IgG fractions of these antisera. For use as a control, an IgG fraction was prepared using pre-immune human serum.

For use in antigenic mapping, BoNT/A peptides were synthesized, purified and subjected to amino acid analysis by the procedure previously reported (Atassi et al., *Proc. Natl. Acad. Sci. USA* 88:3613 (1991)). Each peptide was found to have an amino acid composition consistent with that expected from its covalent structure shown in FIG. 1. BoNTs A and B were purchased from Metabiologics (Madison, Wis.).

BoNT/A peptides (2.5 μg in 50 μl of PBS) or active BoNT/A (1 μg in 50 μl PBS) were added to the wells of flexible polyvinyl chloride 96-well plates (Becton Dickinson; San Jose, Calif.) and allowed to bind for 18 hours at 4° C. After washing five times with PBS, the plates were blocked for 1 hour at 37° C. with 1% bovine serum albumin (BSA) in PBS. Aliquots (50 μl) of anti-toxin antisera that had been prediluted with 0.1% BSA in PBS (dilutions were human IgG fraction, 1:1000 and 1:2000 (vol/vol)) were pipetted into the appropriate wells and kept at 4° C. for 20 hours. The wells were washed five times with PBS before adding 50 μl of affinity-purified rabbit Ig against human IgG and IgM (Dako Corporation; Carpinteria, Calif.) diluted 1:1000 with 0.1% BSA in PBS to the wells of the plate, and incubating for 2 hours at 37° C.

The wells were then washed five times with PBS, and 50 μl of $^{125}$I-labeled Protein A ($2 \times 10^5$ cpm in 0.1% BSA in PBS) was distributed to the wells and allowed to incubate for 2 hours at room temperature. Finally, the plates were washed thoroughly to remove unbound radioactivity, the individual wells were cut out and transferred into separate tubes, and bound radioactivity was counted in a gamma-counter (1277 Gamma Master; LKB, Finland). Controls included binding of preimmune or normal sera to BoNT/A and its peptides, as well as binding of immune sera to BSA and unrelated peptides. Assays were performed in triplicate. Results of the triplicate analyses were expressed as mean of net cpm Å SD, after correction for nonspecific binding in control wells that were coated with BSA and unrelated peptides.

As shown in FIG. 2, human anti-BoNT antisera were observed to bind to several BoNT/A peptides. Peptide N25 (785-803) was observed to be immunodominant followed, in decreasing order, by regions N8 (residues 547-565 of SEQ ID NO:1), N22 (residues 743-761 of SEQ ID NO:1), and N16 (residues 659-677 of SEQ ID NO:1). Lower, but reproducible, amounts of antibodies were bound, in decreasing order, by peptides N11 (residues 589-607 of SEQ ID NO:1), N17 (residues 673-691 of SEQ ID NO:1), N20 (residues 715-733 of SEQ ID NO:1), N14 (residues 631-649 of SEQ ID NO:1), N28 (residues 827-845 of SEQ ID NO:1), N27 (residues 813-831 of SEQ ID NO:1), N4 (residues 491-509 of SEQ ID NO:1), N24 (residues 771-789 of SEQ ID NO:1) and N7 (residues 533-551 of SEQ ID NO:1). The remaining $H_N$ peptides bound little or no antibodies. As shown in FIG. 2, human antibodies bound to the $H_C$ peptides C2, C6, C10, C11, C15, C21, C24, C31 (FIG. 2) in agreement with previous studies (Atassi et al., supra, 1996). Human anti-BoNT antisera exhibited no binding to a control peptide corresponding to amino acids 218-231 of BoNT light chain ("L peptide). Nonimmune human IgG did not bind to any peptides, and human anti-BoNT antisera showed no antibody binding to unrelated proteins and peptides. The results define antigenic portions of the $H_N$ domain of BoNT/A.

The three-dimensional structure of BoNT/A reveals the solvent-exposed portions of the primary BoNT/A sequence (Lacy et al. *Nat. Struct. Biol.* 5:898 (1996)). Comparison with the results obtained in the present study revealed that the immunodominant antibody-binding regions reside on surface locations on the H subunit of BoNT/A.

In sum, these results demonstrate that BoNT/A peptides N25, N8, N22, N16, N11, N17, N20, N14, N28, N27, N4, N24, N7, C2, C6, C10, C11, C15, C21, C24, and C31 were recognized by human anti-BoNT antisera.

Example II

Mapping of Mouse Anti-Pentavalent Botulinum Toxoid Antibodies Using BoNT/A Synthetic Peptides This example describes antigenic mapping of BoNT/A with mouse anti-BoNT antisera using 29 BoNT/A synthetic peptides that encompass the $H_N$ domain of BoNT/A.

Mouse anti-BoNT antisera were prepared in outbred ICR mice by subcutaneous immunization with BoNT pentavalent toxoid. Antisera used in these studies were obtained 91 days after the first injection (Atassi et al., supra, 1996). Mice were purchased from the National Cancer Institute, and Jackson Laboratory (Bar Harbor, Me.). For use as controls, non-immune mouse sera were obtained from the animals before immunization.

Peptide binding assays were performed as described in Example I, except that the dilution for antisera of outbred mice was 1:50 and 1:200 (vol/vol). The secondary antibodies (mouse IgG (H+L)+IgM (Mu chain) were obtained from Accurate Chemical & Scientific Corporation (Westbury, N.Y.) and were diluted 1:2000 (vol/vol).

Figure 3:
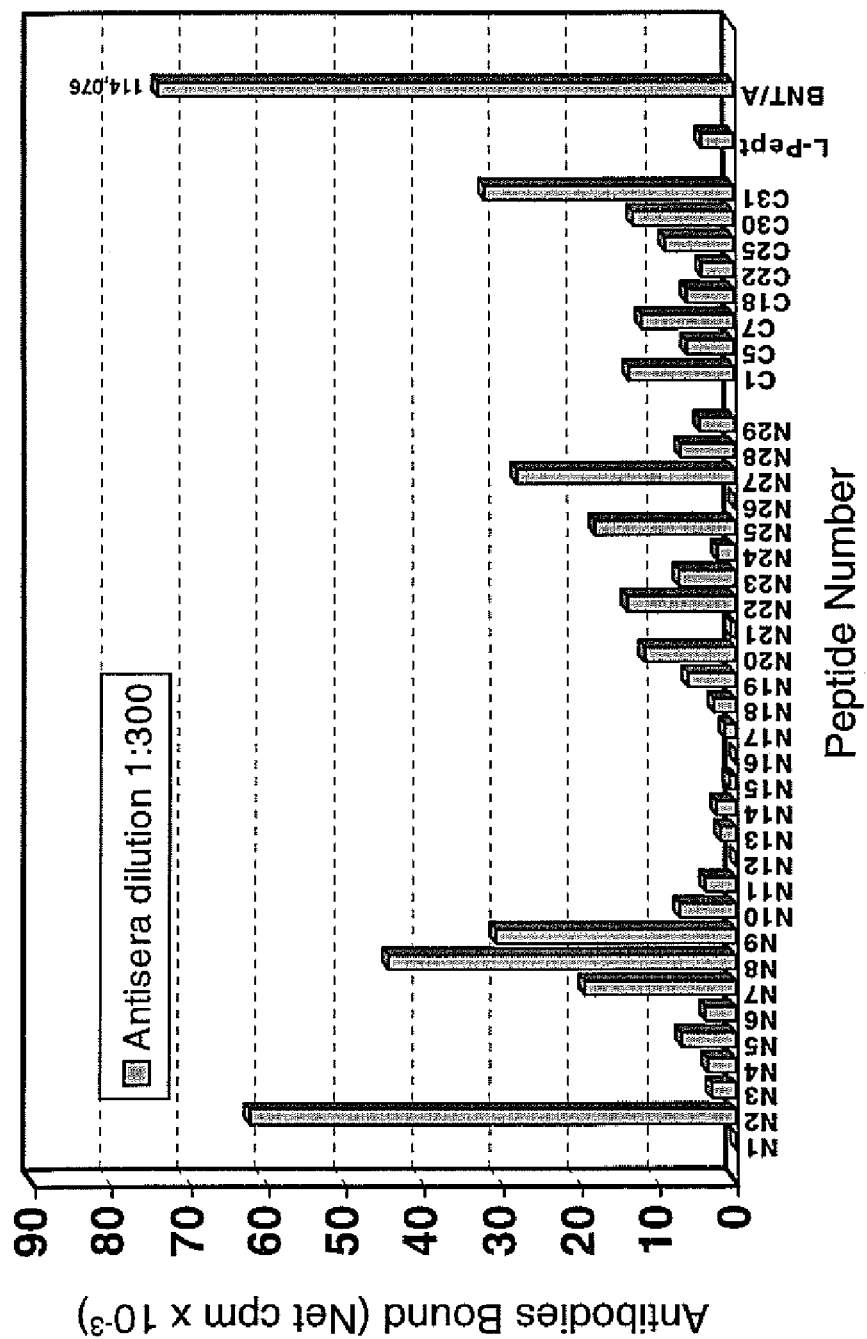
FIG. 3 shows binding of anti-pentavalent botulinum toxoid antibodies of ICR outbred mice to synthetic overlapping peptides spanning the BoNT/A $H_N$ domain. Also shown are binding to L-Peptide and full-length BoNT/A as negative and positive controls, respectively.

As shown in FIG. 3, mouse anti-BoNT antisera were observed to bind to several BoNT/A peptides. At a dilution of 1:50 (vol/vol), peptide N25 (785-803) was immunodominant, followed by one or more regions within the overlap N6/N7/N8/N9 (residues 519-537/533-551/547-565/561-579 of SEQ ID NO:1) and one or more weaker regions within the overlap N27/N28 (residues 813-831/827-845 of SEQ ID NO:1). At a dilution of 1:200 (vol/vol), peptide N25 (residues 785-803 of SEQ ID NO:1) remained immunodominant; in addition, high amounts of antibodies were bound by the overlap N6/N7/N8 (residues 519-537/533-551/547-565 of SEQ ID NO:1), low amounts of antibodies were bound by the overlap N27/N28 (residues 813-831/827-845 of SEQ ID NO:1), indicating that at least one weak epitope resides within this region (See FIG. 3). As shown in FIG. 3, the $H_C$ peptides that possessed antibody binding were C2, C7, C11, C15, C16, C24 and C31, in agreement with previously reported results (Atassi et al., supra, 1996). Mouse anti-BoNT antisera exhibited no binding to a control peptide corresponding to amino acids 218-231 of BoNT light chain ("L peptide"). The mouse anti-BoNT antisera exhibited no antibody binding to unrelated proteins and peptides. Preimmune sera from the same mice did not bind to any of the $H_N$ or $H_C$ peptides.

In sum, these results demonstrate that peptides N25, N6, N7, N8, N9, N27, N28, C2, C7, C11, C15, C16, C24 and C31 were recognized by mouse anti-BoNT antisera.

Example III

Mapping of Chicken BoNT/A Toxoid Antibodies Using BoNT/A Synthetic Peptides

This example describes antigenic mapping of BoNT/A with chicken anti-BoNT antisera using 29 BoNT/A synthetic peptides that encompass the $H_N$ domain of BoNT/A.

Chicken antisera were prepared by monthly subcutaneous injection of formaldehyde-inactivated BoNT/A in Ribi adjuvant. Sera used in this study were obtained after four injections. For use as controls, non-immune chicken sera were obtained from the animals before immunization.

Peptide binding assays were performed as described in Example I, except that the dilution for chicken antisera was 1:500 (vol/vol). The secondary antibodies (rabbit antiserum against chicken IgG) were diluted 1:500 (vol/vol).

TABLE 1

| Peptide No. | Sequence Position (residues of SEQ ID NO: 1) | Human | Horse | Mouse | Chicken |
|---|---|---|---|---|---|
| C1 | 855-873 | − | +++ | ± | − |
| C2 | 869-887 | +++ | − | +++ | +++ |
| C3 | 883-901 | − | + | + | +++++ |
| C4 | 897-915 | − | ± | − | ± |
| C5 | 911-929 | ++ | + | − | + |
| C6 | 925-943 | +++ | − | − | ++ |
| C7 | 939-957 | + | ++ | + | +++++ |
| C8 | 953-971 | − | − | − | − |
| C9 | 967-985 | + | − | ± | ++++ |
| C10 | 981-999 | +++ | ± | − | +++++ |
| C11 | 995-1013 | +++++ | + | + | +++++ |
| C12 | 1009-1027 | − | − | − | + |
| C13 | 1023-1041 | − | + | − | − |
| C14 | 1037-1055 | − | + | − | + |
| C15 | 1051-1069 | +++++ | ± | ++ | +++++ |
| C16 | 1065-1083 | − | − | − | − |
| C17 | 1079-1097 | − | + | − | − |
| C18 | 1093-1111 | − | + | + | ++ |

TABLE 1-continued

| Peptide No. | Sequence Position (residues of SEQ ID NO: 1) | Human | Horse | Mouse | Chicken |
|---|---|---|---|---|---|
| C19 | 1107-1125 | ± | − | − | − |
| C20 | 1121-1139 | + | + | ± | +++++ |
| C21 | 1135-1153 | ++ | ± | ± | +++ |
| C22 | 1149-1167 | ± | + | − | ++ |
| C23 | 1163-1181 | ± | − | − | − |
| C24 | 1177-1195 | +++ | − | ++ | +++++ |
| C25 | 1191-1209 | ± | ++ | − | − |
| C26 | 1205-1223 | − | + | − | − |
| C27 | 1219-1237 | + | − | − | − |
| C28 | 1233-1251 | + | − | − | − |
| C29 | 1247-1265 | ++ | ± | − | ± |
| C30 | 1261-1279 | + | ++ | − | +++ |
| C31 | 1275-1296 | ++ | +++ | ++ | +++ |
| Active BoNT/A | | +++++ | +++++ | +++++ | +++++ |

(+) or (−) signs are based on net cpm values and denote the following:
(−), less than 1,500 cpm;
(Å), 1,500-3,000 cpm;
(+), 3,000-7,000 cpm;
(++), 7,000-15,000 cpm;
(+++), 15,000-25,000 cpm;
(++++), 25,000-35,000 cpm;
(+++++), exceeding 35,000 cpm.

Figure 4:
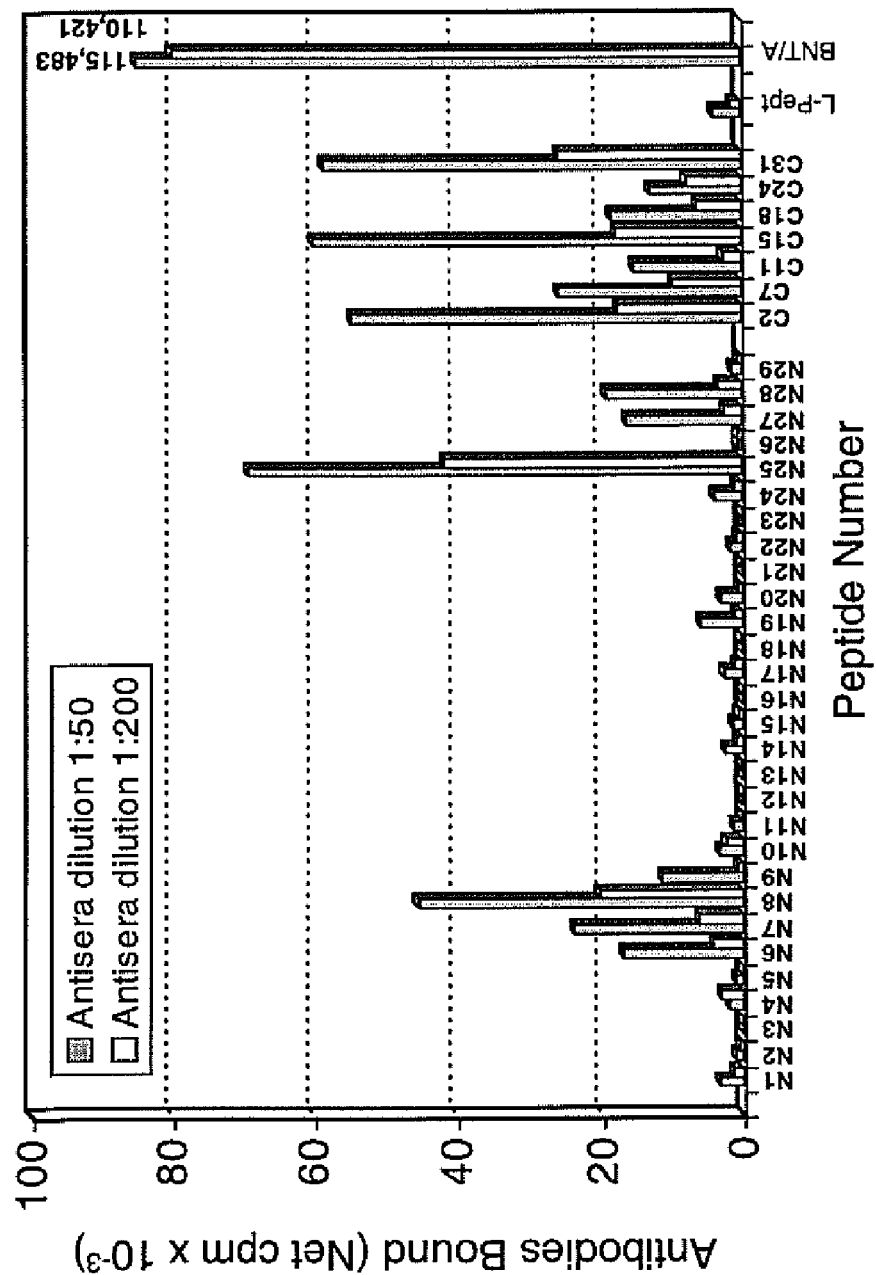
FIG. 4 shows binding of chicken anti-BoNT/A antibodies to 60 synthetic overlapping peptides spanning the entire H-subunit of BoNT/A. Also shown are binding to L-Peptide and full-length BoNT/A as negative and positive controls, respectively.

As shown in FIG. 4, chicken anti-BoNT antisera were observed to bind to several BoNT/A peptides. In particular, peptide N25 (residues 785-803 of SEQ ID NO:1) was the most immunodominant region, followed by N8 (residues 547-565 of SEQ ID NO:1) (FIG. 4). In addition, lower levels of antibodies were directed, in the following decreasing order of antibody level, against peptides N22 (residues 743-761 of SEQ ID NO:1), N27 (residues 813-831 of SEQ ID NO:1), N28 (residues 827-845 of SEQ ID NO:1), N7 (residues 533-551 of SEQ ID NO:1), N6 (residues 519-537 of SEQ ID NO:1), N19 (residues 701-719 of SEQ ID NO:1) and N20 (residues 715-733 of SEQ ID NO:1). The antibody-binding profile of the peptides corresponding to the entire H chain, including the $H_C$ domain is shown in FIG. 4. In the $H_C$ domain, chicken antibodies recognized essentially seven major regions, each of which can contain one or more antigenic sites or epitopes. The regions were located within the peptides C15 (residues 1051-1069 of SEQ ID NO:1) and C24 (1177-1195 of SEQ ID NO:1) and the overlaps C2/C3 (residues 869-887/883-901 of SEQ ID NO:1), C6/C7 (residues 925-943/939-957 of SEQ ID NO:1), C9/C110/C11 (residues 967-985/981-999/995-1013 of SEQ ID NO:1), C20/C21/C22 (residues 1121-1139/1135-1153/1149-1167 of SEQ ID NO:1) and C30/C31 (residues 1261-1279/1275-1296 of SEQ ID NO:1). The chicken antisera showed no antibody binding to unrelated proteins and peptides, and chicken anti-BoNT antisera exhibited no binding to a control peptide corresponding to amino acids 218-231 of BoNT light chain. Preimmune chicken sera bound none of the $H_N$ or $H_C$ peptides. The binding profile of the chicken anti-BoNT/A antibodies to the panel of $H_C$ peptides was similar to that of human antibodies as shown in Table 1.

In sum, these results demonstrate that peptides N25, N8 N22, N27, N28, N7, N6, N19, N20, C15, C24, C2, C3, C6, C7, C9, C10, C1, C20, C21, C22, C30, and C31 were recognized by chicken anti-BoNT antisera.

Example IV

Mapping of Horse BoNT/A Toxoid Antibodies Using BoNT/A Synthetic Peptides

This example describes antigenic mapping of BoNT/A with horse anti-BoNT antisera using 29 BoNT/A synthetic peptides that encompass the $H_N$ domain of BoNT/A.

Horse antisera were prepared by subcutaneous immunization, in multiple sites every two weeks for over a year, with a formaldehyde-inactivated BoNT/A in Ribi adjuvant. The antisera tested in the binding studies were obtained after four injections according to procedures described in Atassi et al., supra, 1996. For use as controls, non-immune horse sera were obtained from the animals before immunization.

Peptide binding assays were performed as described in Example I, except that the dilution for horse antisera was 1:300 (vol/vol). The secondary antibodies were affinity purified rabbit anti-horse IgG obtained from Accurate Chemical & Scientific Corporation (Weston, N.Y.) and were diluted 1:500 (vol/vol).

Figure 5:
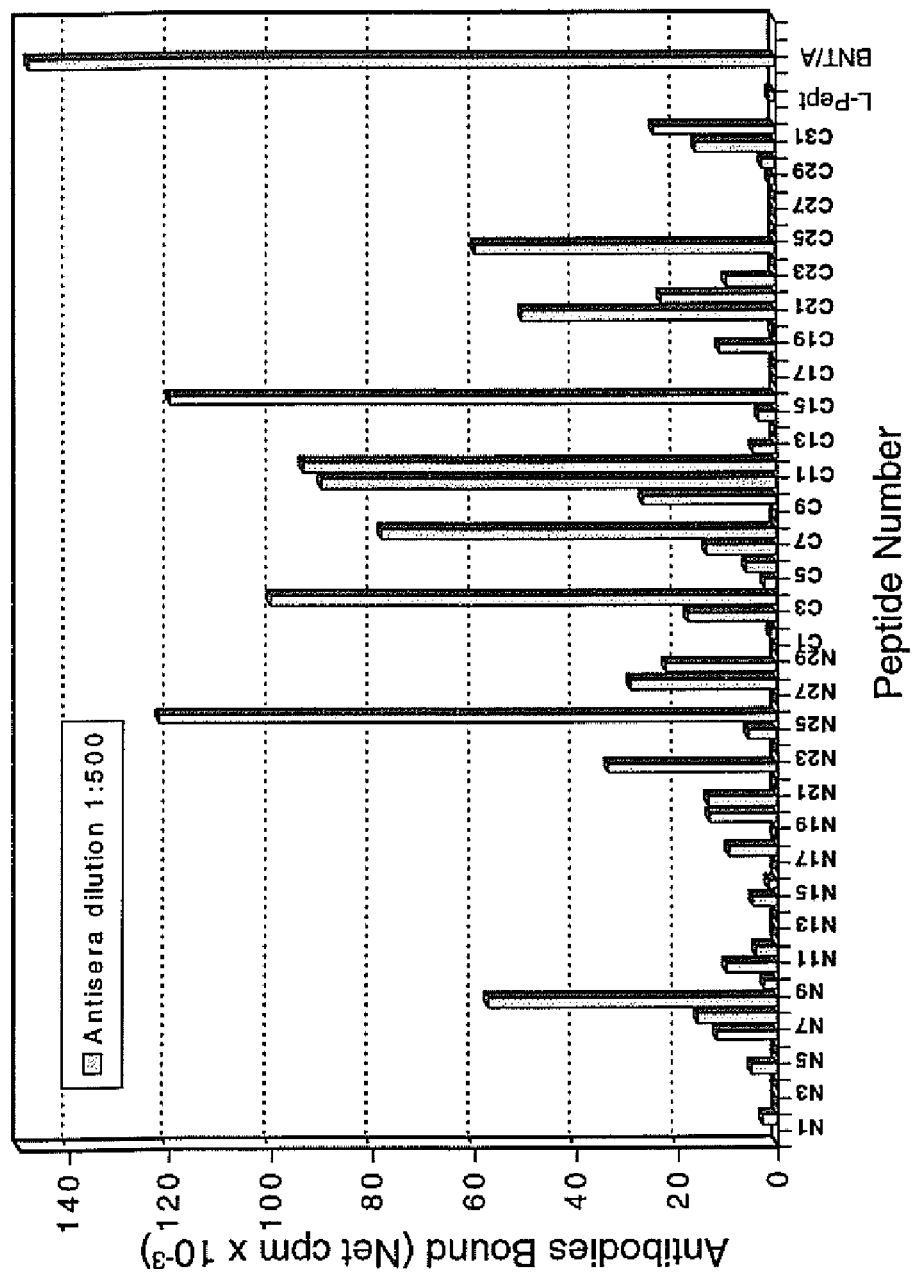
FIG. 5 shows binding of horse anti-BoNT/A antibodies to active BoNT/A overlapping synthetic peptides spanning the BoNT/A $H_N$ domain and to active $H_C$ peptides. Also shown are binding to L-Peptide and full-length BoNT/A as negative and positive controls, respectively.

As with the antisera of human, mouse and chicken as described in Examples I, II and III, one or more regions within the overlapping peptides N7/N8/N9 (residues 533-551/547-565/561-579 of SEQ ID NO:1) were observed to be immunodominant, and peptides N27 (residues 813-831 of SEQ ID NO:1), N25 (residues 785-803 of SEQ ID NO:1), N22 (residues 743-761 of SEQ ID NO:1) and N20 (residues 715-733 of SEQ ID NO:1) possessed binding activity (see FIG. 4). However, horse antibodies exhibited a high level of binding to peptide N2 (residues 463-481 of SEQ ID NO:1), whereas other sera had low levels of binding to peptide N1 (residues 449-467 of SEQ ID NO:1). Therefore, the horse immune response to the BoNT/A region in the vicinity of peptide N2 is shifted to the right by a few residues. The N2 region is also more immunogenic in horse than in human, mouse and chicken. As shown in FIG. 5, horse anti-BoNT antisera were also observed to bind to Hc peptides C1, C5, C7, C18, C22, C25, C30 and C31, in agreement with previous studies (Atassi et al., supra, 1996). Using the horse anti-BoNT antisera, no binding to a control peptide corresponding to amino acids 218-231 of BoNT light chain was observed. The antisera had no binding to unrelated proteins, and preimmune horse sera bound none of the $H_N$ or $H_C$ peptides.

In sum, these results demonstrate that peptides N7, N8, N9, N27, N25, N22, N20, N2, N1, C1, C5, C7, C18, C22, C25, C30 and C31 were recognized by horse anti-BoNT antisera.

Example V

Comparison of BoNT/A Antigenicity Between Human, Mouse, Chicken and Horse

This example defines several common immunogenic regions of BoNT/A by antigen mapping obtained with antisera from four different species.

The results shown in Examples I through IV indicate that antisera against BoNT/A raised in human, horse, mouse and chicken recognize similar immunodominant regions on the $H_N$ domain of BoNT/A. These regions resided, with slight shifts to the left or to the right, within the peptides N6/N7/N8/N9 (residues 519-537/533-551/547-565/561-579 of SEQ ID NO:1) overlap (human, horse and mouse), peptide N22 (residues 743-761 of SEQ ID NO:1) (human, horse and chicken), peptide N25 (residues 785-803 of SEQ ID NO:1) and peptides N27/N28 (residues 813-831/827-845 of SEQ ID NO:1). These results are summarized in Table 2, below.

Whereas peptide N2 was strongly immunodominant with horse antisera, it was unreactive with human, mouse and chicken antisera. However with human, mouse and chicken antisera, peptide N1 reacted weakly and therefore, the reaction of horse antibodies with peptide N2 can represent a shift to the right of the epitope recognized by the horse antibodies. The overlap N16/N17 was highly reactive with human antibodies, whereas with mouse and chicken antisera peptide 17 showed a low level of reactivity. With horse antisera, antibodies against N16/N17 were not detected.

In sum, this example shows that anti-BoNT antibodies from human, mouse, horse and chicken recognize several common immunogenic regions of the BoNT/A $H_N$ domain.

Example VI

Identification of Immunodominant Regions of BoNT/A

This example shows the identification of several immunodominant regions of human anti-BoNT antibodies within the H chain of BoNT/A.

The antigenic regions of BoNT were determined using anti-BoNT antisera obtained from human, mouse, horse and chicken, as shown in Examples I through IV. The location of antigenic regions can be narrowed to shorter domains by the following analysis.

TABLE 2

| Peptide No. | Sequence Position (residues of SEQ ID NO: 1) | Human | Horse | Mouse | Chicken |
|---|---|---|---|---|---|
| L-Peptide | 218-231 | − | − | − | − |
| N1 | 449-467 | ++ | − | + | ± |
| N2 | 463-481 | − | +++++ | − | − |
| N3 | 477-495 | − | ± | − | − |
| N4 | 491-509 | ++ | + | ± | + |
| N5 | 505-523 | − | + | − | − |
| N6 | 519-537 | ++ | + | +++ | ++ |
| N7 | 533-551 | ++ | +++ | +++ | +++ |
| N8 | 547-565 | +++++ | +++++ | +++++ | +++++ |
| N9 | 561-579 | + | ++++ | ++++ | ± |
| N10 | 575-593 | ± | ++ | + | ++ |
| N11 | 589-607 | +++ | + | − | + |
| N12 | 603-621 | + | − | − | − |
| N13 | 617-635 | − | ± | − | − |
| N14 | 631-649 | ++ | ± | ± | + |
| N15 | 645-663 | − | − | − | ± |
| N16 | 659-677 | ++++ | − | − | − |
| N17 | 673-691 | ++ | − | ± | ++ |
| N18 | 687-705 | + | ± | − | − |
| N19 | 701-719 | ± | + | + | ++ |
| N20 | 715-733 | ++ | ++ | ± | ++ |
| N21 | 729-747 | ± | − | − | − |
| N22 | 743-761 | ++++ | ++ | + | ++++ |
| N23 | 757-775 | − | + | − | − |
| N24 | 771-789 | ++ | ± | + | + |
| N25 | 785-803 | +++++ | +++ | +++++ | +++++ |
| N26 | 799-817 | − | − | − | − |
| N27 | 813-831 | ++ | ++++ | +++ | ++++ |
| N28 | 827-845 | ++ | + | +++ | +++ |
| N29 | 841-859 | + | + | − | − |
| Active BoNT/A | | +++++ | +++++ | +++++ | +++++ |

(+) or (−) signs are based on net cpm values and denote the following:
(−), less than 1,500 cpm;
(±), 1,500-3,000 cpm;
(+), 3,000-7,000 cpm;
(++), 7,000-15,000 cpm;
(+++), 15,000-25,000 cpm;
(++++), 25,000-35,000 cpm;
(+++++), exceeding 35,000 cpm.

In this analysis, the size of an antigenic site was assigned to be 10-11 residues. The H-chain of BoNT/A was therefore broken down into 13 antigenic sites. The 13 antigenic sites are defined in Table 3, below. The table gives the approximate locations of only the antigenic regions that bind 15,000 cpm of antibody or greater. Although only the immunodominant regions are shown in Table 3, regions binding lower amounts of antibodies can be of equivalent immunological significance.

In sum, this example shows that BoNT/A immunodominant regions having 10-11 residues can be determined based on reactivity of anti-BoNT antisera obtained from human, mouse, horse and chicken with BoNT/A peptides.

TABLE 3

| Antigenic Regions | Amino Acid Residue of SEQ ID NO: 1 |
|---|---|
| $H_N$ Domain Regions | |
| NR1 | 554-564 |
| NR2 | 593-602 |
| NR3 | 666-676 |
| NR4 | 748-757 |
| NR5 | 785-794 |
| $H_c$ Domain Regions | |
| CR1 | 854-887 |
| CR2 | 933-943 |
| CR3 | 986-995 |
| CR4 | 1000-1009 |
| CR5 | 1056-1065 |
| CR6 | 1137-1147 |
| CR7 | 1183-1192 |
| CR8 | 1276-1289 |

Example VII

Mapping of T- and B-Cell Recognition Profiles of the BoNT/A $H_N$ Domain in Two High-Responder Mouse Strains This example demonstrates that responses to each antibody or T cell epitope are under separate genetic control and that there is partial, but not complete, coincidence between antibody and T cell $H_N$ recognition regions.

A. T Cell Recognition of $H_N$ Peptides After One Injection with Toxoid

Figure 7:
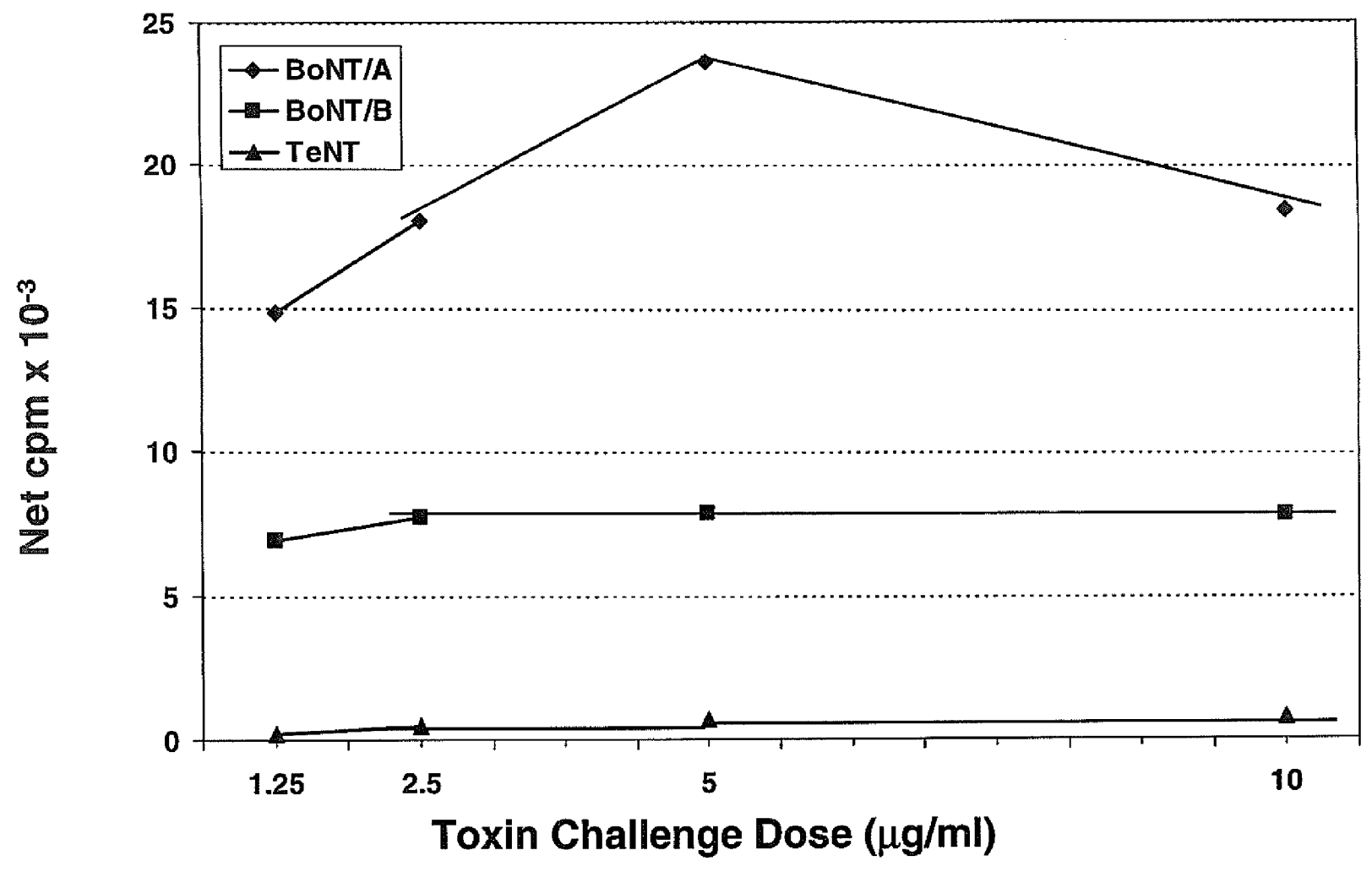
Figure 8:
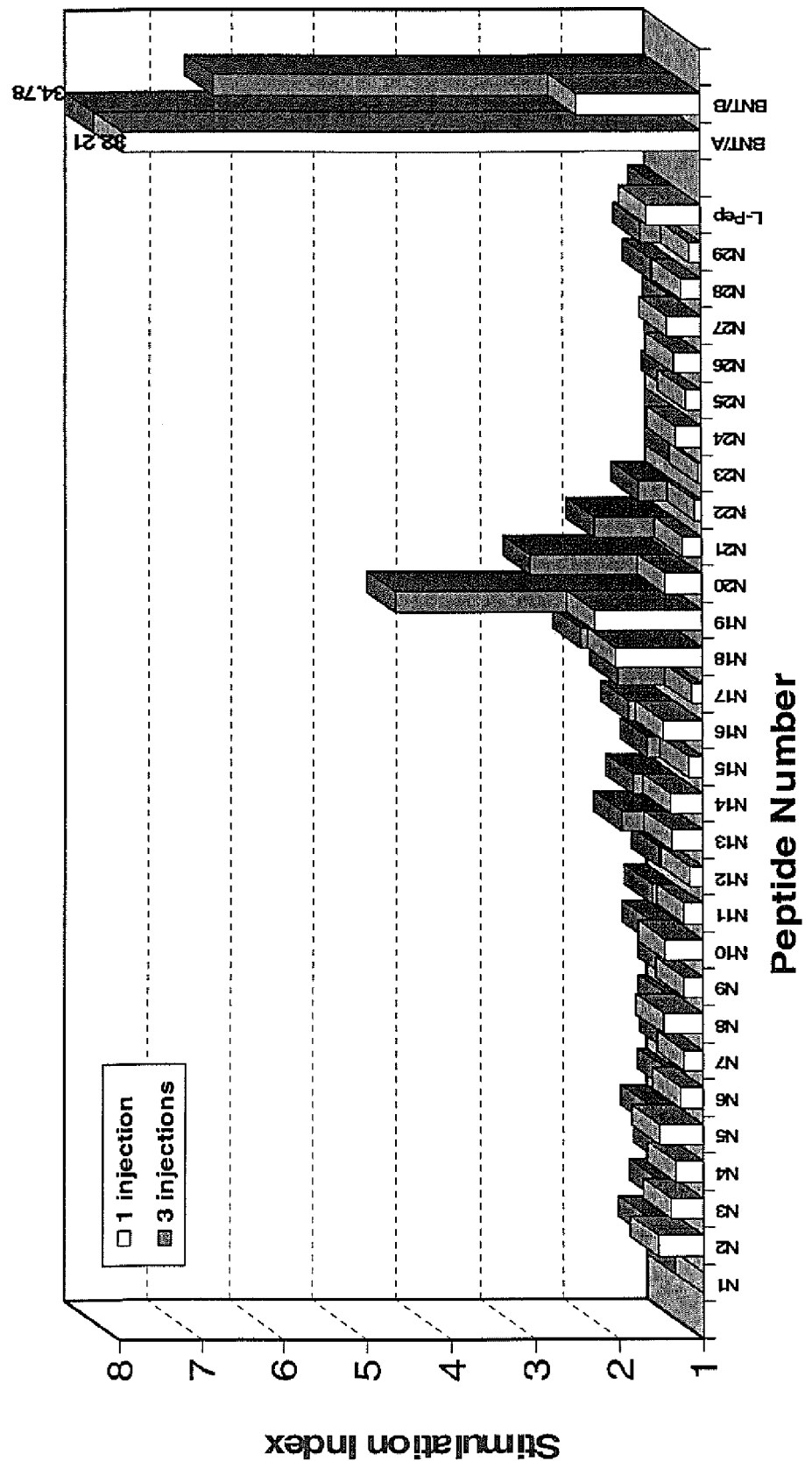
FIG. 8 shows proliferative responses of LNC ($5 \times 10^5$ cells/well) of Balb/c mice after 1 injection or after 3 injections with BoNT/A toxoid (1:g/mouse/injection).

Exemplary proliferative responses of BALB/c lymph node cells (LNCs) were determined at various doses of toxoid as shown in FIG. 7. The response profile to the full panel of $H_N$ peptides spanning the entire N-terminal domain of the BoNT/A heavy chain was subsequently determined. As shown in FIG. 8, BALB/c T cells primed with one injection of BoNT/A toxoid recognized one major region localized within overlap N18/N19 (residues 687-705/701-719 of SEQ ID NO: 1) while the remaining peptides had no detectable stimulating activity in vitro. BoNT/A-primed BALB/c T cells showed substantial cross-reaction with BoNT/B (SI values: BoNT/A 23.62, BoNT/B 7.89) but had no cross-reactivity with TeNT (FIG. 7).

Figure 9:
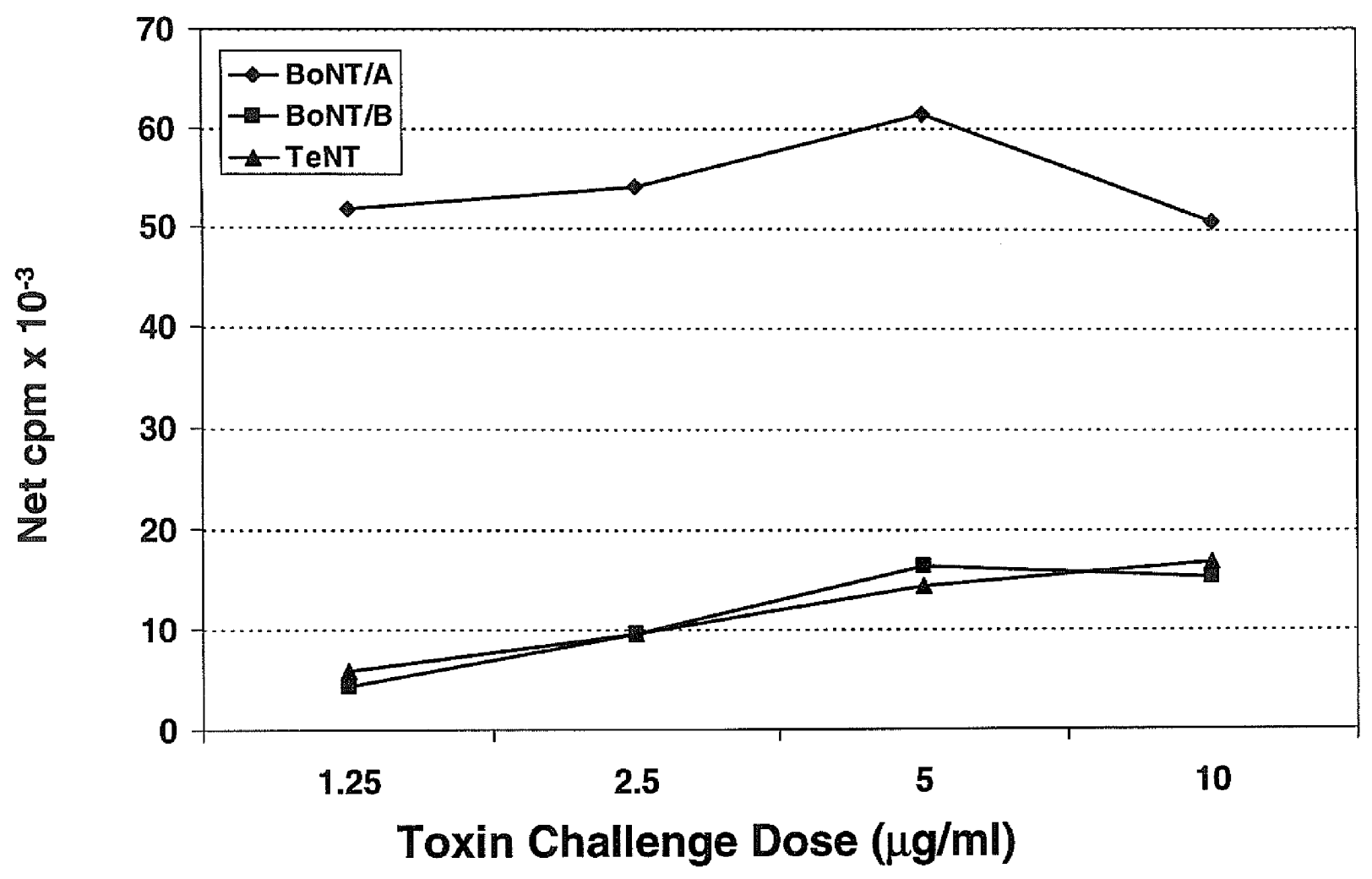

Unlike BALB/c T cells, the T cells from a BoNT/A-primed second inbred strain of mice, SJL/JCr, cross-reacted with both BoNT/B and TeNT (FIG. 9). As summarized in FIG. 10, BoNT/A-primed SJL T cells responded to challenge with a number of the overlapping peptides of $H_N$. In particular, peptides N9 (residues 561-579 of SEQ ID NO: 1), N11 (residues 589-607 of SEQ ID NO: 1), N13 (residues 617-635 of SEQ ID NO: 1), N29 (residues 841-859 of SEQ ID NO: 1) and the L-chain peptide (218-231) stimulated strong-to-medium in vitro T cell responses (SI>5). In addition, peptides N2 (residues 463-481 of SEQ ID NO: 1), N16 (residues 659-677 of SEQ ID NO: 1) and N21 (residues 729-747 of SEQ ID NO: 1) and N28 (residues 827-845 of SEQ ID NO: 1) demonstrated weak (SI>3) stimulating activities. Toxoid-primed T cells of BALB/c and SJL did not respond to the unrelated hen lysozyme or ovalbumin proteins, demonstrating the specificity of the response.

Female BALB/c (H-$2^d$; National Cancer Institute; Frederick, Md.) and SJL/JCr (H-$2^s$; (Jackson Laboratory; Bar Harbor, Me.) mice, 7 to 9 weeks old, were used in all experiments. Synthetic peptides were synthesized, purified and characterized as described above. The twenty-nine consecutive overlapping peptides correspond to the complete $H_N$ domain (residues 449-859 of SEQ ID NO: 1) and a peptide around the enzymatic active site of the light chain (L-peptide, residues 218-231) of BoNT/A (FIG. 1A). The peptides were 19 residues in length and overlapped consecutively by five residues.

Immunization of mice with BoNT/A toxoid for T cell studies was performed as follows. The optimum priming dose of BoNT/A toxoid was determined in the BALB/c and SJL mouse strains. Mice were immunized subcutaneously at the base of tail with various doses of toxoid (0.125-5 µg/mouse) in a 50-µl emulsion of equal volumes of the toxoid solution in 0.15 M NaCl in 0.01 M sodium phosphate buffer, pH 7.2 (PBS), and complete Freund's adjuvant (CFA) containing *Mycobacterium tuberculosis*, strain H37Ra (Difco Laboratories; Detroit, Mich.). For both mouse strains, the highest T cell response was obtained at a priming dose of 1 µg/mouse, and subsequent experiments were performed with this dose. The peptides were used in vitro at five doses (5, 10, 20, 40, 80 µg/ml), and the toxin was used in vitro at doses of 1.25, 2.5, 5 and 10 µg/ml.

Lymphocyte proliferation assays were performed as follows. Single-cell suspensions of LNC from toxoid-primed mice were prepared in Hank's balanced salt solution. The cells were washed and resuspended in RPMI 1640 with 1% normal mouse serum and supplemented as described in Rosenberg et al., *Immunol. Invest.* 26:491-504 (1997). The number of viable cells was determined by vital staining with fluorescein diacetate. A fixed number of viable LNC ($5 \times 10^5$ to $8 \times 10^5$ cells/well) was cocultured in triplicate with various concentrations of mitogen, BoNT/A or synthetic peptides of BoNT/A, BoNT/B or TeNT and control proteins and peptides. The viability of the cells was confirmed in each assay by their responses to ConA and LPS. Negative controls included proteins unrelated to BoNT/A (ovalbumin, myoglobin and hen lysozyme) as well as unrelated control synthetic peptides. After three days of incubation at 37° C. in a humidified, 5% $CO_2$ atmosphere, lymphocytes were pulsed for 18 hours with [$^3$H]-thymidine (2 µCi/well; Research Products International; Mount Prospect, Ill.) and subsequently harvested onto glass microfiber filters (Whatman; Clinton, N.J.) before counting by liquid scintillation.

Figure 10:
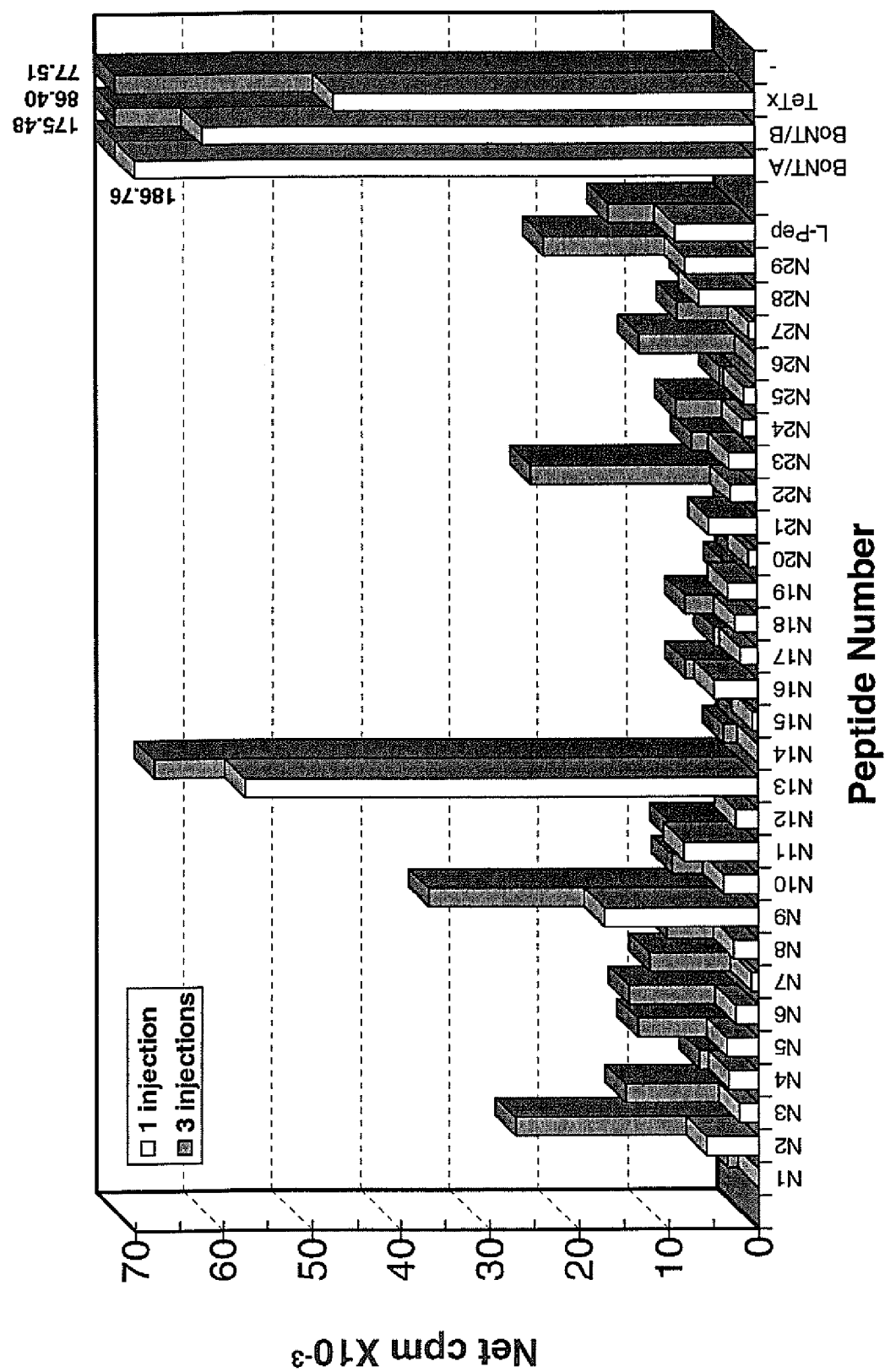
FIG. 10 shows proliferative responses of LNC ($5 \times 10^5$ cells/well) of SJL mice to various synthetic BoNT/A peptides after 1 injection or after 3 injections with BoNT/A toxoid (1:g/mouse/injection).

B. Mapping of the T Cell Recognition Profiles after Three Injections with Toxoid To determine T cell recognition profiles at the time antisera were obtained, proliferative responses were determined for LNC obtained from BALB/c and SJL mice that were used to prepare hyperimmune anti-toxoid antisera for the antibody-binding studies. LNC were harvested at the time of the final bleed on week 10 (i.e. 2 weeks after the last of three injections of toxoid). The proliferative responses to the peptides and toxins of LNC from once-primed and from three-times immunized BALB/c and SJL are shown in FIGS. 8 and 10; the results for both BALB/c and SJL are summarized in Table 4. As shown in FIG. 8, the two recognition profiles for T cells from BALB/c mice were only slightly different (FIG. 8).

ID NO: 1), N26 (residues 799-817 of SEQ ID NO: 1), N27 (residues 813-831 of SEQ ID NO: 1) and the L-peptide (218-231).

TABLE 4

The regions on the H chain of BoNT/A recognized by T cells after one injection and after 3 injections of BALB/c and SJL with BoNT/A toxoid.

| Peptide | Residue Number (SEQ ID NO: 1) | BALB/c (H-$2^d$) | | SJL (H-$2^s$) | |
|---|---|---|---|---|---|
| | | 1 Injection | 3 Injections | 1 Injection | 3 Injections |
| L-Peptide | 218-231 | − | − | ++ | ++ |
| | | $H_N$ Domain$^a$ | | | |
| N1 | 449-467 | − | − | − | − |
| N2 | 463-481 | − | − | + | ++++ |
| N3 | 477-495 | − | − | − | ++ |
| N4 | 491-509 | − | − | − | − |
| N5 | 505-523 | − | − | ± | ++ |
| N6 | 519-537 | − | − | − | ++ |
| N7 | 533-551 | − | − | − | ++ |
| N8 | 547-565 | − | − | − | + |
| N9 | 561-579 | − | − | +++ | ++++ |
| N10 | 575-593 | − | − | ± | + |
| N11 | 589-607 | − | − | ++ | + |
| N12 | 603-621 | − | − | − | − |
| N13 | 617-635 | − | − | +++++ | +++++ |
| N14 | 631-649 | − | − | − | − |
| N15 | 645-663 | − | − | − | − |
| N16 | 659-677 | − | − | + | + |
| N17 | 673-691 | − | − | − | − |
| N18 | 687-705 | ± | ± | − | ± |
| N19 | 701-719 | + | ++ | − | − |
| N20 | 715-733 | − | + | − | − |
| N21 | 729-747 | − | − | + | − |
| N22 | 743-761 | − | − | − | ++++ |
| N23 | 757-775 | − | − | − | ± |
| N24 | 771-789 | − | − | − | + |
| N25 | 785-803 | − | − | − | − |
| N26 | 799-817 | − | − | − | ++ |
| N27 | 813-831 | − | − | − | + |
| N28 | 827-845 | − | − | + | ± |
| N29 | 841-859 | − | − | ++ | +++ |
| BoNT/A | | +++++ | +++++ | +++++ | +++++ |
| NoNT/B | | + | +++ | +++++ | +++++ |
| TeNT | | − | − | +++++ | +++++ |

Hyperimmune T cells responded to challenge in vitro with peptides N18 (residues 687-705 of SEQ ID NO: 1), N19 (residues 701-719 of SEQ ID NO: 1) and N20 (residues 715-733 of SEQ ID NO: 1), with the response to peptide N19 (residues 701-719 of SEQ ID NO: 1) stronger after multiple injections. The recognition profile of the other peptides remained essentially unchanged, and BALB/c hyperimmune T cells did not cross-react with BoNT/B and TeNT.

The recognition profiles of once-primed and of hyperimmune LNC from SJL mice showed greater differences (FIG. 10 and Table 4). As shown in FIG. 10, hyperimmune T cells showed higher cross-reactivity with BoNT/B and TeNT than once-primed cells. In addition, the responses of hyperimmune SJL T cells to peptides N2 (residues 463-481 of SEQ ID NO: 1), N9 (residues 561-579 of SEQ ID NO: 1), N13 (residues 617-635 of SEQ ID NO: 1), N22 (residues 743-761 of SEQ ID NO: 1) and N29 (residues 841-859 of SEQ ID NO: 1) increased markedly. Hyperimmune SJL T cells also responded well to peptides N3 (residues 477-495 of SEQ ID NO: 1), N5 (residues 505-523 of SEQ ID NO: 1), N6 (residues 519-537 of SEQ ID NO: 1), N7 (residues 533-551 of SEQ ID NO: 1), N8 (residues 547-565 of SEQ ID NO: 1), N10 (residues 575-593 of SEQ ID NO: 1), N11 (residues 589-607 of SEQ ID NO: 1), N24 (residues 771-789 of SEQ Immunization of mice with BoNT/A toxoid for late T cell responses and antibody binding studies was performed as follows. Mouse antisera were prepared by injection of BALB/c and SJL mice subcutaneously in the hind footpads with 5 μg of toxoid emulsified in complete Freund's adjuvant (CFA). Mice were injected with boosters at 4 and 8 weeks with a similar dose of toxoid, using incomplete Freund's adjuvant (Difco Laboratories; Detroit, Mich.) instead of CFA. Sera were collected prior to the first immunization (pre-immune sera) and two weeks after each injection. For each mouse strain, sera of the respective bleeds from ten mice were pooled and kept at −20° C. until use. Antisera collected on week 10, i.e. 2 weeks after the last injection with toxoid, were employed for peptide binding studies. At the time of the last bleed, lymph nodes were removed, and single cell suspensions prepared for lymphocyte proliferation assays.

Figure 13:
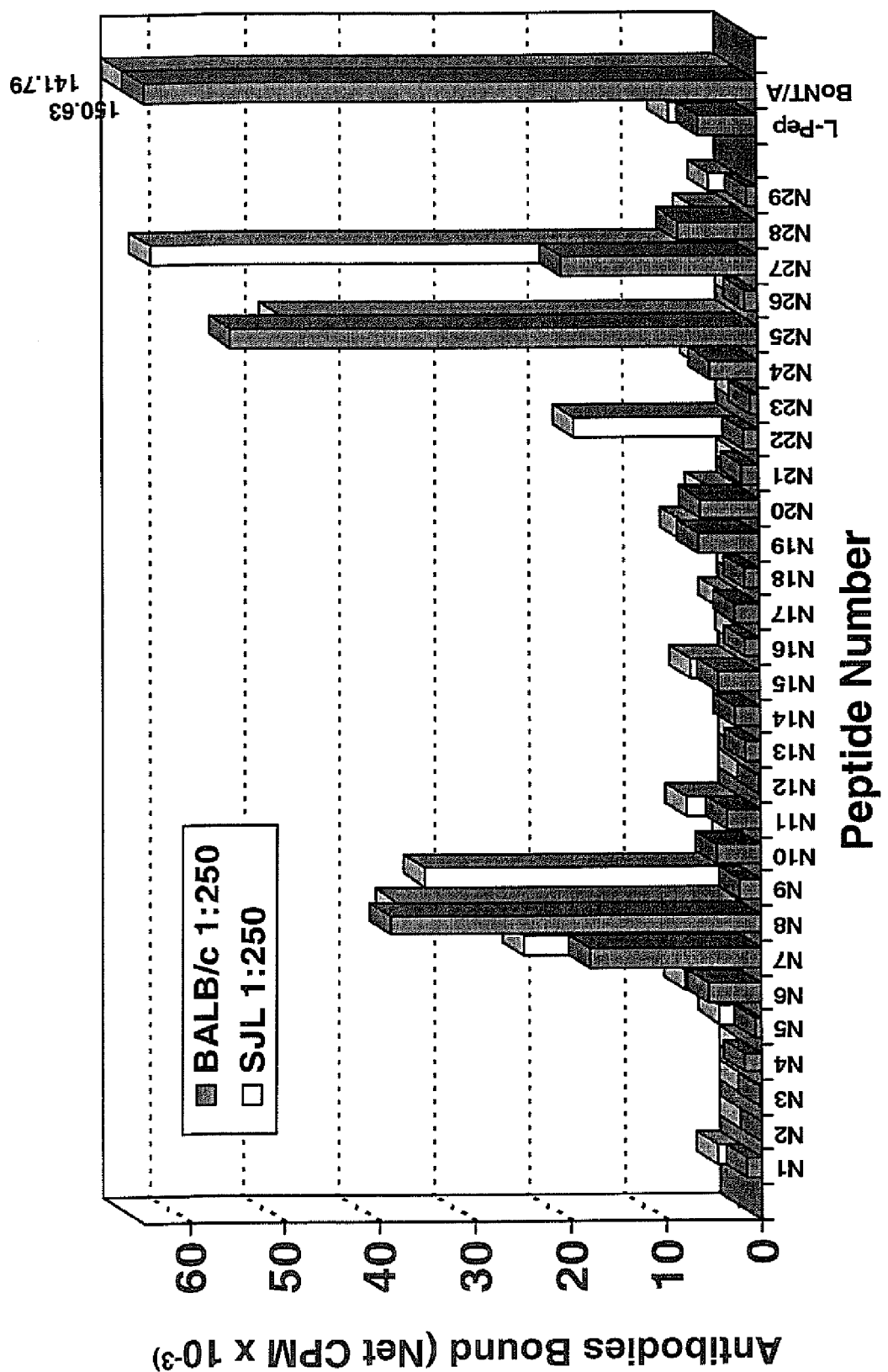
FIG. 13 shows a comparison of the binding profiles of BALB/c and SJL anti-BoNT/A toxoid antibodies at an antisera dilution of 1:250 (vol/vol), to BoNT/A and to overlapping synthetic peptides of the $H_N$-domain.

C. Binding of Anti-BoNT/A Antibodies to Overlapping Synthetic Peptides and Toxins Mapping of antibody binding profiles to peptides in the BALB/c and SLJ inbred mouse strains was performed by assaying antisera at two dilutions (1:250 and 1:500 (vol/vol)). As shown in FIGS. 5 and 6, respectively, the binding profiles of anti-toxoid antibodies from BALB/c and SJL mice were substantially similar. FIG. 13 shows a direct comparison of BALB/c and SJL antisera binding, and Table 5 summarizes the binding profiles for BALB/c and SJL Abs to the $H_N$ peptides at a dilution of 1:250 (vol/vol). Antibodies from both mouse strains showed high binding to $H_N$ peptides N7, N8, N25 and N27 and low binding to peptides N6, N11, N15 and N19.

TABLE 5

The regions on the H chain of BoNT/A recognized by T cells and/or Abs after 3 injections of BALB/c and SJL with BoNT/A toxoid.

| Peptide | Residue Number (SEQ ID NO: 1) | BALB/c (H-$2^d$) Abs | T-cells | SJL (H-$2^s$) Abs | T-cells |
|---|---|---|---|---|---|
| L-Peptide | 218-231 | + | − | + | ++ |
| $H_N$ Domain[a] | | | | | |
| N1 | 449-467 | ± | − | − | − |
| N2 | 463-481 | − | − | − | ++++ |
| N3 | 477-495 | − | − | − | ++ |
| N4 | 491-509 | ± | − | − | − |
| N5 | 505-523 | − | − | − | ++ |
| N6 | 519-537 | + | − | + | ++ |
| N7 | 533-551 | +++ | − | +++ | ++ |
| N8 | 547-565 | ++++ | − | ++++ | + |
| N9 | 561-579 | ± | − | +++ | ++++ |
| N10 | 575-593 | + | − | − | + |
| N11 | 589-607 | + | − | − | + |
| N12 | 603-621 | − | − | − | − |
| N13 | 617-635 | − | − | − | +++++ |
| N14 | 631-649 | − | − | − | − |
| N15 | 645-663 | + | − | + | − |
| N16 | 659-677 | − | − | − | + |
| N17 | 673-691 | − | − | − | − |
| N18 | 687-705 | − | ± | − | ± |
| N19 | 701-719 | + | ++ | + | − |
| N20 | 715-733 | + | + | − | − |
| N21 | 729-747 | − | − | − | − |
| N22 | 743-761 | ± | − | +++ | ++++ |
| N23 | 757-775 | − | − | − | ± |
| N24 | 771-789 | + | − | − | + |
| N25 | 785-803 | ++++ | − | ++++ | − |
| N26 | 799-817 | − | − | − | ++ |
| N27 | 813-831 | +++ | − | ++++ | + |
| N28 | 827-845 | ++ | − | ± | ± |
| N29 | 841-859 | − | − | − | +++ |
| BoNT/A | | | +++++ | | +++++ |
| NoNT/B | | | ++ | | +++++ |
| TeNT | | | − | | +++++ |
| $H_C$ Domain[b] | | | | | |
| C1 | 855-873 | − | − | + | − |
| C2 | 869-887 | ++ | − | +++ | − |
| C3 | 883-901 | ++ | − | ++ | − |
| C4 | 897-915 | − | ++ | − | ++++ |
| C5 | 911-929 | − | − | + | + |
| C6 | 925-943 | + | − | + | + |
| C7 | 939-957 | + | ++ | + | +++ |
| C8 | 953-971 | − | − | − | ++ |
| C9 | 967-985 | + | − | + | − |
| C10 | 981-999 | + | − | + | − |
| C11 | 995-1013 | + | − | +++ | − |
| C12 | 1009-1027 | − | + | − | + |
| C13 | 1023-1041 | + | − | − | ++ |
| C14 | 1037-1055 | − | − | − | + |
| C15 | 1051-1069 | + | − | ++ | +++ |
| C16 | 1065-1083 | − | − | − | + |
| C17 | 1079-1097 | − | − | − | ++ |
| C18 | 1093-1111 | − | ± | + | + |
| C19 | 1107-1125 | + | ++ | + | + |
| C20 | 1121-1139 | − | + | + | ++ |
| C21 | 1135-1153 | ++ | − | + | + |
| C22 | 1149-1167 | − | − | + | + |
| C23 | 1163-1181 | − | − | − | ++ |
| C24 | 1177-1195 | − | − | +++ | + |
| C25 | 1191-1209 | − | − | + | + |
| C26 | 1205-1223 | − | − | + | − |
| C27 | 1219-1237 | − | − | − | − |
| C28 | 1233-1251 | − | − | + | + |
| C29 | 1247-1265 | − | − | − | + |
| C30 | 1261-1279 | − | − | + | − |
| C31 | 1275-1296 | ++ | − | ++ | ++ |

[a]Results from the present work. For the purpose of this table, (+) and (−) assignments were based on net cpm values for Ab binding and SI values for T cell proliferation. For Ab binding, the symbols denote the following values: (−), less than 1,500 cpm; (□), 1,500-3,000 cpm; (+), 3,000-7,000 cpm; (++), 7,000-15,000 cpm; (+++), 15,000-25,000 cpm; (++++), 25,000-35,000 cpm; (+++++), exceeding 35,000 cpm. For T cell proliferation, the symbols indicate the following: (−), SI value less then 2.0; (±) 2.0-2.5; (+), SI 2.6-3.5; (++), SI 3.6-6.0; (+++), SI 6.1-10.0; (++++), 10.1-25 (+++++) SI > 25.0.
[b]Results of The Hc domain peptide recognition by anti-toxoid Abs and T cells of BALB/c and SJL mice are from Rosenberg et al., 1997.

Some differences in the binding profiles of antibodies from the two mouse strains were also apparent. In particular, BALB/c antisera showed medium antibody binding to peptide N28 and low antibody binding to peptides N10, N20 and N24, which represented epitopes either unrecognized or poorly recognized by SJL antibodies. On the other hand, SJL antibodies showed high binding to peptides N9 and N22, which were poorly recognized by BALB/c antibodies. In addition, SJL antisera contained much higher amounts of antisera that bound to peptide N27 than did antisera from the other mouse strain. In order to complete the profiles of the H chain recognition by BALB/c and SJL antibodies, Table 5 shows binding profiles to $H_C$ peptides previously reported (Rosenberg et al., supra, 1997).

Solid phase radioimmunoassays were performed using Staphylococcal protein A (Pharmacia Biotech; Piscataway, N.J.) radiolabeled with $^{125}I$ (Amersham Corp.; Arlington Heights, Ill.) using the chloramine-T method. Unbound $^{125}I$ was separated from the radiolabeled protein A by gel filtration on a column (0.8×20 cm) of Sephadex G-25, equilibrated with PBS containing 0.1% bovine serum albumin (BSA; Sigma Chemicals; St. Louis, Mo.).

Binding of mouse anti-toxoid antibodies to active BoNT/A and to synthetic peptides was determined using polyvinylchloride 96-well plates (Becton Dickinson Labware; Oxnard, Calif.), which were coated with each of the 31 overlapping peptides (2.5 μg in 50 μl of PBS/well) or with BoNT/A (1 μg in 50 μl of PBS/well). Wells coated with proteins and synthetic peptides unrelated to BoNTs were used as negative controls. Following overnight incubation at 4° C., plates were washed extensively with PBS and incubated for one hour at 37° C. with 1% BSA in PBS (100 μl/well) to block nonspecific binding in subsequent steps. After washing with PBS, plates were incubated at 37° C. for three hours with mouse antisera (50 μl/well) appropriately prediluted in 0.1% BSA in PBS. For mapping studies, antisera were prediluted 1:250 and 1:500 (vol/vol). Wells were washed with PBS and incubated at 37° C. for two hours with 50 μl of affinity purified rabbit anti-mouse (IgG+IgM) antisera (Accurate Chem. Sci. Corp.; Westbury, N.Y.) pre-diluted 1:1000 (vol/vol) with 0.1% BSA in PBS. After washing with PBS, $^{125}I$-labeled protein A was added to the wells (2×10$^5$ cpm in 50 μl 0.1% BSA-PBS/well). Plates were subsequently incubated for two hours at room temperature, washed, dried and the wells cut out and counted in a gamma counter (1227 Gammamaster; LKB; Turku, Finland). All determinations were performed in triplicate, and the results expressed as net cpm±SD, after corrections for nonspecific binding in controls wells that were coated with BSA and of the correlate pre-immune mouse sera to each tested antigen.

D. Protective Activity of Anti-BoNT/A Antibodies In Vivo

Figure 14:
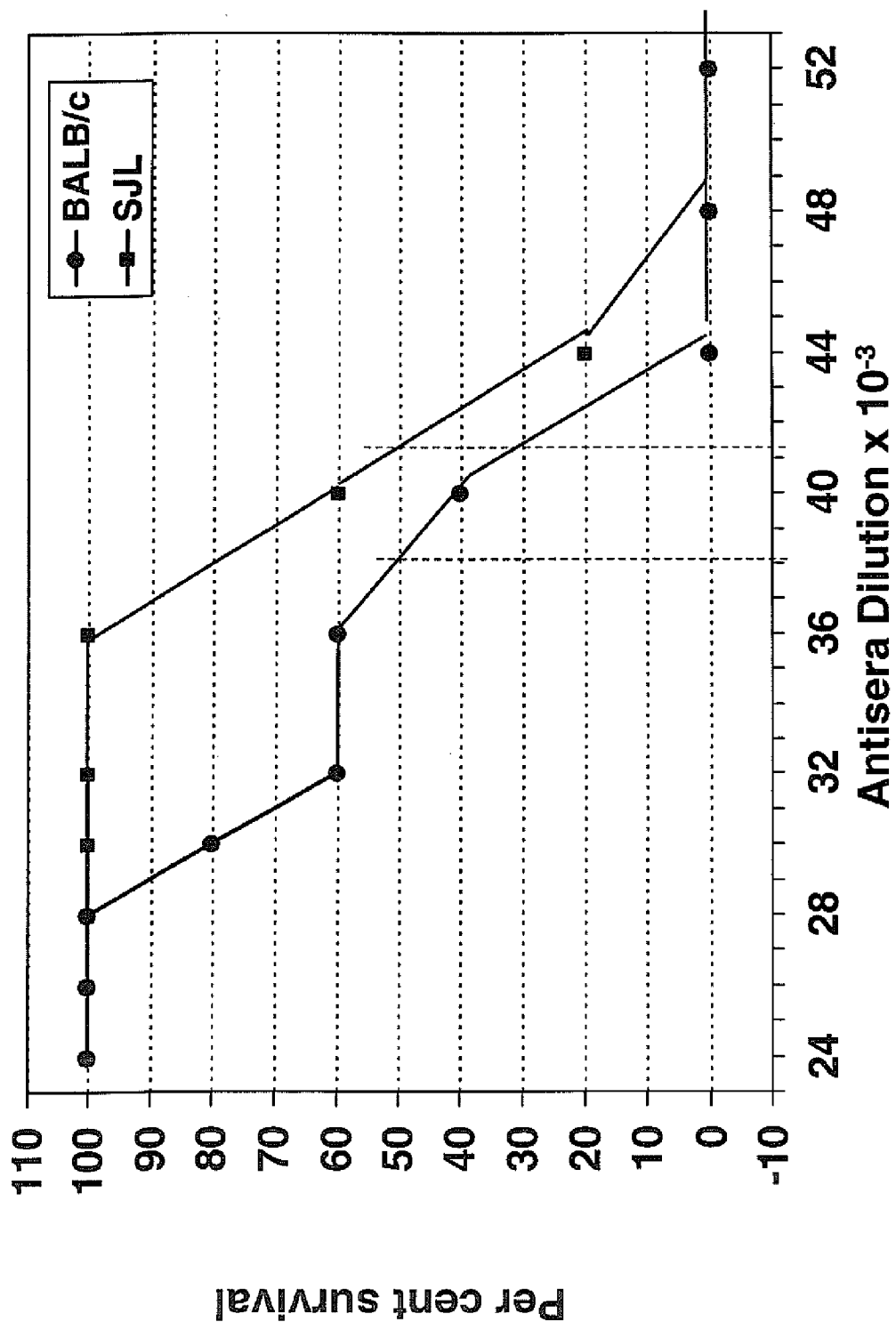
FIG. 14 shows protective activity of different dilutions of BALB/c and SJL anti-BoNT/A antisera. The results are expressed in percent survival to BoNT/A challenge versus antiserum dilution.

Anti-BoNT/A antisera from BALB/c and SJL mice were assayed for the ability to protect against a lethal dose of active BoNT/A as described further below. Serial dilutions of BALB/c and SJL antisera were assayed for the ability to protect ICR mice against $1.05 \times LD_{100}$ (i.e., 6.5 µg) of BoNT/A. As shown in FIG. 14, antisera of both BALB/c and SJL contained high titers of blocking antibodies that protected mice at very high dilutions. Anti-toxin antisera of BALB/c mice were fully protective in recipient ICR mice at dilutions up to 1:28000 (vol/vol), and 50% protection was obtained at 1:38000 (vol/vol). SJL antisera were even more protective, fully protecting recipient ICR mice against a lethal dose of active BoNT/A at 1:36000 dilution (vol/vol), while 50% protection was achieved at 1:41000 dilution (vol/vol). As expected, non-immune sera were not protective at any dilution. These results indicate that anti-toxoid antibodies can be useful for conferring protection against botulinum toxin.

The presence of blocking antibodies in mouse antisera against BoNT/A was determined by a mouse protection assay essentially as follows. The survival of outbred (ICR) mice against various doses of BoNT/A administered intravenously was determined using five mice at each dose. The dose at which no mice survived (i.e., $LD_{100}$) was 5.0 pg/mouse when a fresh preparation of BoNT/A was tested. At the time the mouse protection assays were performed, after storage of toxoid for about 6 months at $-20°$ C. in PBS containing 20% glycerin, the $LD_{100}$ was 6.2 pg/mouse. To determine the protective activity of BALB/c and SJL anti-BoNT/A antisera, ICR mice were injected intravenously in the tail with a mixture of $1.05 \times LD_{100}$ of active BoNT/A (i.e., 6.5 pg/mouse) and 100 µl of serial dilutions of the indicated mouse antiserum. Each dilution was injected into five mice, and the mice were observed three times a day for six days. Where test antisera contained blocking antibodies, all mice recovered and survived the challenge. When protecting antibodies were either absent or their amounts too low at high dilution, then none or only some of the mice survived the BoNT/A challenge. The results were plotted as percent survival versus antisera dilutions.

Example VIII

Submolecular Recognition Profiles in Two Mouse Strains of Non-Protective and Protective Anti-Bont/A Antibodies This example demonstrates that the switch in BALB/c and SJL mice from non-protective to protective antibodies is not associated with major changes in epitope recognition profiles but is rather associated with the immunoglobulin class of the antibodies.

A. Protective Activity of Anti-BoNT/A Antibodies In Vivo

As described above, female BALB/c ($H-2^d$) and SJL/JCr ($H-2^s$) mice, 7 to 9 weeks old, were used in all experiments. The mouse protection assay was performed as described in Example VII above. Formaldehyde-inactivated, and active BoNT/A were purchased from Metabiologics (Madison, Wis.).

Anti-toxin antisera of BALB/c and SJL remained unprotective in recipient ICR mice on 26 day after the first BoNT/A injection. Mice were boosted on day 27, and nine days after the second injection (i.e., day 36 after the first injection), antisera were tested for protection. BALB/c antisera were protective against a challenge dose of $1.05 \times LD_{100}$, when administered undiluted. SJL antisera were protective on day 36; these antisera were protective at dilutions up to 1:4 and were not protective at dilutions of 1:8. Non-immune sera were not protective even when undiluted. These results serve to define the timing of the switch between production of unprotective and protective anti-BoNT/A antibodies.

B. Binding Profile of Non-Protective and Protective Total Antibodies

For mapping of peptide binding profiles, antisera were assayed at dilutions of 1:100 and 1:250 (vol/vol). Binding profiles of total (IgG and IgM) anti-toxin antibodies from BALB/c and SJL mice were determined for two bleeds: The bleed on day 26 containing non-protective antibodies and the bleed following it on day 36 in which the antibodies demonstrated protective activity.

As shown in FIG. 16, upper panel, non-protective and protective BALB/c antisera showed very similar peptide-binding profiles at a dilution of 1:100. At a dilution of 1:250, the protective BALB/c antisera displayed higher binding to essentially every peptide (FIG. 16, lower panel). The BALB/c antibody-binding peptides were: N6/N7, N25, C2/C3, C9/C10/C11, C15, C18, C24, C30 and C31. Antibodies in the non-protective and protective antisera bound to peptide C30 at similar levels at a dilution of 1:100. However, at a dilution of 1:250, antibody binding to C30 in the non-protective antisera was greatly diminished while binding in the protective antisera remained unaffected, indicating a lower affinity of the antibodies directed against region C30 in the non-protective antisera. Low, but reproducible amounts of antibodies were bound by peptides N19, C6/C7 and C28.

The binding profiles for SJL total antibodies are shown in FIG. 17 at dilutions of 1:100 and 1:250 (vol/vol), upper and lower panels, respectively. In the case of the SJL mice, some differences were apparent between non-protective and protective antisera when total antibodies were analyzed. Peptides N5, N22 and C21, which were recognized by protective antisera, were only slightly recognized (N22 and C21) or not recognized (N5) by non-protective sera. Additionally, in the protective antisera, peptides N7/N8, N25, C11, C15 and less so N27/N28 bound two-fold or higher amounts of antibodies as compared with non-protective antisera. Additional peptides, C4 and C29, bound higher amounts of antibodies in protective sera as compared to non-protective sera at a dilution of 1:100. However these differences disappeared at 1:250, indicating that these antibodies were of relatively low affinity. Peptides C2/C3, C7, C18/C19, C24, C30 and C31 also bound higher amounts of antibodies in protective sera as compared with non-protective antisera, but the differences were less than double. As expected, anti-toxin antibodies did not bind to unrelated proteins or peptides, and pre-immune sera displayed no binding to BoNT/A or its peptides, indicative of specific binding.

In sum, these results demonstrate only very small differences between the peptide recognition profiles of protective and non-protective antisera. These results further indicate that differences in antibody binding levels likely do not account for the difference in protective activity of the non-protective and protective antisera.

Assays were performed as follows. A total of 60 consecutive overlapping peptides corresponding to the complete H subunit (residues 449-1296 of SEQ ID NO: 1), and a peptide around the enzymatic active site of the light chain (L-peptide, residues 218-231), of BoNT/A (FIG. 1) were synthesized, purified and characterized as described above. The peptides were 19 residues long and overlapped consecutively by five residues except for the last peptide in the sequence (C31, residues 1275-1296 of SEQ ID NO: 1). Mice were immunized as described above, with two boosters given at days 27 and 60 with a similar dose of toxoid, using incomplete Freund's adjuvant. Sera were collected prior to the first immunization (preimmune sera) and on days 20, 26, 36, 46, 57, 68 and 70. For each mouse strain, sera of the respective bleeds from 10 mice were pooled and kept at −20° C. The non-protective sera from day 26 and protective sera from day 36 were employed for peptide binding studies. Binding was determined by solid-phase radioimmunoassay as described in Example VII above, except that affinity-purified rabbit anti-mouse (IgG and IgM) or anti-mouse IgG antisera (Accurate Chem. Sci. Corp.; Westbury, N.Y.) was used as appropriate.

C. Binding of Non-Protective and Protective IgG Antibodies to Synthetic BoNT/A Peptides and to BoNT/A As described above, differences in total antibody reactivity between protective and non-protective antisera, particularly in the case of BALB/c antisera, appeared insufficient to explain the protective properties of the antisera. The peptide-binding profiles of IgG antibodies alone showed different results. In their binding to active BoNT/A, BALB/c and SJL protective antisera had 13-36 fold higher levels of IgG antibodies relative to non-protective antisera. The profiles for BALB/c and SJL protective and non-protective antibodies are shown in FIGS. 18 and 19, respectively. IgG antibodies in the protective antisera of each mouse strain bound to the same peptides as did total antibodies (IgG and IgM) in the correlate antiserum. However, in both mouse strains, the non-protective antisera contained few, if any, IgG antibodies that bound to these peptides, even at a dilution of 1:100. Again, specific binding was demonstrated by the absence of binding to unrelated proteins and peptides, and by the absence of BoNT/A binding by non-immune sera.

These results demonstrate that protective antibodies had much higher IgG levels that bound to BoNT/A and to synthetic BoNT/A peptides (FIG. 18). In their binding to active BoNT/A, BALB/c protective antisera had up to 36-fold higher amounts of IgG antibodies relative to non-protective antisera (FIG. 18). Similarly, for SJL, the protective antibodies had up to 16-fold higher levels of IgG that bound to active BoNT/A than did the non-protective antibodies (FIG. 19). Furthermore, non-protective SJL and BALB/c antibodies each exhibited little or no binding to the peptides. These results demonstrate that the major difference between the protective and non-protective antibodies was the fact that non-protective antibodies, obtained after only one immunization with BoNT/A, were primarily of the IgM class. In contrast, protective antibodies obtained 10 days after the first booster displayed an IgM-to-IgG switch. In sum, these results indicate that protection is associated with antibodies of the IgG class.

Example IX

Mapping of the H Chain Recognition Profile in Antisera from a Cohort of Cervical Dystonia (CD) Patients This example demonstrates that an in vitro assay can be used to determine amounts of blocking or protective antibodies against BoNT/A in human serum samples. This example further demonstrates that a combination assay using, for example, two or three synthetic BoNT/A peptides can be used for sensitive detection of the presence of specific anti-toxin antibodies in, for example, BOTOX® treated patients.

A. Methods for Data Analysis

MPA-positive cervical dystonia (CD) serum samples were obtained from Allergan, Parkinson's Disease Center and Movement Disorders Clinic of Baylor College of Medicine, and the Arizona Dystonia Institute. CD patient sera protected against a lethal dose of BoNT/A in a mouse protection bio-assay were screened with 60 synthetic toxin peptides corresponding to the entire H chain of BoNT/A (FIG. 1). The IgG fraction of hyperimmune sera of human volunteers (obtained from the Department of the Army) against pentavalent toxin (BoNT/A, B, C, D and E) was used as a positive control. An aliquot (50 µl) of each of the 60 synthetic overlapping peptides, dissolved in 0.01 M phosphate buffer, pH 7.2 containing 0.15 M NaCl (1.0 µg/50 µl of PBS), was added to three wells of a flexible polyvinyl chloride 96-well plate. Peptides were allowed to bind for two hours at 37° C. followed by overnight incubation at 4° C. Plates were washed five times with PBS to remove unbound peptide and then blocked for one hour at 37° C. with 0.5% bovine serum albumin in PBS (BSA/PBS). An appropriate volume of each of the mouse protection assay (MPA)-positive CD sera was preincubated with an equal volume of TeNT toxoid (1 mg/ml) for three hours at 37° C. after which it was diluted to 1:500 (vol/vol) with 0.1% BSA/PBS, pipetted (50 µl) into peptide-coated wells and allowed to react for three hours at 37° C. followed by further incubation overnight at 4° C. After washing the wells five times with PBS, 50 µl of prediluted (1:500 vol/vol, in 0.1% BSA/PBS) immunoglobulin fraction of rabbit anti-human IgG (DAKO Corporation; Carpinteria, Calif. A0424)+ IgM (Mu chain; DAKO, A0426) was added and allowed to react at 37° C. for two hours. The wells were washed five times with PBS followed by addition of 50 µl of $^{125}$I-Protein A ($2\times10^5$ CPM in 0.1% BSA/PBS) to each well and incubation for two hours at room temperature. Finally, plates were washed thoroughly to eliminate unbound radioactivity; individual wells were cut out and transferred into separate tubes; and the incorporated radioactivity was counted in a gamma-counter (1277 Gamma Master; LKB, Finland). The results, which were obtained from triplicate analyses, were expressed as the ratios of mean CPM bound by peptides over CPM bound by control peptides or bovine serum albumin (BSA).

For determining antibody binding to BoNT/A or BoNT/B, triplicate wells were coated with the appropriate inactive BoNT/A or BoNT/B toxin (0.5 µg/50 µl of PBS). A similar procedure was then used to determine the amount of antibody bound by BoNT/A or BoNT/B using human MPA-positive CD sera pre-absorbed with TeNT.

B. Assay of Total Antibodies Bound to BoNT/A and BoNT/B

Due to varying amounts of anti-TeNT antibodies in human sera and the cross-reactivity of these antibodies with both BoNT/A as well as BoNT/B (Behzod et al., Immunol. Invest. 31:247-262 (2002)), the binding assay described above was modified. Essentially, the reaction with BoNT/A or synthetic BoNT/A peptides was carried out either after absorption of the sera with TeNT or, more conveniently, in the presence of a large excess of TeNT as described further below. The pool of positive control antisera was obtained from human volunteers, and was tested at two dilutions (1:1000 and 1:2000, vol/vol).

Binding studies of the antisera from CD patients as well as sera from unimmunized controls showed that the sera had different levels of non-specific binding to unrelated protein (BSA) and peptides. This high non-specific binding affected both the net cpm values as well as the ratio of the signal (specific binding) to background (non-specific binding). Sera from the same cervical dystonia patients prior to toxin treatment (pre-immune sera) were not available to correct for the non-specific binding. However, the amount of radiolabel bound by certain synthetic H peptides was observed to be essentially the same as the amount of radiolabel bound to unrelated proteins and peptides. These non-antibody-binding H chain peptides (for example, N2, N3, N5, N6, N7, N9, N10, N11, N12, etc.; see FIG. 1) were utilized as an internal control for each serum. In particular, binding was expressed for each serum as a ratio of the amount of antibody bound by a test peptide over the average of the amounts of antibody bound by four of the non-antibody binding H-chain peptides (N2, N12, C17 and C23). The value for such a ratio of antibodies bound to a given peptide from a given serum was essentially constant.

In assays to determine the total amounts of antibody present in CD patient sera, BSA and the four non-binding peptides N2, N12, C17 and C23 were used as negative controls. The results of antibody binding to BoNT/A toxoid in 28 MPA-positive CD sera and 10 human sera from unimmunized controls are summarized in FIG. 21. The results show that 27 out of 28 (96.4%) MPA-positive sera bound antibody levels that were clearly higher than those bound by the controls. These results validate the use of assays performed with human sera in a large excess of TeNT to determine the total amounts of antibodies to BoNT/A present in the serum of a patient in the course of treatment with BOTOX®.

In determining the total amount of anti-BoNT/B antibodies present in CD patient sera, BSA was used as the negative control. The results of binding to the BoNT/B toxoid of antibodies in 28 MPA-positive CD sera and 10 human sera from unimmunized controls are summarized in FIG. 22. The results show that 27 out of 28 (96.4%) of MPA-positive sera bound antibody levels that were clearly higher than those bound by the controls, while one was close to the borderline. These results validate the use of this assay for determining total amounts of antibodies to BoNT/B present in patient serum in the course of treatment with a BoNT/B formulation.

C. Mapping of Epitopes Recognized by Antibodies in of MPA-Positive Sera of Cervical Dystonia Patients The results of mapping by the synthetic H-chain peptides of antibodies from 28 CD patients that were MPA positive are shown in FIGS. 24 to 26 and summarized in Table 6. These data, which represent four replicate experiments, are compared to binding profiles obtained with hyperimmune human sera at 1:1000 and 1:2000 (vol/vol). As described above, the results in FIGS. 24 to 26 and in Table 6 are based on the ratio of cpm bound by a given peptide/cpm bound by BSA and/or average of cpm bound by peptides N2, N12, C17 and C23. In Table 6, (−) denotes no detectable binding; (±) indicates very low but reproducible binding (ratio of specific over non-specific binding of 1.61-2.0); and different numbers of (+) signs indicate different levels of binding. As can be seen by comparison with the data reported above, peptides which bound antibodies in the sera of the CD patients also bound antibodies within hyperimmune sera. However, not every peptide that bound antibodies in hyperimmune serum was able to bind antibodies in patient sera, indicating that the antibody-binding profile of the patients' sera was more restricted than the profile of the hyperimmune sera.

Furthermore, variability was seen among the binding profiles for different patients. As an example, the antisera of some patients bound peptide N4, whereas other sera had no such binding-activity. This inter-patient variability is consistent with the fact that immune responses to protein antigens are known to be under genetic control and that the response to each epitope within a protein is under separate genetic control (Okuda et al., *J. Immunol.* 121:866-868 (1978)).

Significantly, however, some peptides bound antibodies in most of the patients. For example, 25 out of 28 sera contained antibodies that bound to peptide N25, although the amounts bound varied from patient to patient with three sera (patients 45, 304 and 310) having marginal levels of antibodies to this peptide. Peptide C10 bound antibodies in sera of 24 out of 28 patients, with the sera of patients 43, 45, 53 and SD displaying very low (±) or no (−) antibody binding to peptide C10. Peptide C15 displayed low (+) to medium (++) binding to antibodies in 17 patient sera; very low (O) binding with nine patient sera; and no binding with two sera. The antibody-binding activity of peptide C20 was generally lower than peptides N25 or C10 but was low (+) to high (+++) in nine of the patient sera, while eight sera showed no antibody binding, and 11 sera showed very low (±), but reproducible, levels of binding. In addition, peptide C31 bound antibodies in 17 sera, showed very low binding in eight patient sera, and displayed no detectable antibody binding with three patient sera. These results indicate that, while there is some peptide-binding variability among MPA-positive CD patient sera, several synthetic BoNT/A peptides bind antibodies in the large majority of patient sera.

Figure 28:
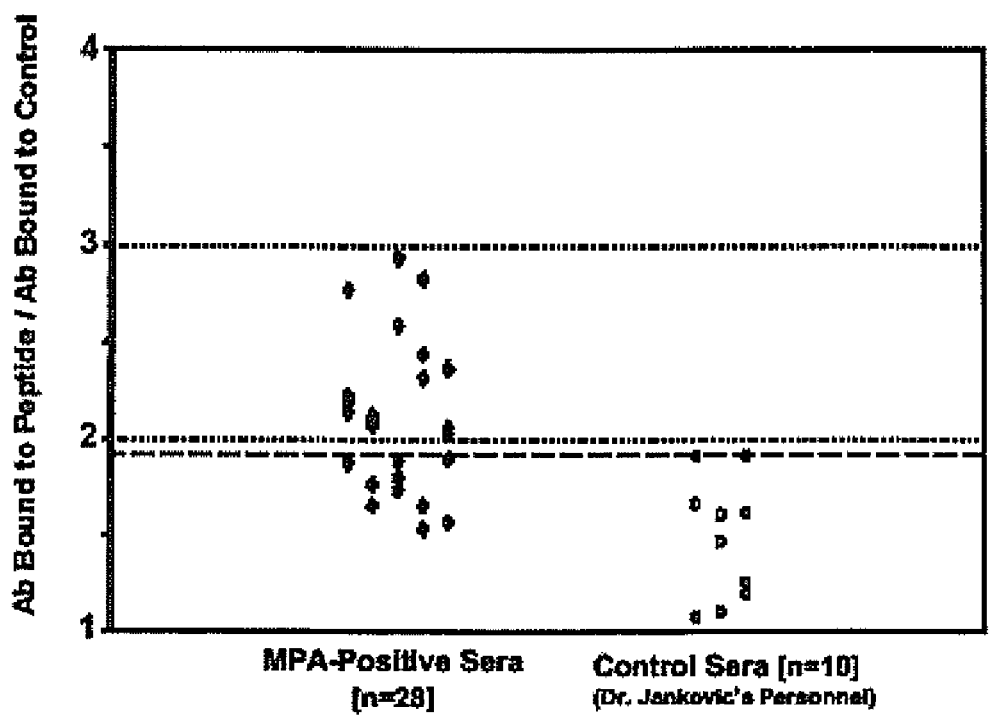
FIG. 28 shows binding to peptide C15 of antibodies in MPA-positive sera from CD patients (n=28) and in normal controls (n=10). Results are the average of four experiments and are expressed as a ratio of (antibodies bound to peptide C10)/(average of antibodies bound by negative control peptides N2, N12, C17 and C23).
Figure 29:
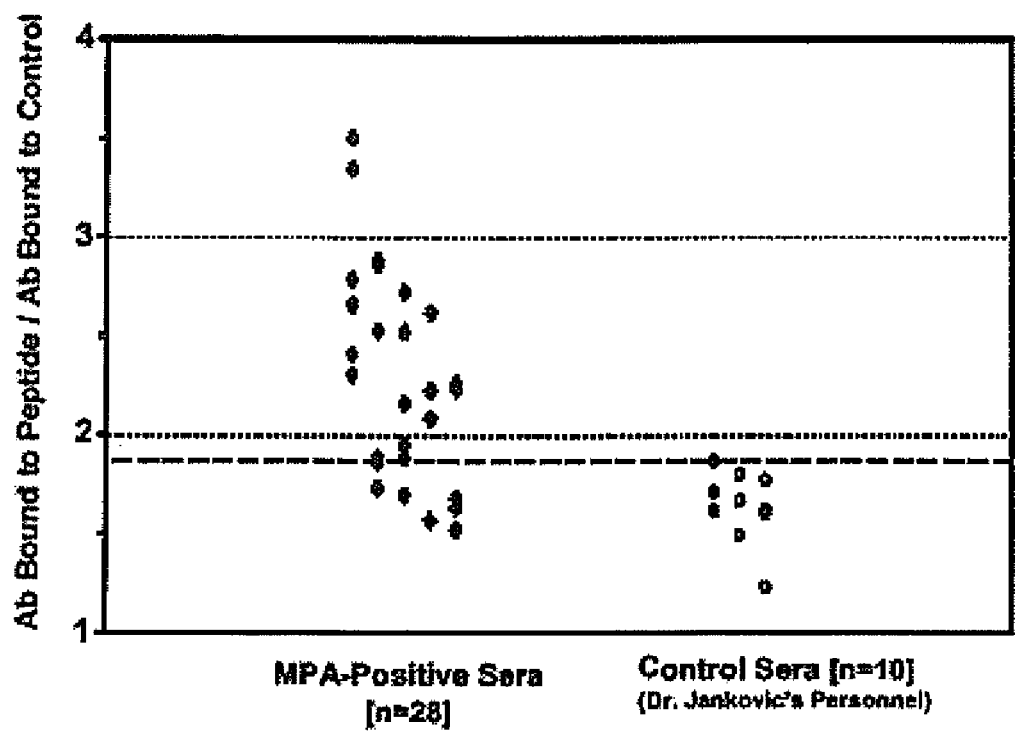
FIG. 29 shows binding to peptide C31 of antibodies in MPA-positive sera from CD patients (n=28) and in normal controls (n=10). Results are the average of four experiments and are expressed as a ratio of (antibodies bound to peptide C10)/(average of antibodies bound by negative control peptides N2, N12, C17 and C23).

D. Synthetic Peptide Assay for Analysis of Reactivity of MPA-Positive Patient Sera As disclosed above, MPA-positive cervical dystonia patient sera contained antibodies that bound to one or more of the peptides N25, C10, C15, C20 and C31, indicating that binding to one or more of these peptides can used to determine the presence of antibody responses in patient sera. FIGS. 27, 28, 29 and 30 show the ratio of the specific cpm bound in the same assay to non-binding peptides and to BSA. As shown in FIG. 26, analysis on the basis of peptide N25 was able to distinguish clearly 21 out of 28 (75%) of patient sera from unimmunized controls. Binding to peptide C10 was also able to distinguish 21 out of 28 sera from the controls, while binding to peptides C15 and C31 distinguished 18 (64.3%) and 20 (71.4%) out of 28 sera, respectively (FIGS. 28 to 30).

Figure 31:
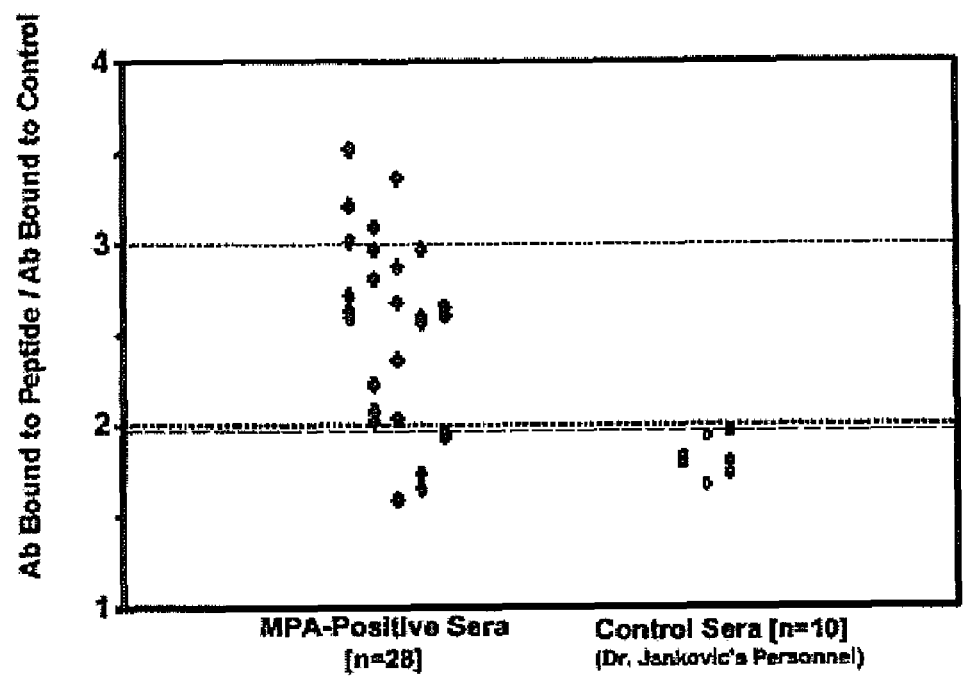
FIG. 31 shows binding peptides (N25+C10+C31) of antibodies in MPA-positive sera from CD patients (n=28) and in normal controls (n=10). Results, which are the average of four experiments, are expressed as a ratio of (antibodies bound to peptides N25+C10+C31)/(average of antibodies bound by negative control peptides N2, N12, C17 and C23).
Figure 33:
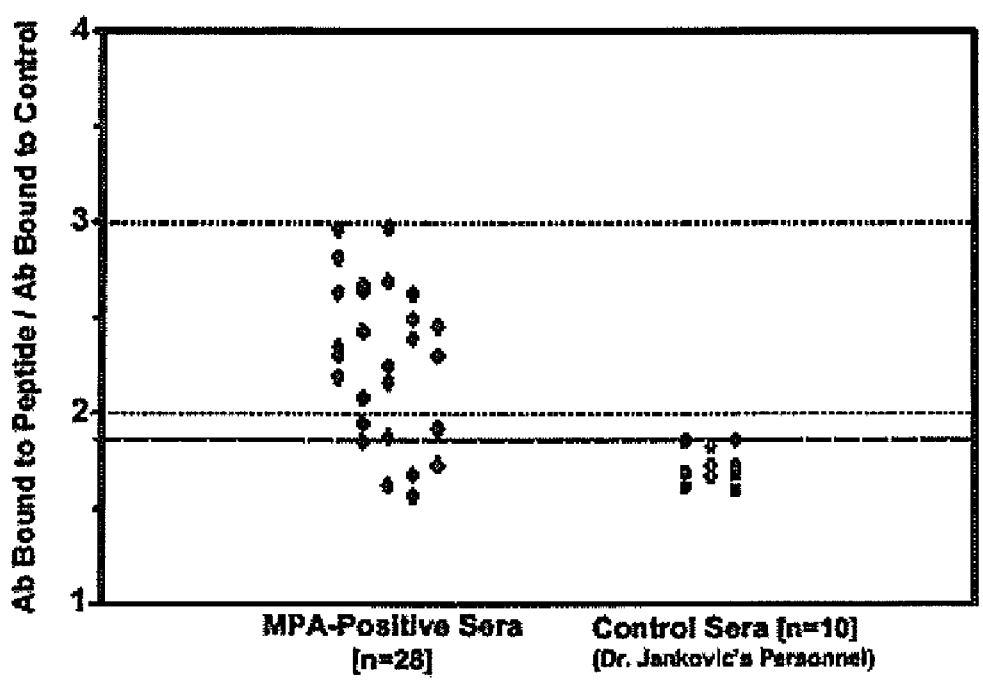
FIG. 33 shows binding to peptides (N25+C10+C15+C31) of antibodies in MPA-positive sera from CD patients (n=28) and in normal controls (n=10). Results, which are the average of four experiments, are expressed as a ratio of (antibodies bound to peptides N25+C10+C15+C31)/(average of antibodies bound by negative control peptides N2, N12, C17 and C23).

Combinations of two or more peptides were also assayed for their discriminatory capability. As shown in FIG. 30, when peptides N25 and C10 were combined in the assay, 25 out of 28 (89.3%) of the CD sera were discriminated from controls. The combination of peptides N25, C10 and C31 distinguished 24 out of 28 sera (85.7%; FIG. 31), and the combination of peptides N25, C10 and C15 distinguished 25 out of 28 (89.3%) of the MPA-positive CD sera from controls (see FIG. 32). Finally, a combination of four peptides (N25, C10, C15 and C31) distinguished 21 out of 28 sera (75%) from the controls, as shown in FIG. 33. These results demonstrate that a combination assay using peptides N25 and C10 or N25, C10 and C15 can be useful for detecting the presence of specific anti-toxin antibodies in BOTOX® treated patients.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed:

1. An isolated botulinum toxin serotype A (BoNT/A) peptide of SEQ ID NO: 1 having a length of at most 30 amino acids, said BoNT/A peptide comprising a 19 amino acid BoNT/A immunoreactive fragment consisting of amino acids 785-803 of SEQ ID NO: 1 or said 19 amino acid BoNT/A immunoreactive fragment having 1-4 conservative amino acid substitutions;
wherein said 19 amino acid BoNT/A immunoreactive fragment having 1-4 conservative amino acid substitutions is immunoreactive with BoNT/A.

2. The BoNT/A peptide of claim 1, wherein said 19 amino acid BoNT/A immunoreactive fragment is amino acids 785-803 of SEQ ID NO: 1.

3. The BoNT/A peptide of claim 1, wherein said BoNT/A peptide has a length of at most 25 amino acids.

4. An isolated botulinum toxin serotype A (BoNT/A) peptide of SEQ ID NO: 1 consisting of a 19 amino acid BoNT/A immunoreactive fragment consisting of amino acids 785-803 of SEQ ID NO: 1 or said 19 amino acid BoNT/A immunoreactive fragment having 1-4 conservative amino acid substitutions;
wherein said 19 amino acid BoNT/A immunoreactive fragment having 1-4 conservative amino acid substitutions is immunoreactive with BoNT/A.

5. The BoNT/A peptide of claim 4, wherein said 19 amino acid BoNT/A immunoreactive fragment is amino acids 785-803 of SEQ ID NO: 1.

6. An isolated botulinum toxin serotype A (BoNT/A) peptide of SEQ ID NO: 1 having a length of at most 15 amino acids, said BoNT/A peptide comprising a 10 amino acid BoNT/A immunoreactive fragment consisting of amino acids 785-794 of SEQ ID NO: 1 or said 10 amino acid BoNT/A immunoreactive fragment having 1-4 conservative amino acid substitutions;
wherein said 10 amino acid BoNT/A immunoreactive fragment having 1-4 conservative amino acid substitutions is immunoreactive with BoNT/A.

7. The BoNT/A peptide of claim 6, wherein said 10 amino acid BoNT/A immunoreactive fragment is amino acids 785-794 of SEQ ID NO: 1.

8. The BoNT/A peptide of claim 1, wherein said BoNT/A peptide has a length of at most 20 amino acids.

9. An isolated botulinum toxin serotype A (BoNT/A) peptide consisting of a 10 amino acid BoNT/A immunoreactive fragment consisting of amino acids 785-794 of SEQ ID NO: 1 or said 10 amino acid BoNT/A immunoreactive fragment having 1-4 conservative amino acid substitutions;
wherein said 10 amino acid BoNT/A immunoreactive fragment having 1-4 conservative amino acid substitutions is immunoreactive with BoNT/A.

10. The BoNT/A peptide of claim 9, wherein said 10 amino acid BoNT/A immunoreactive fragment is amino acids 785-794 of SEQ ID NO: 1.

* * * * *

UNITED STATES PATENT AND TRADEMARK OFFICE
CERTIFICATE OF CORRECTION

PATENT NO. : 7,635,484 B2
APPLICATION NO. : 11/693111
DATED : December 22, 2009
INVENTOR(S) : M. Zouhair Atassi It is certified that error appears in the above-identified patent and that said Letters Patent is hereby corrected as shown below:

On the title page, in item (62), in column 1, under "Related U.S. Application Data", line 1, delete "Division" and insert -- Continuation --, therefor.

On page 2, in column 1, under "Other Publications", line 3, delete "a" and insert -- A --, therefor.

On page 2, in column 1, under "Other Publications", line 6, delete "e tal," and insert -- et al., --, therefor.

On page 2, in column 1, under "Other Publications", line 28, delete "HN-domain" and insert -- $H_N$-domain --, therefor.

On page 2, in column 1, under "Other Publications", line 29-30, delete "continuous antigenic regions of the continuous antigenic regions of the" and insert -- continuous antigenic regions of the --, therefor.

On page 2, in column 1, under "Other Publications", line 42, delete "synaptosomes "Infection" and insert -- synaptosomes," Infection --, therefor.

On page 2, in column 2, under "Other Publications", line 4, delete "bolulinum" and insert -- botulinum --, therefor.

On page 2, in column 2, under "Other Publications", line 40, delete "al .," and insert -- al., --, therefor.

On page 2, in column 2, under "Other Publications", line 44, delete "a,"" and insert -- A," --, therefor.

On page 2, in column 2, under "Other Publications", line 47, delete "botulinum ," and insert -- botulinum --, therefor.

On page 2, in column 2, under "Other Publications", line 51, delete "botulinum,"Vaccine" and insert -- botulinum," Vaccine --, therefor.

On page 2, in column 2, under "Other Publications", line 54, delete "Alessi," and insert -- Atassi, --, therefor.

On page 2, in column 2, under "Other Publications", line 56, delete "lmmunol." and insert -- Immunol. --, therefor.

On page 2, in column 2, under "Other Publications", line 61-62, delete "1029-1041,2007" and insert -- 1029-1041, 2007. --, therefor.

CERTIFICATE OF CORRECTION (continued)
U.S. Pat. No. 7,635,484 B2

On page 2, in column 2, under "Other Publications", line 67-68, delete "nonneutralizing" and insert -- non-neutralizing --, therefor.

On page 3, in column 1, under "Other Publications", line 3, delete "Implication sof" and insert -- Implications of --, therefor.

On page 3, in column 1, under "Other Publications", line 9, delete "eta" and insert -- et --, therefor.

On page 3, in column 1, under "Other Publications", line 13, delete "Poreteins" and insert -- Proteins --, therefor.

On page 3, in column 1, under "Other Publications", line 14, delete "Plunum" and insert -- Plenum --, therefor.

On page 3, in column 1, under "Other Publications", line 27, delete "($H_c$ )" and insert -- ($H_c$) --, therefor.

On page 3, in column 1, under "Other Publications", line 28, delete "$H_c$," and insert -- $H_c$, --, therefor.

On page 3, in column 1, under "Other Publications", line 32, delete "toxin,"Mol." and insert -- toxin," Mol. --, therefor.

On page 3, in column 1, under "Other Publications", line 38, delete "Immun69:570-574" and insert -- Immun. 69:570-574 --, therefor.

On page 3, in column 2, under "Other Publications", line 19, delete "purifed" and insert -- purified --, therefor.

On page 3, in column 2, under "Other Publications", line 24, delete "Development" and insert -- Developmental --, therefor.

On page 3, in column 2, under "Other Publications", line 27, delete "botuliman" and insert -- botulinum --, therefor.

In Sheet 3 of 28, in Fig. 2, line 1, delete "Antis e ra d ilutio n" and insert -- Antisera dilution --, therefor.

In Sheet 3 of 28, in Fig. 2, line 2, delete "Antis e ra d ilutio n" and insert -- Antisera dilution --, therefor.

In Sheet 3 of 28, in Fig. 2, line 9, delete "BNT/A" and insert -- BoNT/A --, therefor.

In Sheet 4 of 28, in Fig. 3, line 10, delete "BNT/A" and insert -- BoNT/A --, therefor.

In Sheet 5 of 28, in Fig. 4, line 9, delete "BNT/A" and insert -- BoNT/A --, therefor.

CERTIFICATE OF CORRECTION (continued)
U.S. Pat. No. 7,635,484 B2

In Sheet 6 of 28, in Fig. 5, line 8, delete "BNT/A" and insert -- BoNT/A --, therefor.

In Sheet 9 of 28, in Fig 8, line 9, delete "BNT/A" and insert -- BoNT/A --, therefor.

In Sheet 9 of 28, in Fig. 8, line 9, delete "BNT/B" and insert -- BoNT/B --, therefor.

Figure 11:
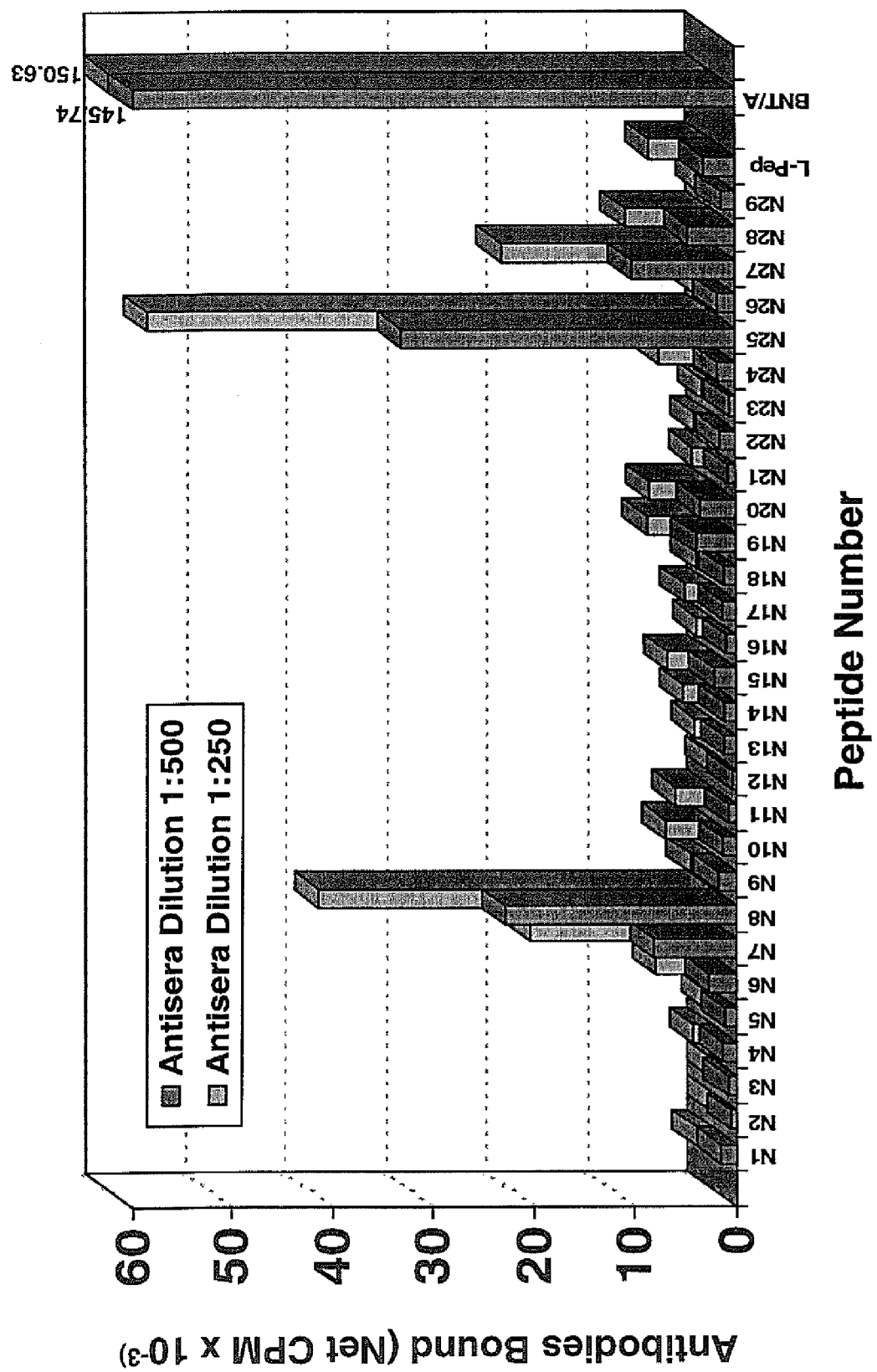
FIG. 11 shows binding of Balb/c anti-BoNT/A antibodies to BoNT/A and to overlapping synthetic peptides spanning the $H_N$-domain. Antisera were assayed at two dilutions (1:500 and 1:250, vol/vol).

In Sheet 12 of 28, in Fig. 11, line 9, delete "BNT/A" and insert -- BoNT/A --, therefor.

Figure 12:
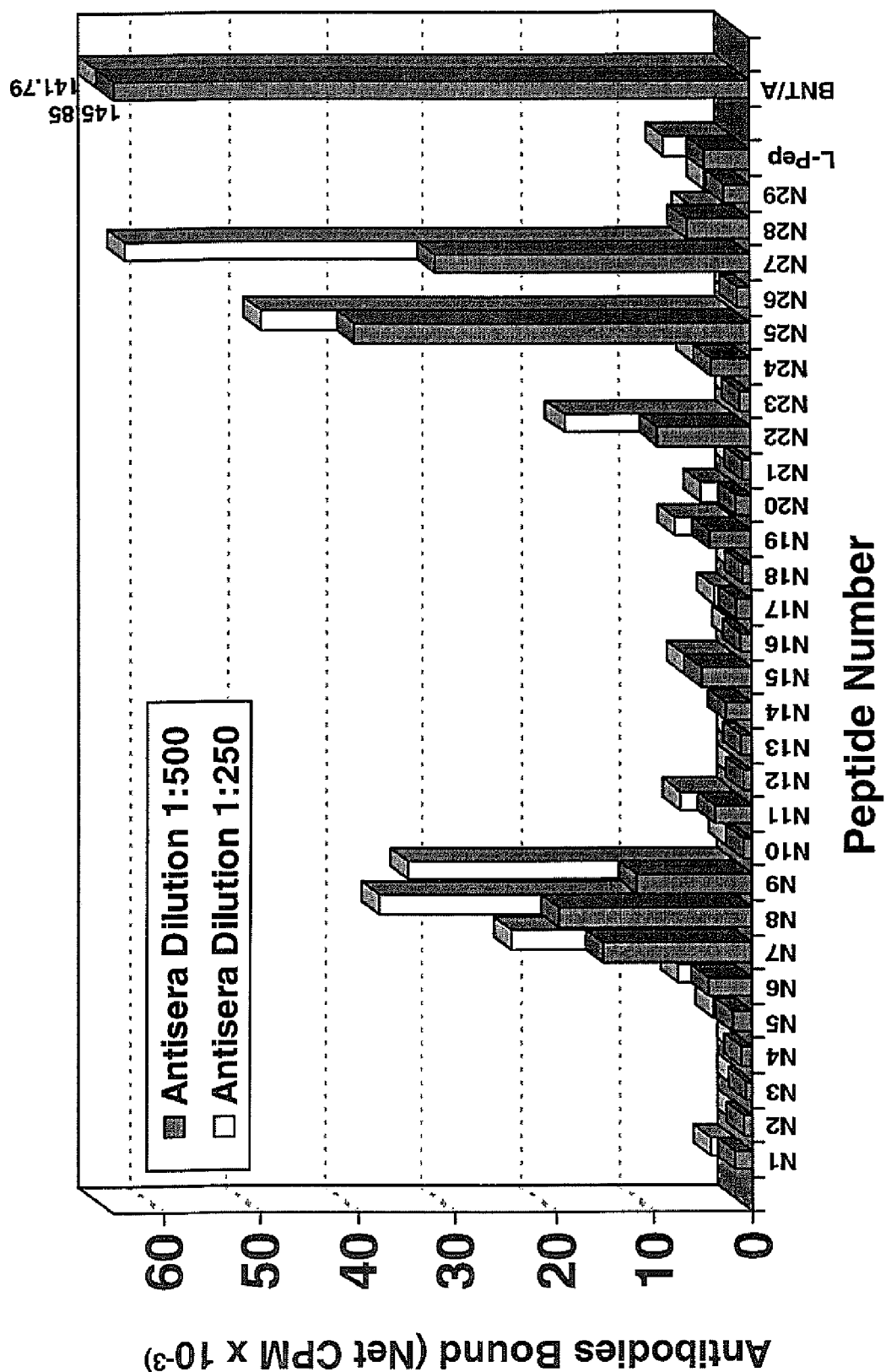
FIG. 12 shows binding of SJL anti-BoNT/A antibodies to BoNT/A and to overlapping synthetic peptides of the $H_N$-chain. Antisera were assayed at dilutions of 1:500 and 1:250.

In Sheet 13 of 28, in Fig. 12, line 9, delete "BNT/A" and insert -- BoNT/A --, therefor.

In Sheet 15 of 28, in Fig. 14, line 1, delete "Per cent" and insert -- Percent --, therefor.

In Sheet 19 of 28, in Fig. 18, line 2, delete "protectg" and insert -- protecting --, therefor.

In Sheet 19 of 28, in Fig. 18, line 12, delete "protectg" and insert -- protecting --, therefor.

In Sheet 20 of 28, in Fig. 19, line 2, delete "protectg" and insert -- protecting --, therefor.

In Sheet 20 of 28, in Fig. 19, line 2, delete "Prot" and insert -- Protecting --, therefor.

In Sheet 22 of 28, in Fig. 22, line 1 (Y-axis), delete "toBoNTB" and insert -- to BoNT/B --, therefor.

In column 1, line 6, delete "Divisional" and insert -- Continuation --, therefor.

In column 1, line 9, delete "entirely." and insert -- entirety. --, therefor.

In column 2, line 40, delete "NO:1655-681" and insert -- NO:1, 655-681 --, therefor.

In column 3, line 47, delete "NO:1823-849" and insert -- NO:1, 823-849 --, therefor.

In column 5, line 11, delete "Balb/c" and insert -- BALB/c --, therefor.

In column 5, line 20, delete "Balb/c" and insert -- BALB/c --, therefor.

In column 13, line 34, delete "derivitization" and insert -- derivatization --, therefor.

In column 30, line 53, delete "herein," and insert -- herein. --, therefor.

In column 31, line 6, delete "polyproplene" and insert -- polypropylene --, therefor.

In column 31, line 18, delete "noncovalently" and insert -- non-covalently --, therefor.

In column 37, line 50, delete "C9/C110/C11" and insert -- C9/C10/C11 --, therefor.

In column 37, line 66, delete "C1," and insert -- C11, --, therefor.

In column 38, line 66, delete "Hc" and insert -- $H_c$ --, therefor.

In column 41, line 24, delete "Hc" and insert -- $H_c$ --, therefor.

In column 46, line 22, delete "Hc" and insert -- $H_c$ --, therefor.

In column 47, line 53, delete "Anti-Bont/A" and insert -- Anti-BoNT/A --, therefor.

In column 52, line 14, delete "(O)" and insert -- (±) --, therefor.

Signed and Sealed this

Twentieth Day of April, 2010

David J. Kappos
*Director of the United States Patent and Trademark Office*